(12) United States Patent
Bukh et al.

(10) Patent No.: US 10,280,404 B2
(45) Date of Patent: May 7, 2019

(54) OPTIMIZED HCV FULL-LENGTH INFECTIOUS CELL CULTURE SYSTEMS AND APPLICATIONS THEREOF

(71) Applicants: Hvidore Hospital, Hvidovre (DK); Københavns Universitet, København N (DK)

(72) Inventors: Jens Bukh, Præstø (DK); Yiping Li, Hvidovre (DK); Santseharay Ramirez Almeida, Hvidovre (DK)

(73) Assignees: Hvidovre Hospital, Hvidovre (DK); Københavns Universitet, København (DK)

( * ) Notice: Subject to any disclaimer, the term of this patent is extended or adjusted under 35 U.S.C. 154(b) by 0 days.

(21) Appl. No.: 15/522,745

(22) PCT Filed: Oct. 23, 2015

(86) PCT No.: PCT/DK2015/050325
§ 371 (c)(1),
(2) Date: Apr. 27, 2017

(87) PCT Pub. No.: WO2016/066171
PCT Pub. Date: May 6, 2016

(65) Prior Publication Data
US 2018/0201905 A1    Jul. 19, 2018

(30) Foreign Application Priority Data
Oct. 28, 2014    (DK) .................................. 2014 70659

(51) Int. Cl.
*C12N 7/00*    (2006.01)
*C12Q 1/70*    (2006.01)

(52) U.S. Cl.
CPC ................. *C12N 7/00* (2013.01); *C12Q 1/70* (2013.01); *C12N 2770/24221* (2013.01); *C12N 2770/24222* (2013.01); *C12N 2770/24251* (2013.01); *G01N 2500/04* (2013.01)

(58) Field of Classification Search
None
See application file for complete search history.

(56) References Cited

U.S. PATENT DOCUMENTS

| 8,454,974 | B2 | 6/2013 | Scheel et al. |
| 8,506,969 | B2 | 8/2013 | Gottwein et al. |
| 8,563,706 | B2 | 10/2013 | Scheel et al. |
| 8,569,472 | B2 | 10/2013 | Gottwein et al. |
| 8,618,275 | B2 | 12/2013 | Jensen et al. |
| 8,663,653 | B2 | 3/2014 | Gottwein et al. |
| 8,772,022 | B2 | 7/2014 | Gottwein et al. |
| 8,846,891 | B2 | 9/2014 | Prento et al. |
| 9,382,517 | B2 * | 7/2016 | Li ........................... C12N 7/00 |
| 9,388,389 | B2 | 7/2016 | Scheel et al. |
| 2006/0210969 | A1 | 9/2006 | Rice et al. |
| 2009/0252755 | A1 | 10/2009 | Bukh et al. |
| 2010/0093841 | A1 | 4/2010 | Gottwein et al. |
| 2013/0243841 | A1 | 9/2013 | Kommareddy et al. |
| 2016/0244729 | A1 | 8/2016 | Li et al. |

FOREIGN PATENT DOCUMENTS

| WO | WO-2011038737 A1 | 4/2001 |
| WO | WO-2006096459 A2 | 9/2006 |
| WO | WO-2008125119 A1 | 10/2008 |
| WO | WO-2010017818 A1 | 2/2010 |
| WO | WO-2010022727 A1 | 3/2010 |
| WO | WO2013/139339 | * 9/2013 ............... C12N 7/00 |
| WO | WO-2013/139339 A1 | 9/2013 |
| WO | WO-2013/139340 A1 | 9/2013 |
| WO | WO-2015014369 A1 | 2/2015 |
| WO | WO-2015/058772 A2 | 4/2015 |
| WO | WO-2015058772 A3 | 4/2015 |
| WO | WO-2015158353 A1 | 10/2015 |
| WO | WO-2015/179204 A1 | 11/2015 |
| WO | WO-2016/066171 | 5/2016 |

OTHER PUBLICATIONS

"Synthetic construct Hepatitis C virus ED43 polyprotein gene, complete cds", GenBank: GU814266, (May 4, 2010), 4 pgs.
GenBank: AF009606.1. Hepatitis C virus subtype 1a polyprotein gene, complete cds, (Jun. 18, 2009).
GenBank: BAD73984.1. Polyprotein, Partial [Hepatitis C virus subtype 1B], (Oct. 17, 2018).
Sequence No. UPI00029CEA20, Database: UniParc (from Database: EMBL CDS, Entry No. AFX74877), (Nov. 28, 2012), 2 pgs.
Akazawa, D, et al., "Neutralizing Antibodies induced by Cell Culture-Derived Hepatitis C Virus Protect Against Infectin in Mice", Gastroenterology, vol. 145, No. 2, (Aug. 1, 2013), 447-455.
Akazawa, D, et al., "Production and Characterization of HCV Particles from Serum-Free Culture", Vaccine, Elsevier Ltd., vol. 29, No. 29, (Apr. 19, 2011), 4821-4828.
Altschul, S F, et al., "Protein Database Searches for Multiple Alignments", Proc. Natl. Acad. Sci. USA vol. 87, (Jul. 1990), 5509-5513.
Altschul, S. F., et al., "Basic Local Alignment Search Tool", J. Mol. Biol., 215, (1990), 403-410.

(Continued)

*Primary Examiner* — Agnieszka Boesen

(74) *Attorney, Agent, or Firm* — Schwegman Lundberg & Woessner, P.A.

(57) ABSTRACT

The present invention relates to nucleic acid sequences that encode hepatitis C viruses (HCV) that are useful in the fundamental research of HCV as well as in the search of a vaccine against HCV. In particular the present invention relates to nucleic acid sequences that comprises HCVs which are capable of expressing said virus when transfected into cells and are capable of infectivity in vivo.

5 Claims, 9 Drawing Sheets
Specification includes a Sequence Listing.

(56) References Cited

OTHER PUBLICATIONS

Bukh, et al., "A Milestone for Hepatitis C Virus Research: A Virus Generated in Cell Culture is Fully Viable in Vivo", Proceedings of the National Academy of Sciences of the United States of America, vol. 103, No. 10, (Mar. 2006), 3500-3501.
Bukh, J, et al., "Challenge Pools of Hepatitis C Virus Genotypes 1-6 Prototype Strains: Replication Fitness and Pathogenicity in Chimpanzees and Human Liver-Chimeric Mouse Models", J Infect Dis, vol. 201, No. 9, (May 1, 2010), 1381-9.
Chen, N, et al., "Oxymatrine Inhibits Target Cell Infection in the HCVcc System", Zhonghua Gan Zang Bing Za Zhi, vol. 24, No. 1, (Jan. 2016), 40-5.
Date, T, et al., "Novel Cell Culture-Adapted Genotype 2a Hepatitis C Virus Infectious Clone", J Virol., vol. 86, No. 19, (Oct. 2012), 10805-20.
Engle, R E, et al., "Development of a Taqman Assay for the Six Major Genotypes of Hepatitis C Virus: Comparison with Commercial Assays", J Med Virol., vol. 80, No. 1, (Jan. 2008), 72-9.
Gottwein, J M, et al., "Combination Treatment with Hepatitis C Virus Protease and NS5A Inhibitors is Effective Against Recombinant Genotype 1a, 2a, and 3a Viruses", Antimicrob Agents Chemother, vol. 57, No. 3, (Mar. 2013), 1291-303.
Gottwein, J M, et al., "Development and Characterization of Hepatitis C Virus Genotype 1-7 Cell Culture Systems: Role of Cd81 and Scavenger Receptor Class B Type I and Effect of Antiviral Drugs", Hepatology, vol. 49, No. 2, (Feb. 2009), 364-377.
Houghton, M, et al., "An Inactivated Hepatitis C Virus Vaccine on the Horizon?", Editorials, (2013), 285-288.
Kolykhalov, A A, et al., "Transmission of Hepatitis C by Intrahepatic Inoculation with Transcribed RNA", Science (New York), vol. 227, No. 5325, (Jul. 25, 1997), 570-574.
Kuiken, et al., "A comprehensive System for Consistent Numbering of HCV Sequences, Proteins and Epitopes", Hepatology, vol. 44, No. 5, (Nov. 2006), 1355-61.
Li, Y P, et al., "Differential Sensitivity of 5'UTR-NS5A Recombinants of Hepatitis C Virus Genotypes 1-6 to Protease and NS5A Inhibitors", Gastroenteroloty, vol. 146, No. 3, (Mar. 2014), 812-821 e4.
Li, Y P, et al., "Efficient Infectious Cell Culture Systems of the Hepatitis C Virus Prototype Strains Hcv-1 and H77", JV1-02877-14R1, (Oct. 21, 2014).
Li, Y P, et al., "Highly Efficient Full-Length Hepatitis C Virus Genotype 1 (strain Tn) Infectious Culture System", Proc Natl Acad Sci U S A, vol. 109, No. 48, (Nov. 27, 2012), 19757-62.
Li, Y P, et al., "Microrna-122 Antagonism Against Hepatitis C Virus Genotypes 1-6 and Reduced Efficacy by Host RNA Insertion or Mutations in the HCV 5' UTR", Proc Natl Acad Sci U S A, vol. 108, No. 12, (Mar. 22, 2011), 4991-4996.
Li, Y P, et al., "Non-Genotype-Specific Role of the Hepatitis C Virus 5' Untranslated Region in Virus Production and in Inhibition by Interferon", Virology, 20, vol. 421, No. 2, (Dec. 2011), 222-34.
Li, Y P, et al., "Protease Inhibitors Differentially Inhibit Novel Hcv 5'UTR-Ns5a Genotype 3-6 Recombinants", article intended for submission to Gastroenterology, vol. 146, No. 3, (Mar. 2014), 812-821.
Li, Y P, et al., "Robust Full-Length Hepatitis C Virus Genotype 2a and 2b Infectious Cultures Using Mutations Identified by a Systematic Approach Applicable to Patient Strains", Proc Natl Acad Sci U S A, vol. 109, No. 18, (May 1, 2012), E1101-10.
Lindenbach, B D, et al., "Complete Replication of Hepatitis C Virus in Cell Culture", Science, 22, vol. 309, No. 5734, (Jul. 2005), 623-6.
Mathiesen, C K, et al., "Production and Characterization of High-Titer Serum-Free Cell Culture Grown Hepatitis C Virus Particles of Genotype 1", Virology, Elsevier, vol. 458, (May 24, 2014), 190-208.

Morris, D L, et al., "Adipose Tissue Macrophages Function as Antigen-Presenting Cells and Regulate Adipose Tissue CD4+ T Cells in Mice", Diabetes, vol. 62, No. 8, (Mar. 14, 2013), 2762-2772.
Murayama, A, et al., "RNA Polymerase Activity and Specific RNA Structure are Required for Efficient HCV Replication in Cultured Cells", PLoS Pathog., vol. 6, No. 4, (Apr. 29, 2010), p. e1000885.
Murayama, A, et al., "The Ns3 Helicase and Ns5b-To-3'X Regions are Important for Efficient Hepatitis C Virus Strain Jfh-1 Replication in Huh7 Cells", J Virol., 8 vol. 81, No. 15, (Aug. 2007), 8030-40.
Okamoto, H, et al., "Full-Length Sequence of a Hepatitis C Virus Genome Having Poor Homology to Reported Isolates: Comparative Study of Four Distinct Genotypes", Virology, vol. 188, No. 1, (May 1992), 331-41.
Okamoto, H, et al., "Nucleotide Sequence of the Genomic RNA of Hepatitis C Virus Isolated From a Human Carrier: Comparison with Reported Isolates for Conserved and Divergent Regions", J Gen Virol., vol. 72, No. Pt 11, (Nov. 1991), 2697-704.
Ramirez, S, et al., "Highly Efficient Infectious Cell Culture of Three HCV Genotype 2b Strains and Sensitivity to Lead Protease, NS5A, and Polymerase Inhibitors", Submitted to Hepatology on Jun. 12, 2013.
Ramirez, S, et al., "Highly Efficient Infectious Cell Culture of Three Hepatitis C Virus Genotype 2b Strains and Sensitivity to Lead Protease, Nonstructural Protein 5a, and Polymerase Inhibitors", Hepatology, vol. 59, No. 2, (Feb. 2014), 395-407.
Scheel, TK H, et al., "Recombinant HCV Variants with NS5A from Genotypes 1-7 have Different Sensitivities to an NS5A Inhibitor but not Interferon-a", Gastroenterology, vol. No. 3, (Mar. 2011), 1032-1042.
Shiokawa, M, et al., "Novel Permissive Cell Lines for Complete Propagation of Hepatitis C Virus", J Virol., vol. 88, No. 10, (May 2014), 5578-94.
Wakita, T, et al., "Production of Infectious Hepatitis C Virus in Tissue Culture From a Cloned Viral Genome", Nat Med., vol. 11, No. 7, (Jul. 2005), 791-6.
Yanagi, M, et al., "Hepatitis C Virus: An Infectious Moleculer Clone of A Second Major Genotype (2a) and Lack of Viability of Intertypic 1a and 2a Chimeras", Virology, vol. 262, No. 1, (Sep. 1999), 250-263.
Yao, X, et al., "Baculovirus Mediated Production of Infectious Hepatitis C Virus in Human Hepatoma Cells Stably Expressing T7 RNA Polymerase", Molecular Biotechnology, vol. 40, No. 2, (Jun. 10, 2008), 186-194.
"International Application No. PCT/DK2015/050325, International Preliminary Report on Patentability dated May 11, 2017", 11 pgs.
"International Application No. PCT/DK2015/050325, International Search Report dated Feb. 4, 2016", (Feb. 4, 2016), 5 pgs.
"International Application No. PCT/DK2015/050325, Written Opinion dated Feb. 4, 2016", 9 pgs.
Yi-Ping, Li, et al., "Ef?cient Infectious Cell Culture Systems of the Hepatitis C Virus (HCV) Prototype Strains HCV-1 and H77", *Journal of Virology*, 89(1), (Jan. 2015), 811-823.
Murayama, Asako, et al., "Production of Infectious Chimeric Hepatitis C Virus Genotype 2b Harboring Minimal Regions of JFH-1", J. Virol., 86(4), (2012), 2143-2152.
Scheel, Troels K. H., et al., "Development of JFH1-based cell culture systems for hepatitis C virus genotype 4a and evidence for cross-genotype neutralization", Proc. Natl. Acad. Sci. USA. 105(3), (2008), 997-1002.
Zolotukhin, S., et al., "Recombinant adeno-associated virus purification using novel methods improves infectious titer and yield", Gene Therapy, 6, (1999), 973-985.

\* cited by examiner

A
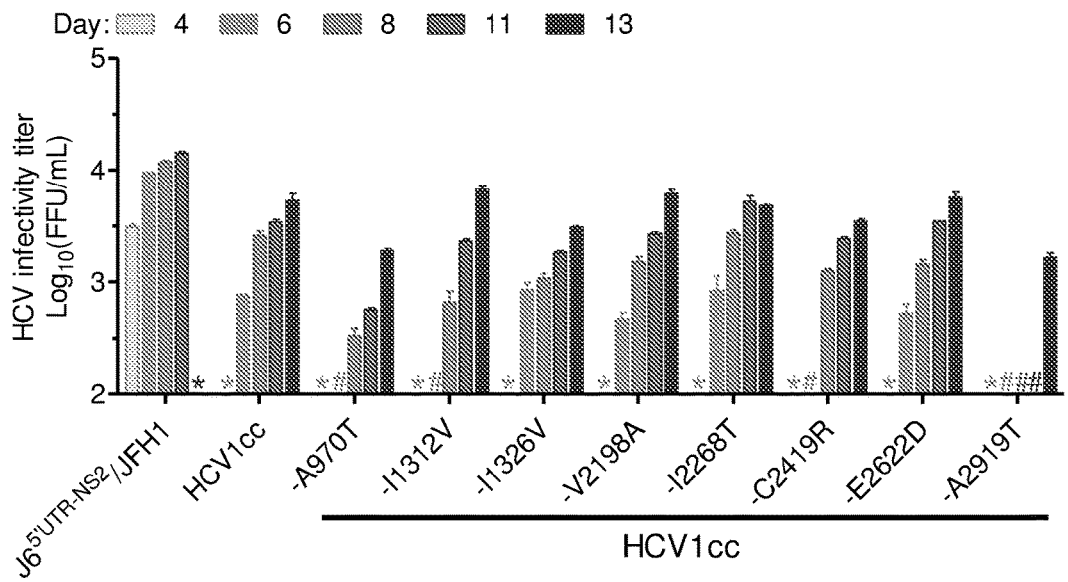
B
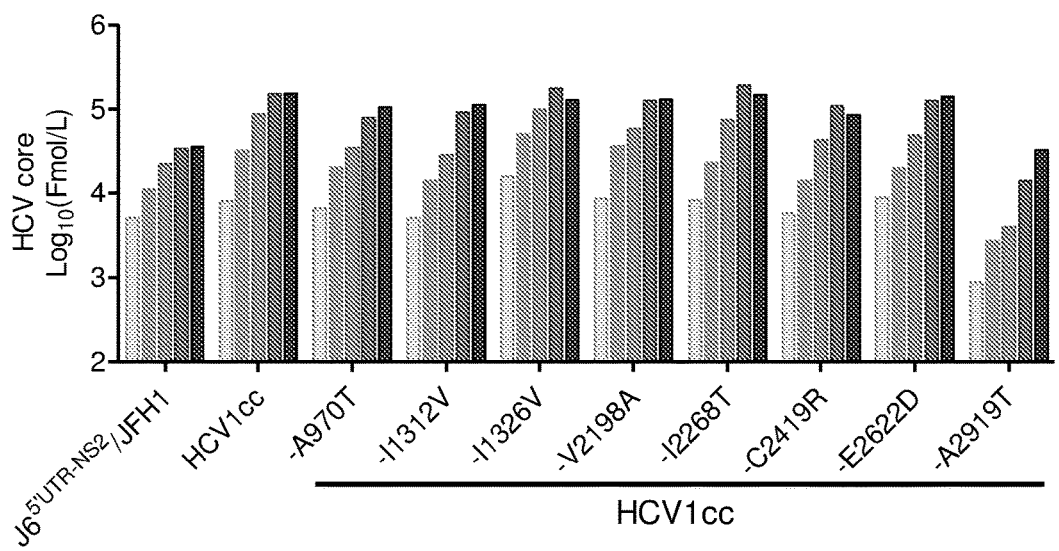
Fig. 2

A
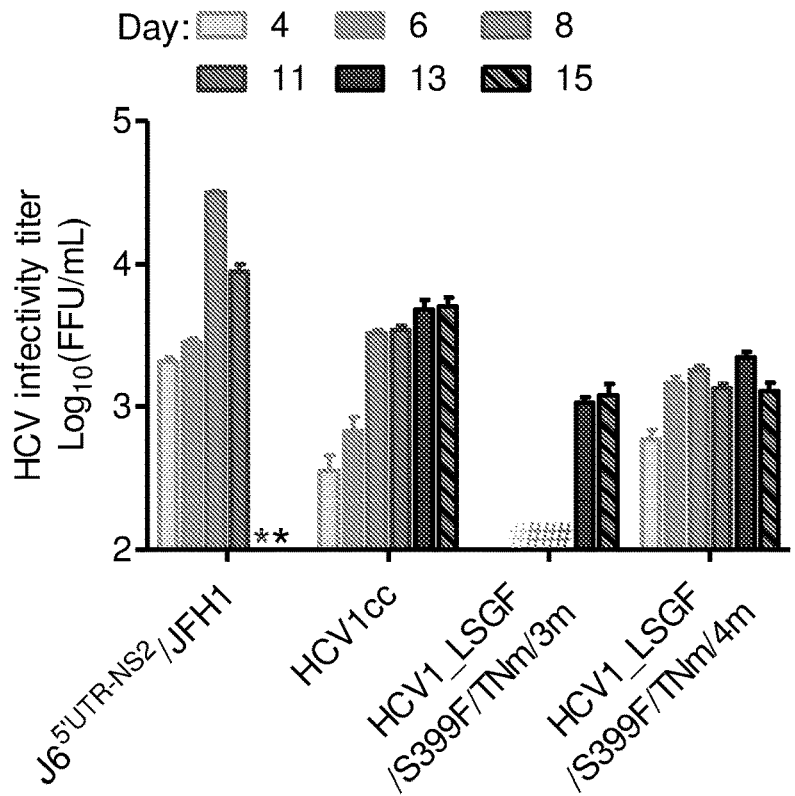
B
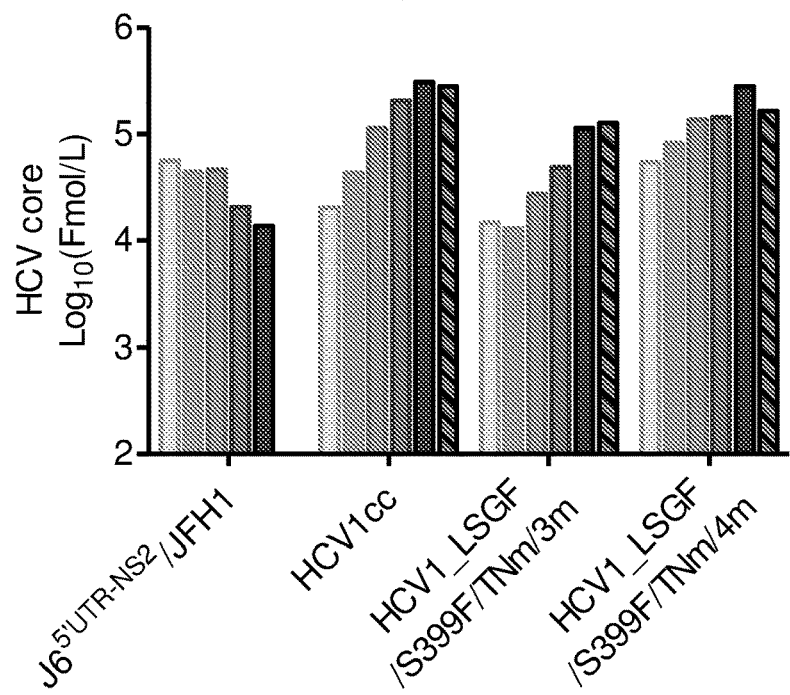
Fig. 3

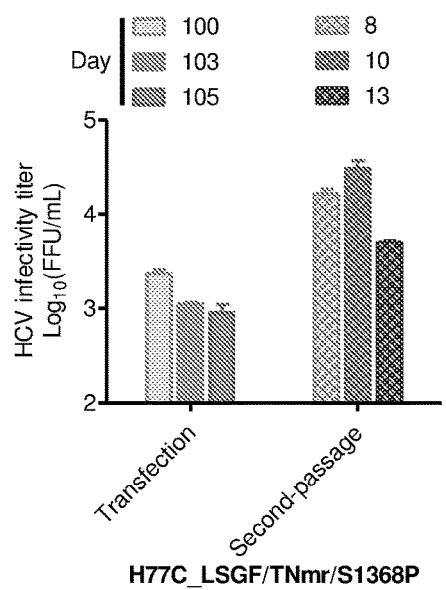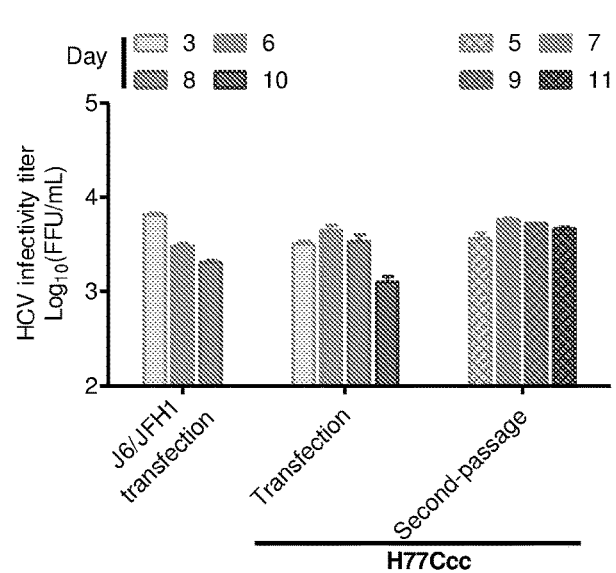
Fig. 5

Table 1. Characteristics of the HCV-1 5'UTR-NS5A (5-5A) recombinant and full-length viruses in Huh7.5 cell cultures.

| | Transfection | | First passage | | Second passage | | |
|---|---|---|---|---|---|---|---|
| | Day with ≥80% infected | Peak log₁₀FFU/ml (day) | Day with ≥80% infected | Peak log₁₀FFU/ml (day) | Day, ≥80% infected | Peak log₁₀FFU/ml (day) | Peak log₁₀IU/ml |
| HCV1(5-5A) | | | | | | | |
| +LSG/TN_GH, exp. 1 | 5 | <2.4 | 38 | 4.0 (42) | nd | - | - |
| +LSG/TN_GH, exp. 2ª | 5 | <2.4 | 27 | 4.0 (31) | 8 | 4.5 (8/10/12)ᵇ | nd |
| +LSG/S399F/TN_GH, exp. 1 | 4 | 2.7 (8) | 16 | 3.8 (18) | 5 | 4.4 (7) | nd |
| +LSG/S399F/TN_GH, exp. 2 | 4 | 3.0 (12) | 16 | 3.9 (16) | 5 | 4.2 (7) | nd |
| HCV1 full-length | | | | | | | |
| +LSGF/S399F/TNmᶜ | 26 | 3.3 (28) | 7 | 3.4 (11) | 7 | 4.3 (9) | 8.3 |
| +LSGF/S399F/TNm/8m (HCV1cc) | 3 | 3.8 (5)ᵈ | 5 | 3.8 (7) | 7 | 3.8 (9) | 7.5 |
| +LSGF/S399F/TNm/4m | 4 | 3.4 (13) | 11 | 3.5 (13) | 11 | 3.9 (15) | nd |

Fig. 6

Table 2. ORF sequence analysis of HCV-1 5'UTR-NS5A (5-5A) viruses.

| | Passage (Day) | E2 | NS3 | NS3 | NS3 | NS3 | NS3 | NS3 | NS4A | NS4B | NS5A | NS5A | NS5A | NS5B | NS5B |
|---|---|---|---|---|---|---|---|---|---|---|---|---|---|---|---|
| Nucleotide position | | | | | | | | | | | | | | | |
| Recombinant specific | | 1537 | 3477 | 4018 | 4234 | 4443 | 4731 | 4989 | 5355 | 5660 | 6987 | 7172 | 7588 | 7899 | 9277 |
| H77 reference (AF009606) | | 1537 | 3477 | 4018 | 4234 | 4443 | 4731 | 4989 | 5355 | 5660 | 6987 | 7172 | 7588 | 7899 | 9277 |
| Recombinant nucleotide | | C | A | C | A | T | T | G | G | A | A | G | A | A | A |
| HCV1(5-5A) | | | | | | | | | | | | | | | |
| +LSG/$TN_{GH}$, exp. 2 | 1st (31)[c] | T | • | G | • | • | C | • | T | C | • | • | G | A/C | G |
| | 2nd (8/10/12)[b] | T | G/a | G | T/a | C/t | C | • | T | C | A/C | G/C | G | C | G |
| +LSG/S399F/$TN_{GH}$, exp. 1 | 2nd (9)[c] | T | • | G | • | T/C | C | G/T | T | C | • | • | • | • | G |
| Amino acid position | | | | | | | | | | | | | | | |
| Recombinant specific | | 399 | 1046 | 1226 | 1298 | 1368 | 1464 | 1550 | 1672 | 1773 | 2216 | 2277 | 2416 | 2520 | 2979 |
| H77 reference (AF009606) | | 399 | 1046 | 1226 | 1298 | 1368 | 1464 | 1550 | 1672 | 1773 | 2216 | 2277 | 2416 | 2520 | 2979 |
| Amino acid change | | S-F | S-G | A-G | K-M | S-P | F-L | V-L | A-S | Q-H | T-P | K-N | D-G | K-Q | D-G |

Fig. 7

Table 3. ORF sequence analysis of HCV-1 full-length viruses.

| | Passage (day) | E2 | NS2 | NS3 | NS3 | NS3 | NS3 | NS4A | NS4B | NS5A | NS5A | NS5A | NS5B | NS5B | NS5B | NS5B |
|---|---|---|---|---|---|---|---|---|---|---|---|---|---|---|---|---|
| Nucleotide position | | | | | | | | | | | | | | | | |
| Recombinant specific | | 1537 | 3249 | 4018 | 4275 | 4317 | 4731 | 5355 | 5660 | 6121 | 6934 | 7144 | 7596 | 8207 | 9096 | 9277 | 9283 | 9322 |
| H77 reference (AF009606) | | 1537 | 3249 | 4018 | 4275 | 4317 | 4731 | 5355 | 5660 | 6121 | 6934 | 7144 | 7596 | 8207 | 9096 | 9277 | 9283 | 9322 |
| Recombinant nucleotide | | C | A | C | A | A | T | G | A | A | T | T | C | C | A | A | A | T |
| HCV-1 full-length | | | | | | | | | | | | | | | | | | |
| +LSGF/S399F/TNm | 2nd (11) | T | A | G | G | G | C | T | C | C | C | C | C | C | . | G | T | C |
| | 3rd (11) | T | A | G | G | G | C | T | C | C | C | C | C | C | A | G | T | C |
| +LSGF/S399F/TNm/8m (HCV1cc) | 2nd (9) | T | A | G | G | G | C | T | C | C | C | C | C | C | A | G | T | C |
| +LSGF/S399F/TNm/4m | 2nd (18) | T | A | G | G | . | C | T | C | C | . | . | . | . | A | G | T | C |
| Amino acid position | | | | | | | | | | | | | | | | | | |
| Recombinant specific | | 399 | 970 | 1226 | 1312 | 1326 | 1464 | 1672 | 1773 | 1927 | 2198 | 2268 | 2419 | 2622 | 2919 | 2979 | 2981 | 2994 |
| H77 reference (AF009606) | | 399 | 970 | 1226 | 1312 | 1326 | 1464 | 1672 | 1773 | 1927 | 2198 | 2268 | 2419 | 2622 | 2919 | 2979 | 2981 | 2994 |
| Amino acid change | | S-F | A-T | A-G | I-V | F-L | A-S | Q-H | N-T | V-A | I-T | C-R | E-D | A-T | D-G | Y-F | F-S |

Fig. 8

Table 4. ORF sequence analysis of H77C full-length viruses.

| Passage (Day) | | E1 | NS2 | NS2 | NS3 | NS3 | NS3 | NS3 | NS3 | NS4A | NS4A | NS4B | NS4B | NS4B | NS5A | NS5A | NS5A | NS5B | NS5B | NS5B | NS5B |
|---|---|---|---|---|---|---|---|---|---|---|---|---|---|---|---|---|---|---|---|---|---|
| Nucleotide position | | 1375 | 2824 | 2932 | 3496 | 4018 | 4443 | 4731 | 5329 | 5355 | 5660 | 6066 | 6121 | 6654 | 7401 | 7591 | 7632 | 9277 | 9283 | 9321[b] | 9322[b] |
| Nucleotide (pCV-H77C/X24) | | T | C | T | A | C | T | T | T | G | A | G | A | A | A | T | G | A | A | T | T |
| H77C_LSGF/TNnr/S1368P[a] | 1st (13) | C | T | G | G | G | C | C | C | T | G | A | A | G | G | C | A | G | T | C | C |
| | 2nd (13) | C | T | G | G | G | C | C | C | T | G | A | A | G | G | C | A | G | T | C | C |
| H77Ccc | 2nd (9) | C | T | G | G | G | C | C | C | T | A | A | A | G | G | C | A | G | T | C | C |
| | | 345 | 828 | 864 | 1032 | 1228 | 1368 | 1464 | 1663 | 1672 | 1773 | 1909 | 1927 | 2105 | 2354 | 2417 | 2431 | 2979 | 2981 | 2994 | 2994 |
| | | M-T | A-V | L-R | K-R | A-G | S-P | F-L | V-A | A-S | Q-H | G-S | N-T | M-V | S-G | V-A | V-I | D-G | Y-F | F-R | F-R |

SEQUENCE LISTING

<160> NUMBER OF SEQ ID NOS: 7

<210> SEQ ID NO 1
<211> LENGTH: 9618
<212> TYPE: DNA
<213> ORGANISM: Hepatitis C virus

<400> SEQUENCE: 1

```
gccagccccc tgatgggggc gacactccac catgaatcac tcccctgtga ggaactactg     60
tcttcacgca gaaagcgtct agccatggcg ttagtatgag tgtcgtgcag cctccaggac    120
cccccctccc gggagagcca tagtggtctg cggaaccggt gagtacaccg gaattgccag    180
gacgaccggg tcctttcttg gataaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gtcgcccaca ggacgtcaag ttcccgggtg    420
gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtaccttgg ccctctatg     600 gcaatgaggg ctgcgggtgg gcgggatggc tcctgtctcc ccgtggctct cggcctagct    660
ggggccccac agaccccgg cgtaggtcgc gcaatttggg taaggtcatc gatacccta     720 cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
```

```
ggaaccttcc tggttgctct ttctctatct tccttctggc cctgctctct tgcttgactg      900
tgcccgcttc ggcctaccaa gtgcgcaact ccacggggct ttaccacgtc accaatgatt      960
gccctaactc gagtattgtg tacgaggcgg ccgatgccat cctgcacact ccggggtgcg     1020
tcccttgcgt tcgcgagggc aacgcctcga ggtgttgggt ggcgatgacc cctacggtgg     1080
ccaccaggga tggcaaactc cccgcgacgc agcttcgacg tcacatcgat ctgcttgtcg     1140
ggagcgccac cctctgttcg gccctctacg tgggggacct gtgcgggtct gtctttcttg     1200
tcggccaact gttcaccttc tctcccaggc gccactggac gacgcaaggt tgcaattgct     1260
ctatctatcc cggtcatata acgggtcacc gcatggcatg ggatatgatg atgaactggt     1320
cccctacgac ggcgttggta atggctcagc tgctccgcat cccacaagcc atcttggaca     1380
tgatcgctgg tgctcactgg ggagtcctgg cgggcatagc gtatttctct atggtgggaa     1440
actgggcgaa ggtcctggta gtgctgctgc tatttgccgg cgtcgacgcg gaaacccacg     1500
tcaccggggg aagtgccggc cacactgtgt ctggatttgt tagcttcctc gcaccaggcg     1560
ccaagcagaa tgtccagctg atcaacacca acggcagttg gcacctcaat agcacggccc     1620
tgaactgcaa tgatagcctt aacaccggct ggttggcagg gcttttctat caccacaagt     1680
tcaactcttc aggctgccct gagaggctag ccagctgccg acccttacc gattttgacc      1740 agggctgggg ccctatcagt tatgccaacg gaagcggccc cgaccagcgc ccctactgct     1800
ggcactaccc cccaaaacct tgcggtattg tgcccgcgaa gagtgtgtgt ggtccggtat     1860
attgcttcac tcccagcccc gtggtggtgg gaacgaccga caggtcgggc gcgcctacct     1920
acagctgggg tgaaaacgat acggacgttt tcgtccttaa caataccagg ccaccgctgg     1980
gcaattggtt cggttgtacc tggatgaact caactggatt caccaaagtg tgcggagcgc     2040
ctccttgtgt catcggaggg gcgggcaaca acaccctgca ctgccccact gattgcttcc     2100
gcaagcatcc ggacgccaca tactctcggt gcggctccgg tcctggatc acacccaggt      2160 gcctggtcga ttacccgtat aggctttggc attatccttg taccatcaac tacaccatat     2220
ttaaaattag gatgtacgtg ggaggggtcg agcacaggct ggaagctgcc tgcaactgga     2280
cgcggggcga acgttgcgat ctggaagata gggacaggtc cgagctcagc ccgttactgc     2340
tgaccactac acagtggcag gtcctcccgt gttccttcac aaccctgcca gccttgtcca     2400
ccggcctcat ccacctccac cagaacattg tggacgtgca gtacttgtac ggggtggggt     2460
caagcatcgc gtcctgggcc attaagtggg agtacgtcgt tctcctgttc cttctgcttg     2520
cagacgcgcg cgtctgctcc tgcttgtgga tgatgctact catatcccaa gcggaggcgg     2580 cttttggagaa cctcgtaata cttaatgcag catccctggc cgggacgcac ggtcttgtat     2640
ccttcctcgt gttcttctgc tttgcatggt atctgaaggg taagtgggtg cccggagcgg     2700
tctacacctt ctacgggatg tggcctctcc tcctgctcct gttggcgttg cccagcgggg     2760
cgtacgcgct ggacacggag gtggccgcgt cgtgtggcgg tgttgttctc gtcgggttga     2820
tggcgctgac tctgtcacca tattacaagc gctatatcag ctggtgcttg tggtggcttc     2880
agtattttct gaccagagtg gaagcgcaac tgcacgtgtg gattcccccc ctcaacgtcc     2940 gagggggggcg cgacgccgtc atcttactca tgtgtgctgt acacccgact ctggtatttg     3000
acatcaccaa attgctgctg gccgtcttcg gaccccttg gattcttcaa gccagcttgc      3060
ttaaagtacc ctactttgtg cgcgtccaag gccttctccg gttctgcgcg ttagcgcgga     3120
agatggccga aggccattac gtgcaaatgg tcatcattaa gttaggggcg cttactggca     3180
cctatgttta taaccacctc actcctcttc gggactgggc gcacaacggc ttgcgagatc     3240
```

```
tggccgtgac tgtagagcca gtcgtcttct cccaaatgga gaccaagctc atcacgtggg   3300
gggcagatac cgccgcgtgc ggtgacatca tcaacggctt gcctgtttcc gcccgcaggg   3360
gccgggagat actgctcggg ccagccgatg gaatggtctc caaggggtgg aggttgctgg   3420
cgcccatcac ggcgtacgcc cagcagacaa ggggcctcct agggtgcata atcaccagcc   3480
taactggccg ggacaaaaac caagtggagg gtgaggtcca gattgtgtca actgctgccc   3540
aaaccttcct ggcaacgtgc atcaatgggg tgtgctggac tgtctaccac ggggccggaa   3600
cgaggaccat cgcgtcaccc aagggtcctg tcatccagat gtataccaat gtagaccaag   3660
accttgtggg ctggcccgct ccgcaaggta gccgctcatt gacaccctgc acttgcggct   3720
cctcggacct ttacctggta acgaggcacg ccgatgtcat tcccgtgcgc cggcggggtg   3780
atagcagggg cagcctgctg tcgccccggc ccatttccta cttgaaaggc tcctcggggg   3840
gtccgctgtt gtgccccgcg gggcacgccg tgggtatatt tagggccgcg gtgtgcaccc   3900
gtggagtggc taaggcggtg gactttatcc ctgtggagaa cctagagaca accatgaggt   3960
ccccggtgtt cacggataac tcctctccac cagtagtgcc ccagagcttc caggtgggtc   4020
acctccatgc tcccacaggc agcggcaaaa gcaccaaggt cccggctgca tatgcagctc   4080
agggctataa ggtgctagta ctcaaccccct ctgttgctgc aacactgggc tttggtgctt   4140
acatgtccaa ggctcatggg atcgatccta acatcaggac cggggtgaga acaattacca   4200
ctggcagccc catcacgtac tccacctacg gcaagttcct tgccgacggc gggtgctcgg   4260
ggggcgctta tgacgtaata atttgtgacg agtgccactc cacggatgcc acatccgtct   4320
tgggcatcgg cactgtcctt gaccaagcag agactgcggg ggcgagactg gttgtgctcg   4380
ccaccgccac ccctcgggc tccgtcactg tgccccatcc caacatcgag gaggttgctc   4440
tgtccaccac cggagagatc cctttttacg gcaaggctat cccctcgaa gtaatcaagg   4500 gggggagaca tctcatcttc tgtcattcaa agaagaagtg cgacgaactc gccgcaaagc   4560
tggtcgcatt gggcatcaat gccgtggcct actaccgcgg tcttgacgtg tccgtcatcc   4620
cgaccagcgg cgatgttgtc gtcgtggcaa ccgatgccct catgaccggc tataccggcg   4680
acttcgactc ggtgatagac tgcaatacgt gtgtcaccca gacagtcgat ctcagccttg   4740
accctacctt caccattgag acaatcacgc tcccccagga tgctgtctcc cgcactcaac   4800
gtcggggcag gactggcagg gggaagccag gcatctacag atttgtggca ccggggagc   4860 gcccctctgg catgttcgac tcgtccgtcc tctgtgagtg ctatgacgca ggctgtgctt   4920
ggtatgagct cacgccccgcc gagactacag ttaggctacg agcgtacatg aacaccccgg   4980
ggcttcccgt gtgccaggac catcttgaat tttgggaggg cgtctttaca ggcctcactc   5040
atatagatgc ccactttcta tcccagacaa agcagagtgg ggagaacctt ccttacctgg   5100
tagcgtacca agccactgtg tgcgctaggg ctcaagcccc tccccatcg tgggaccaga   5160 tgtggaagtg tttgattcgc ctcaagccca ccctccatgg gccaacaccc ctgctataca   5220
gactgggcgc tgttcagaat gaaatcaccc tgacgcaccc agtcaccaaa tacatcatga   5280
catgcatgtc ggccgacctg gaggtcgtca cgagcacctg ggtgctcgtt ggcggcgtcc   5340
tggctgcttt ggcctcgtat tgcctgtcaa caggctgcgt ggtcatagtg gcagggtcg   5400 tcttgtccgg gaagccggca atcatacctg acagggaagt cctctaccaa gagttcgatg   5460
agatggaaga gtgctctcag cacttaccgt acatcgagca agggatgatg ctcgccgagc   5520
agttcaagca gaaggcccctc ggcctcctgc agaccgcgtc ccgtcaggca gaggttatcg   5580
```

```
cccctgctgt ccagaccaac tggcaaaaac tcgagacctt ctgggcgaag catatgtgga   5640
acttcatcag tgggatacac tacttggcgg gcttgtcaac gctgcctggt aaccccgcca   5700
ttgcttcatt gatggctttt acagctgctg tcaccagccc actaaccact agccaaaccc   5760
tcctcttcaa catattgggg gggtgggtgg ctgcccagct cgccgccccc ggtgccgcta   5820
ctgcctttgt gggcgctggc ttagctggcg ccgccatcgg cagtgttgga ctggggaagg   5880
tcctcataga catccttgca gggtatgcgc cgggcgtggc gggagctctt gtggcattca   5940
agatcatgag cggtgaggtc ccctccacgg aggacctggt caatctactg cccgccatcc   6000
tctcgcccgg agccctcgta gtcggcgtgg tctgtgcagc aatactgcgc cggcacgttg   6060
gcccgggcga gggggcagtg caatggatga accggctgat agccttcgcc tcccggggga   6120
cccatgtttc ccccacgcac tacgtgccgg agagcgatgc agctgcccgc gtcactgcca   6180
tactcagcag cctcactgta acccagctcc tgaggcgact gcaccagtgg ataagctcgg   6240
agtgtaccac tccatgctcc ggttcctggc taagggacat ctgggactgg atatgcgagg   6300
tgttgagcga ctttaagacc tggctaaaag ctaagctcat gccacagctg cctgggatcc   6360
cctttgtgtc ctgccagcgc gggtataagg gggtctggcg aggggacggc atcatgcaca   6420
ctcgctgcca ctgtggagct gagatcactg gacatgtcaa aaacgggacg atgaggatcg   6480
tcggtcctag gacctgcagg aacatgtgga gtgggacctt ccccattaat gcctacacca   6540
cgggcccctg tacccccctt cctgcgccga actacacgtt cgcgctatgg agggtgtctg   6600
cagaggaata cgtggagata aggcaggtgg gggacttcca ctacgtgacg ggtatgacta   6660
ctgacaatct taaatgcccg tgccaggtcc catcgcccga atttttcaca gaattggacg   6720
gggtgcgcct acataggttt gcgcccccct gcaagccctt gctgcgggag gaggtatcat   6780
ttagagtagg actccacgaa tacccggtag ggtcgcaatt accttgcgag cccgaaccgg   6840
acgtggccgt gttgacgtcc atgctcactg atccctccca tataacagca gaggcggccg   6900
ggcggaggtt ggcgagggga tcacccccct ctgcggccag ctcctcggct agccagctat   6960
ccgctccatc tctcaaggca acttgcaccg ctaaccatga ctcccctgat gctgagctca   7020
tagaagccaa cctcctatgg aggcaggaga tgggcggcaa catcaccagg gttgagtcag   7080
aaaacaaagt ggtgattctg gactccttcg atccgcttgt ggcggaggag gacgagcggg   7140
agacctccgt acccgcagaa atccgcggga agtctcggag attcgcccag gccctgcccg   7200
tttgggcgcg gccggactat aaccccccgc tagtggagac gtggaaaaag cccgactacg   7260
aaccacctgt ggtccatggc tgtccgcttc cacctccaaa gtcccctcct gtgcctccgc   7320
ctcggaagaa gcggacggtg gtcctcactg aatcaaccct atctactgcc ttggccgagc   7380
ttgccatcaa aagctttggc agctcctcaa cttccggcat tacgggcgac aatacgacaa   7440
catcctctga gccgcccct tctggctgcc ccgcgactc cgacgctgag tcctattcct   7500
ccatgccccc cctggagggg gagcctgggg atccggatct tagcgacggg tcatggtcaa   7560
cggtcagtag tgaggccagc gcggaggatg tcgtgcgctg ctcaatgtct tactcttgga   7620
caggcgcact cgtcacccg tgcgccgcgg aagaacagaa actgcccatc aatgcactga   7680
gcaactcgtt gctacgtcac cacaacttgg tgtattccac cacctcacgc agtgcttgcc   7740
aaaggcagaa gaaagtcaca tttgacagac tgcaagttct ggacagccat taccaggacg   7800
tgctcaagga ggttaaagca gcggcgtcaa aagtgaaggc taacttgcta tccgtagagg   7860
aagcttgcag cctgacgccc ccacactcag ccaaatccaa gtttggttat ggggcaaggg   7920
acgtccgttg ccatgccaga aaggccgtaa cccacatcaa ctccgtgtgg aaagaccttc   7980
```

```
tggaagacaa tgtaacacca atagacacta ccatcatggc taagaacgag gttttctgcg    8040
ttcagcctga gaaggggggt cgtaagccag ctcgtctcat cgtgttcccc gatctgggcg    8100
tgcgcgtgtg cgaaaagatg gctttgtacg acgtggttac caagctcccc ttggccgtga    8160
tgggaagctc ctacggattc caatactcac caggacagcg ggttgacttc ctcgtgcaag    8220
cgtggaagtc caagaaaacc ccaatgggggt tctcgtatga tacccgctgc tttgactcca    8280
cagtcactga gagcgacatc cgtacggagg aggcaatcta ccaatgttgt gacctcgacc    8340
cccaagcccg cgtggccatc aagtccctca ccgagaggct ttatgttggg ggccctctta    8400
ccaattcaag ggggggagaac tgcggctatc gcaggtgccg cgcgagcggc gtactgacaa    8460
ctagctgtgg taacacccctc acttgctaca tcaaggcccg ggcagcctgt cgagccgcag    8520
ggctccagga ctgcaccatg ctcgtgtgtg gcgacgactt agtcgttatc tgtgaaagcg    8580
cgggggtcca ggaggacgcg gcgagcctga gagccttcac ggaagctatg accaggtact    8640
ccgcccccccc cggggacccc ccacaaccag aatacgactt ggagctcata acatcatgct    8700
cctccaacgt gtcagtcgcc cacgacggcg ctggaaagag ggtctactac ctcacccgtg    8760
accctacaac cccccctcgcg agagctgcgt gggagacagc aagacacact ccagtcaatt    8820
cctggctagg caacataatc atgtttgccc ccacactgtg ggcgaggatg atactgatga    8880
cccatttctt tagcgtcctt atagccaggg accagcttga acaggccctc gattgcgaga    8940
tctacggggc ctgctactcc atagaaccac tggatctacc tccaatcatt caaagactcc    9000
atggcctcag cgcatttttca ctccacagtt actctccagg tgaaatcaat agggtggccg    9060
catgcctcag aaaacttggg gtaccgccct tgcgaacttg gagacaccgg gcccggagcg    9120
tccgcgctag gcttctggcc agaggaggca gggctgccat atgtggcaag tacctcttca    9180
actgggcagt aagaacaaag ctcaaactca ctccaatagc ggccgctggc cagctggact    9240
tgtccggctg gttcacggct ggctacagcg ggggaggcat ttttcacagc gtgtctcatg    9300
cccggccccg ctggttttgg tcttgcctac tcctgcttgc tgcaggggta ggcatctacc    9360
tcctccccaa ccgatgaagg ttggggtaaa cactccggcc tcttaggcca tttcctgttt    9420
tttttttttt ttgtttttttt tttttttttt tttttttttt tttttttttt tttttttttt    9480
ttttttttcc tttcctttttt tttttttttt ccctttttat ggtggctcca tcttagccct    9540
agtcacggct agctgtgaaa ggtccgtgag ccgcatgact gcagagagtg ctgatactgg    9600
cctctctgca gatcatgt                                                   9618

<210> SEQ ID NO 2
<211> LENGTH: 9618
<212> TYPE: DNA
<213> ORGANISM: Hepatitis C virus

<400> SEQUENCE: 2
gccagccccc tgatggggggc gacactccac catgaatcac tcccctgtga ggaactactg      60
tcttcacgca gaaagcgtct agccatggcg ttagtatgag tgtcgtgcag cctccaggac     120
ccccccctccc gggagagcca tagtggtctg cggaaccggt gagtacaccg gaattgccag     180
gacgaccggg tcctttcttg gataaaccccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gtcgcccaca ggacgtcaag ttcccgggtg     420
```

```
gcggtcagat cgttggtgga gtttacttgt tgccgcgcag gggccctaga ttgggtgtgc      480
gcgcgacgag gaagacttcc gagcggtcgc aacctcgagg tagacgtcag cctatcccca      540
aggcacgtcg gcccgagggc aggacctggg ctcagcccgg gtaccttgg  ccccctctatg     600 gcaatgaggg ctgcgggtgg gcgggatggc tcctgtctcc ccgtggctct cggcctagct      660
ggggccccac agaccccggg cgtaggtcgc gcaatttggg taaggtcatc gataccctta     720
cgtgcgcgtt cgccgacctc atggggtaca taccgctcgt cggcgcccct cttggaggcg      780
ctgccagggc cctggcgcat ggcgtccggg ttctggaaga cggcgtgaac tatgcaacag      840
ggaaccttcc tggttgctct ttctctatct tccttctggc cctgctctct tgcttgactg      900
tgcccgcttc ggcctaccaa gtgcgcaact ccacggggct ttaccacgtc accaatgatt      960
gccctaactc gagtattgtg tacgaggcgg ccgatgccat cctgcacact ccggggtgcg     1020
tcccttgcgt tcgcgagggc aacgcctcga ggtgttgggt ggcgatgacc cctacggtgg     1080
ccaccaggga tggcaaactc cccgcgacgc agcttcgacg tcacatcgat ctgcttgtcg     1140
ggagcgccac cctctgttcg gccctctacg tgggggacct gtgcgggtct gtctttcttg     1200
tcggccaact gttcaccttc tctcccaggc gccactggac gacgcaaggt tgcaattgct     1260
ctatctatcc cggtcatata acgggtcacc gcatggcatg gatatgatg  atgaactggt     1320 cccctacgac ggcgttggta atggctcagc tgctccgcat cccacaagcc atcttggaca     1380
tgatcgctgg tgctcactgg ggagtcctgg cgggcatagc gtatttctct atggtgggaa     1440
actgggcgaa ggtcctggta gtgctgctgc tatttgccgg cgtcgacgcg gaaacccacg     1500
tcaccggggg aagtgccggc cacactgtgt ctggatttgt tagcttcctc gcaccaggcg     1560
ccaagcagaa tgtccagctg atcaacacca acggcagttg gcacctcaat agcacggccc     1620
tgaactgcaa tgatagcctt aacaccggct ggttggcagg gcttttctat caccacaagt     1680
tcaactcttc aggctgccct gagaggctag ccagctgccg acccttacc gattttgacc      1740 agggctgggg ccctatcagt tatgccaacg gaagcggccc cgaccagcgc ccctactgct     1800
ggcactaccc cccaaaaacct tgcggtattg tgcccgcgaa gagtgtgtgt ggtccggtat     1860
attgcttcac tccagcccc  gtggtggtgg gaacgaccga caggtcgggc gcgcctacct     1920
acagctgggg tgaaaacgat acggacgttt tcgtccttaa caataccagg ccaccgctgg     1980
gcaattggtt cggttgtacc tggatgaact caactggatt caccaaagtg tgcggagcgc     2040
ctccttgtgt catcggaggg gcgggcaaca acaccctgca ctgccccact gattgcttcc     2100
gcaagcatcc ggacgccaca tactctcggt gcggctccgg tccctggatc acacccaggt     2160
gcctggtcga ttacccgtat aggctttggc attatccttg taccatcaac tacaccatat     2220
ttaaaattag gatgtacgtg gagggggtcg agcacaggct ggaagctgcc tgcaactgga     2280
cgcggggcga acgttgcgat ctggaagata gggacaggtc cgagctcagc ccgttactgc     2340
tgaccactac acagtggcag gtcctcccgt gttccttcac aaccctgcca gccttgtcca     2400
ccggcctcat ccacctccac cagaacattg tggacgtgca gtacttgtac ggggtggggt     2460
caagcatcgc gtcctgggcc attaagtggg agtacgtcgt tctcctgttc cttctgcttg     2520
cagacgcgcg cgtctgctcc tgcttgtgga tgatgctact catatcccaa gcggaggcgg     2580
ctttggagaa cctcgtaata cttaatgcag catccctggc cgggacgcac ggtcttgtat     2640
ccttcctcgt gttcttctgc tttgcatggt atctgaaggg taagtgggtg cccgagcgg     2700 tctacacctt ctacgggatg tggcctctcc tcctgctcct gttggcgttg ccccagcggg     2760
cgtacgcgct ggacacggag gtggccgcgt cgtgtggcgg tgttgttctc gtcgggttga     2820
```

```
tggcgctgac tctgtcacca tattacaagc gctatatcag ctggtgcttg tggtggcttc   2880
agtattttct gaccagagtg gaagcgcaac tgcacgtgtg gattcccccc ctcaacgtcc   2940
gagggggggcg cgacgccgtc atcttactca tgtgtgctgt acacccgact ctggtatttg   3000
acatcaccaa attgctgctg gccgtcttcg gaccccttg gattcttcaa gccagcttgc   3060
ttaaagtacc ctactttgtg cgcgtccaag gccttctccg gttctgcgcg ttagcgcgga   3120
agatggccgg aggccattac gtgcaaatgg tcatcattaa gttaggggcg cttactggca   3180
cctatgttta taaccacctc actcctcttc gggactgggc gcacaacggc ttgcgagatc   3240
tggccgtgac tgtagagcca gtcgtcttct cccaaatgga gaccaagctc atcacgtggg   3300
gggcagatac cgccgcgtgc ggtgacatca tcaacggctt gcctgtttcc gcccgcaggg   3360
gccgggagat actgctcggg ccagccgatg gaatggtctc caaggggtgg aggttgctgg   3420
cgcccatcac ggcgtacgcc cagcagacaa ggggcctcct agggtgcata atcaccagcc   3480
taactggccg ggacaaaaac caagtggagg gtgaggtcca gattgtgtca actgctgccc   3540
aaaccttcct ggcaacgtgc atcaatgggg tgtgctggac tgtctaccac ggggccggaa   3600
cgaggaccat cgcgtcaccc aagggtcctg tcatccagat gtataccaat gtagaccaag   3660
accttgtggg ctggcccgct ccgcaaggta gccgctcatt gacaccctgc acttgcggct   3720
cctcggacct ttacctggta acgaggcacg ccgatgtcat tcccgtgcgc cggcggggtg   3780
atagcagggg cagcctgctg tcgccccggc ccatttccta cttgaaaggc tcctcggggg   3840
gtccgctgtt gtgccccgcg gggcacgccg tgggtatatt tagggccgcg gtgtgcaccc   3900
gtggagtggc taaggcggtg gactttatcc ctgtggagaa cctagagaca accatgaggt   3960
ccccggtgtt cacggataac tcctctccac cagtagtgcc ccagagcttc caggtgggtc   4020
acctccatgc tcccacaggc agcggcaaaa gcaccaaggt cccggctgca tatgcagctc   4080
agggctataa ggtgctagta ctcaacccct ctgttgctgc aacactgggc tttggtgctt   4140
acatgtccaa ggctcatggg atcgatccta acatcaggac cggggtgaga acaattacca   4200
ctggcagccc catcacgtac tccacctacg gcaagttcct tgccgacggc gggtgctcgg   4260
ggggcgctta tgacgtaata atttgtgacg agtgccactc cacggatgcc acatccatct   4320
tgggcatcgg cactgtcctt gaccaagcag agactgcggg ggcgagactg gttgtgctcg   4380
ccaccgccac ccctccgggc tccgtcactg tgccccatcc caacatcgag gaggttgctc   4440
tgtccaccac cggagagatc cctttttacg gcaaggctat ccccctcgaa gtaatcaagg   4500
gggggagaca tctcatcttc tgtcattcaa agaagaagtg cgacgaactc gccgcaaagc   4560
tggtcgcatt gggcatcaat gccgtggcct actaccgcgg tcttgacgtg tccgtcatcc   4620
cgaccagcgg cgatgttgtc gtcgtggcaa ccgatgccct catgaccggc tataccggcg   4680
acttcgactc ggtgatagac tgcaatacgt gtgtcaccca gacagtcgat ctcagccttg   4740
accctacctt caccattgag acaatcacgc tccccccagga tgctgtctcc cgcactcaac   4800
gtcggggcag gactggcagg gggaagccag gcatctacag atttgtggca ccgggggagc   4860
gcccctctgg catgttcgac tcgtccgtcc tctgtgagtg ctatgacgca ggctgtgctt   4920
ggtatgagct cacgccgcc gagactacag ttaggctacg agcgtacatg aacacccgg   4980
ggcttcccgt gtgccaggac catcttgaat tttgggaggg cgtctttaca ggcctcactc   5040
atatagatgc ccactttcta tcccagacaa agcagagtgg ggagaacctt ccttacctgg   5100
tagcgtacca agccactgtg tgcgctaggg ctcaagcccc tccccccatcg tgggaccaga   5160
```

```
tgtggaagtg tttgattcgc ctcaagccca ccctccatgg gccaacaccc ctgctataca    5220
gactgggcgc tgttcagaat gaaatcaccc tgacgcaccc agtcaccaaa tacatcatga    5280
catgcatgtc ggccgacctg gaggtcgtca cgagcacctg ggtgctcgtt ggcggcgtcc    5340 tggctgctt  ggcctcgtat tgcctgtcaa caggctgcgt ggtcatagtg ggcagggtcg    5400
tcttgtccgg gaagccggca atcatacctg acagggaagt cctctaccaa gagttcgatg    5460
agatggaaga gtgctctcag cacttaccgt acatcgagca agggatgatg ctcgccgagc    5520
agttcaagca gaaggccctc ggcctcctgc agaccgcgtc ccgtcaggca gaggttatcg    5580
cccctgctgt ccagaccaac tggcaaaaac tcgagacctt ctgggcgaag catatgtgga    5640
acttcatcag tgggatacac tacttggcgg gcttgtcaac gctgcctggt aaccccgcca    5700
ttgcttcatt gatggctttt acagctgctg tcaccagccc actaaccact agccaaaccc    5760
tcctcttcaa catattgggg gggtgggtgg ctgcccagct cgccgccccc ggtgccgcta    5820
ctgcctttgt gggcgctggc ttagctggcg ccgccatcgg cagtgttgga ctggggaagg    5880
tcctcataga catccttgca gggtatgcgc gggcgtggc gggagctctt gtggcattca    5940
agatcatgag cggtgaggtc ccctccacgg aggacctggt caatctactg cccgccatcc    6000
tctcgcccgg agccctcgta gtcggcgtgg tctgtgcagc aatactgcgc cggcacgttg    6060
gcccgggcga gggggcagtg caatggatga accggctgat agccttcgcc tccggggga    6120 cccatgtttc ccccacgcac tacgtgccgg agagcgatgc agctgcccgc gtcactgcca    6180
tactcagcag cctcactgta acccagctcc tgaggcgact gcaccagtgg ataagctcgg    6240
agtgtaccac tccatgctcc ggttcctggc taagggacat ctgggactgg atatgcgagg    6300
tgttgagcga ctttaagacc tggctaaaag ctaagctcat gccacagctg cctgggatcc    6360
cctttgtgtc ctgccagcgc gggtataagg gggtctggcg aggggacggc atcatgcaca    6420
ctcgctgcca ctgtggagct gagatcactg acatgtcaa  aaacgggacg atgaggatcg    6480
tcggtcctag gacctgcagg aacatgtgga gtgggacctt ccccattaat gcctacacca    6540
cgggcccctg tacccccctt cctgcgccga actacacgtt cgcgctatgg agggtgtctg    6600
cagaggaata cgtggagata aggcaggtgg gggacttcca ctacgtgacg ggtatgacta    6660
ctgacaatct taaatgcccg tgccaggtcc atcgcccga  ttttttcaca gaattggacg    6720
gggtgcgcct acataggttt gcgcccccct gcaagccctt gctgcgggag gaggtatcat    6780
ttagagtagg actccacgaa tacccggtag gtcgcaatt  accttgcgag cccgaaccgg    6840
acgtggccgt gttgacgtcc atgctcactg atccctccca tataacagca gaggcggccg    6900
ggcggaggtt ggcgagggga tcacccccct ctgtggccag ctcctcggct agccagctat    6960
ccgctccatc tctcaaggca acttgcaccg ctaaccatga ctcccctgat gctgagctca    7020
tagaagccaa cctcctatgg aggcaggaga tgggcggcaa catcaccagg gttgagtcag    7080
aaaacaaagt ggtgattctg gactccttcg atccgcttgt ggcggaggag gacgagcggg    7140
agatctccgt acccgcagaa atcctgcgga agtctcggag attcgcccag ccctgcccg    7200 tttgggcgcg gccggactat aaccccccgc tagtggagac gtggaaaaag cccgactacg    7260
aaccacctgt ggtccatggc tgtccgcttc cacctccaaa gtcccctcct gtgcctccgc    7320
ctcggaagaa gcggacggtg gtcctcactg aatcaaccct atctactgcc ttggccgagc    7380
ttgccatcaa aagctttggc agctcctcaa cttccggcat tacgggcgac aatacgacaa    7440
catcctctga gcccgcccct tctgctgccc ccgcgactc  cgacgctgag tcctattcct    7500
ccatgccccc cctggagggg gagcctgggg atccggatct tagcgacggg tcatggtcaa    7560
```

-continued

```
cggtcagtag tgaggccagc gcggaggatg tcgtgcgctg ctcaatgtct tactcttgga    7620
caggcgcact cgtcaccccg tgcgccgcgg aagaacagaa actgcccatc aatgcactga    7680
gcaactcgtt gctacgtcac cacaacttgg tgtattccac cacctcacgc agtgcttgcc    7740
aaaggcagaa gaaagtcaca tttgacagac tgcaagttct ggacagccat taccaggacg    7800
tgctcaagga ggttaaagca gcggcgtcaa aagtgaaggc taacttgcta tccgtagagg    7860
aagcttgcag cctgacgccc ccacactcag ccaaatccaa gtttggttat ggggcaaagg    7920
acgtccgttg ccatgccaga aaggccgtaa cccacatcaa ctccgtgtgg aaagaccttc    7980
tggaagacaa tgtaacacca atagacacta ccatcatggc taagaacgag gttttctgcg    8040
ttcagcctga aaggggggt cgtaagccag ctcgtctcat cgtgttcccc gatctgggcg    8100
tgcgcgtgtg cgaaaagatg gctttgtacg acgtggttac caagctcccc ttggccgtga    8160
tgggaagctc ctacggattc caatactcac caggacagcg ggttgaattc ctcgtgcaag    8220
cgtggaagtc caagaaaacc ccaatggggt tctcgtatga tacccgctgc tttgactcca    8280
cagtcactga gagcgacatc cgtacggagg aggcaatcta ccaatgttgt gacctcgacc    8340
cccaagcccg cgtggccatc aagtccctca ccgagaggct ttatgttggg ggccctctta    8400
ccaattcaag gggggagaac tgcggctatc gcaggtgccg cgcgagcggc gtactgacaa    8460
ctagctgtgg taacaccctc acttgctaca tcaaggcccg ggcagcctgt cgagccgcag    8520
ggctccagga ctgcaccatg ctcgtgtgtg cgacgacttt agtcgttatc tgtgaaagcg    8580
cgggggtcca ggaggacgcg gcgagcctga gagccttcac ggaagctatg accaggtact    8640 ccgcccccc cggggacccc ccacaaccag aatacgactt ggagctcata acatcatgct    8700
cctccaacgt gtcagtcgcc cacgacggcg ctggaaagag ggtctactac ctcacccgtg    8760
accctacaac ccccctcgcg agagctgcgt gggagacagc aagacacact ccagtcaatt    8820
cctggctagg caacataatc atgtttgccc ccacactgtg ggcgaggatg atactgatga    8880
cccatttctt tagcgtcctt atagccaggg accagcttga acaggccctc gattgcgaga    8940
tctacggggc ctgctactcc atagaaccac tggatctacc tccaatcatt caaagactcc    9000
atggcctcag cgcattttca ctccacagtt actctccagg tgaaatcaat agggtggccg    9060
catgcctcag aaaacttggg gtaccgcct tgcgaacttg gagacaccgg cccggagcg    9120 tccgcgctag gcttctggcc agaggaggca gggctgccat atgtggcaag tacctcttca    9180
actgggcagt aagaacaaag ctcaaactca ctccaatagc ggccgctggc cagctggact    9240
tgtccggctg gttcacggct ggctacagcg ggggaggcat ttttcacagc gtgtctcatg    9300
cccggccccg ctggttttgg tcttgcctac tcctgcttgc tgcaggggta ggcatctacc    9360
tcctccccaa ccgatgaagg ttggggtaaa cactccggcc tcttaggcca tttcctgttt    9420
tttttttttt ttgtttttttt tttttttttt tttttttttt tttttttttt tttttttttt    9480
ttttttttcc tttcctttttt tttttttttt ccctttttat ggtggctcca tcttagccct    9540
agtcacggct agctgtgaaa ggtccgtgag ccgcatgact gcagagagtg ctgatactgg    9600
cctctctgca gatcatgt                                                  9618
```

<210> SEQ ID NO 3
<211> LENGTH: 9599
<212> TYPE: DNA
<213> ORGANISM: Hepatitis C virus

<400> SEQUENCE: 3

```
gccagccccc tgatggggc gacactccac catgaatcac tccctgtga ggaactactg      60
tcttcacgca gaaagcgtct agccatggcg ttagtatgag tgtcgtgcag cctccaggac    120
cccccctccc gggagagcca tagtggtctg cggaaccggt gagtacaccg gaattgccag    180
gacgaccggg tcctttcttg gataaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gtcgcccaca ggacgtcaag ttcccgggtg    420
gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtaccttgg cccctctatg     600
gcaatgaggg ttgcgggtgg gcgggatggc tcctgtctcc ccgtggctct cggcctagct    660
ggggccccac agaccccgg cgtaggtcgc gcaatttggg taaggtcatc gatacccta      720
cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaactc gagtattgtg tacgaggcgg ccgatgccat cctgcacact ccgggggtgtg  1020
tcccttgcgt tcgcgagggt aacgcctcga ggtgttgggt ggcggtgacc cccacggtgg   1080
ccaccaggga cggcaaactc cccacaacgc agcttgacg tcatatcgat ctgcttgtcg    1140
ggagcgccac cctctgctcg gccctctacg tggggacct gtgcgggtct gtctttcttg    1200
ttggtcaact gtttaccttc tctcccaggc gccactggac gacgcaagac tgcaattgtt   1260
ctatctatcc cggccatata acgggtcatc gcatggcatg ggatatgatg atgaactggt   1320
cccctacggg agcgttggtg gtagctcagc tgctccggat cccacaagcc atcacggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aaatgccggc cgcaccacgg ctgggcttgt tggtctcctt acaccaggcg   1560
ccaagcagaa catccaactg atcaacacca acggcagttg gcacatcaat agcacggcct   1620
tgaattgcaa tgaaagcctt aacaccggct ggttagcagg gctcttctat caacacaaat   1680
tcaactcttc aggctgtcct gagaggttgg ccagctgccg acgccttacc gattttgccc   1740
agggctgggg tcctatcagt tatgccaacg gaagcggcct cgacgaacgc ccctactgct   1800
ggcactaccc tccaagacct tgtggcattg tgccgcaaa gagcgtgtgt ggccggtat     1860
attgcttcac tcccagcccc gtggtggtgg gaacgaccga caggtcgggc gcgcctacct   1920
acagctgggg tgcaaatgat acggatgtct tcgtccttaa caacaccagg ccaccgctgg   1980
gcaattggtt cggttgtacc tggatgaact caactggatt caccaaagtg tgcggagcgc   2040
ccccttgtgt catcggaggg gtgggcaaca cacccttgct ctgccccact gattgcttcc   2100
gcaaacatcc ggaagccaca tactctcggt gcggctccgg tcctggatt acacccaggt    2160
gcatggtcga ctaccgtat aggctttggc actatccttg taccatcaat tacaccatat    2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
```

```
ccggcctcat ccacctccac cagaacattg tggacgtgca gtacttgtac ggggtagggt    2460
caagcatcgc gtcctgggcc attaagtggg agtacgtcgt tctcctgttc cttctgcttg    2520
cagacgcgcg cgtctgctcc tgcttgtgga tgatgttact catatcccaa gcggaggcgg    2580
cttttggaga acctcgtaat actcaatgca gcatccctgg ccggacgcac ggtcttgtgt    2640
ccttcctcgt gttcttctgc tttgcgtggt atctgaaggg taggtgggtg cccggagcgg    2700
tctacgccct ctacgggatg tggcctctcc tcctgctcct gctggcgttg cctcagcggg    2760
catacgcact ggacacggag gtggccgcgt cgtgtggcgg cgttgttctt gtcgggttaa    2820
tggtgctgac tctgtcgcca tattacaagc gctatatcag ctggtgcatg tggtggcttc    2880
agtattttct gaccagagta gaagcgcaac tgcacgtgtg ggttcccccc cgcaacgtcc    2940
ggggggggcg cgatgccgtc atcttactca tgtgtgtagt acacccgacc ctggtatttg    3000
acatcaccaa actactcctg gccatcttcg gaccccttg gattcttcaa gccagttttgc    3060 ttaaagtccc ctacttcgtg cgcgttcaag gccttctccg gatctgcgcg ctagcgcgga    3120
agatagccgg aggtcattac gtgcaaatgg ccatcatcaa gttagggggcg cttactggca    3180 cctatgtgta taaccatctc acccctcttc gagactgggc gcacaacggc ctgcgagatc    3240
tggccgtggc tgtggaacca gtcgtcttct cccgaatgga gaccaagctc atcacgtggg    3300
gggcagatac cgccgcgtgc ggtgacatca tcaacggctt gcccgtctct gcccgtaggg    3360
gccaggagat actgcttggg ccagccgacg gaatggtctc aaggggtgg aggttgctgg    3420 cgcccatcac ggcgtacgcc cagcagacga gaggcctcct agggtgtata atcaccagcc    3480
tgactggccg ggacagaaac caagtggagg gtgaggtcca gatcgtgtca actgctaccc    3540
aaaccttcct ggcaacgtgc atcaatgggg tatgctggac tgtctaccac ggggccggaa    3600
cgaggaccat cgcatcaccc aagggtcctg tcatccagat gtataccaat gtggaccaag    3660
accttgtggg ctggccccgct cctcaaggtt cccgctcatt gacaccctgt acctgcggct    3720
cctcggacct ttacctggtc acgaggcacg ccgatgtcat tcccgtgcgc cggcgaggtg    3780
atagcagggg tagcctgctt tcgccccggc ccatttccta cttgaaaggc tcctcggggg    3840
gtccgctgtt gtgccccgcg ggacacgccg tgggcctatt cagggccgcg gtgtgcaccc    3900
gtggagtggc taaagcggtg gactttatcc ctgtggagaa cctagggaca accatgagat    3960
ccccggtgtt cacggacaac tcctctccac cagcagtgcc ccagagcttc caggtgggcc    4020
acctgcatgc tcccaccggc agcggtaaga gcaccaaggt cccggctgcg tacgcagccc    4080
agggctacaa ggtgttggtg ctcaacccct ctgttgctgc aacgctgggc tttggtgctt    4140
acatgtccaa ggcccatggg gttgatccta atatcaggac cggggtgaga acaattacca    4200
ctggcagccc catcacgtac tccacctacg gcaagttcct tgccgacggc gggtgctcag    4260
gaggtgctta tgacataata atttgtgacg agtgccactc cacggatgcc acatccatct    4320
tgggcatcgg cactgtcctt gaccaagcag agactgcggg ggcgagactg gttgtgctcg    4380
ccactgctac ccctccgggc tccgtcactg tgtcccatcc taacatcgag gaggttgctc    4440
tgcccaccac cggagagatc cccttttacg gcaaggctat cccccctcgag gtgatcaagg    4500 ggggaagaca tctcatcttc tgccactcaa agaagaagtg cgacgagctc gccgcgaagc    4560
tggtcgcatt gggcatcaat gccgtggcct actaccgcgg tcttgacgtg tctgtcatcc    4620
cgaccagcgg cgatgttgtc gtcgtgtcga ccgatgctct catgactggc tttaccggcg    4680
acttcgactc tgtgatagac tgcaacacgt gtgtcactca gacagtcgat ctcagccttg    4740
```

| | | | | |
|---|---|---|---|---|
| accctacctt | taccattgag | acaaccacgc | tccccagga | tgctgtctcc aggactcaac | 4800 |
| gccggggcag | gactggcagg | gggaagccag | gcatctatag | atttgtggca ccggggagc | 4860 |
| gcccctccgg | catgttcgac | tcgtccgtcc | tctgtgagtg | ctatgacgcg ggctgtgctt | 4920 |
| ggtatgagct | cacgcccgcc | gagactacag | ttaggctacg | agcgtacatg aacaccccgg | 4980 |
| ggcttcccgt | gtgccaggac | catcttgaat | tttgggaggg | cgtctttacg ggcctcactc | 5040 |
| atatagatgc | ccactttta | tcccagacaa | agcagagtgg | ggagaacttt ccttacctgg | 5100 |
| tagcgtacca | agccaccgtg | tgcgctaggg | ctcaagcccc | tccccatcg tgggaccaga | 5160 |
| tgtggaagtg | tttgatccgc | cttaaaccca | ccctccatgg | gccaacaccc ctgctataca | 5220 |
| gactgggcgc | tgttcagaat | gaagtcaccc | tgacgcaccc | aatcaccaaa tacatcatga | 5280 |
| catgcatgtc | ggccgacctg | gaggtcgtca | cgagcacctg | ggtgctcgct ggcggcgtcc | 5340 |
| tggctgctct | ggcctcgtat | tgcctgtcaa | caggctgcgt | ggtcatagtg ggcaggatcg | 5400 |
| tcttgtccgg | gaagccggca | attataccctg | acagggaggt | tctctaccag gagttcgatg | 5460 |
| agatggaaga | gtgctctcag | cacttaccgt | acatcgagca | agggatgatg ctcgctgagc | 5520 |
| agttcaagca | gaaggccctc | ggcctcctgc | agaccgcgtc | ccgccatgca gaggttatca | 5580 |
| cccctgctgt | ccagaccaac | tggcagaaac | tcgaggtctt | ttgggcgaag cacatgtgga | 5640 |
| atttcatcag | tgggatacac | tacttggcgg | gcctgtcaac | gctgcctggt aaccccgcca | 5700 |
| ttgcttcatt | gatggctttt | acagctgccg | tcaccagccc | actaaccact ggccaaaccc | 5760 |
| tcctcttcaa | catattgggg | gggtgggtgg | ctgcccagct | cgccgccccc ggtgccgcta | 5820 |
| ctgcctttgt | gggtgctggc | ctagctggcg | ccgccatcgg | cagcgttgga ctggggaagg | 5880 |
| tcctcgtgga | cattcttgca | gggtatggcg | cgggcgtggc | gggagctctt gtagcattca | 5940 |
| agatcatgag | cggtgaggtc | ccctccacgag | aggacctggt | caatctgctg cccgccatcc | 6000 |
| tctcgcctgg | agcccttgta | gtcggtgtgg | tctgcgcagc | aatactgcgc cggcacgttg | 6060 |
| gcccgagcga | gggggcagtg | caatggatga | accggctaat | agccttcgcc tcccggggga | 6120 |
| cccatgtttc | ccccacgcac | tacgtgccgg | agagcgatgc | agccgcccgc gtcactgcca | 6180 |
| tactcagcag | cctcactgta | acccagctcc | tgaggcgact | gcatcagtgg ataagctcgg | 6240 |
| agtgtaccac | tccatgctcc | ggttcctggc | taagggacat | ctgggactgg atatgcgagg | 6300 |
| tgctgagcga | ctttaagacc | tggctgaaag | ccaagctcat | gccacaactg cctgggattc | 6360 |
| cctttgtgtc | ctgccagcgc | gggtataggg | gggtctggcg | aggagacggc attatgcaca | 6420 |
| ctcgctgcca | ctgtggagct | gagatcactg | gacatgtcaa | aaacgggacg atgaggatcg | 6480 |
| tcggtcctag | gacctgcagg | aacatgtgga | gtgggacgtt | ccccattaac gcctacacca | 6540 |
| cgggcccctg | tactcccctt | cctgcgccga | actataagtt | cgcgctgtgg agggtgtctg | 6600 |
| cagaggaata | cgtggagata | aggcgggtgg | gggacttcca | ctacgtatcg ggtgtgacta | 6660 |
| ctgacaatct | taaatgcccg | tgccagatcc | catcgcccga | atttttcaca gaattggacg | 6720 |
| gggtgcgcct | acacaggttt | gcgccccctt | gcaagccctt | gctgcgggag gaggtatcat | 6780 |
| tcagagtagg | actccacgag | tacccggtgg | ggtcgcaatt | accttgcgag cccgaaccgg | 6840 |
| acgtagccgt | gttgacgtcc | atgctcactg | atccctccca | tataacagca gaggcggccg | 6900 |
| ggagaaggtt | ggcgagaggg | tcacccccctt | ctatggccag | ctcctcggct agccagctgt | 6960 |
| ccgctccatc | tctcaaggca | acttgcaccg | ccaaccatga | ctcccctgac gccgagctca | 7020 |
| tagaggctaa | cctcctgtgg | aggcaggaga | tgggcggcaa | catcaccagg gttgagtcag | 7080 |
| agaacaaagt | ggtgattctg | gactccttcg | atccgcttgt | ggcagaggag gatgagcggg | 7140 |

```
aggtctccgt acctgcagaa attctgcgga agtctcggag attcgcccgg gccctgcccg    7200
tctgggcgcg gccggactac aaccccccgc tagtagagac gtggaaaaag cctgactacg    7260
aaccacctgt ggtccatggc tgcccgctac cacctccacg gtccctcct gtgcctccgc     7320
ctcggaaaaa gcgtacggtg gtcctcaccg aatcaaccct atctactgcc ttggccgagc    7380
ttgccaccaa aagttttggc ggctcctcaa cttccggcat tacgggcgac aatacgacaa    7440
catcctctga gcccgcccct tctggctgcc ccccgactc cgacgttgag tcctattctt     7500
ccatgccccc cctggagggg gagcctgggg atccggatct cagcgacggg tcatggtcga    7560
cggtcagtag tggggccgac acggaagatg ccgtgtgctg ctcaatgtct tattcctgga    7620
caggcgcact catcaccccg tgcgctgcgg aagaacaaaa actgcccatc aacgcactga    7680
gcaactcgtt gctacgccat cacaatctgg tgtattccac cacttcacgc agtgcttgcc    7740
aaaggcagaa gaaagtcaca tttgacagac tgcaagttct ggacagccat taccaggacg    7800
tgctcaagga ggtcaaagca gcggcgtcaa aagtgaaggc taacttgcta tccgtagagg    7860
aagcttgcag cctgacgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
ttcagcctga gaaggggggt cgtaagccag ctcgtctcat cgtgttcccc gacctgggcg    8100
tgcgcgtgtg cgagaagatg gccctgtacg acgtggttag caagctcccc ctggccgtga    8160
tgggaagctc ctacggattc caatactcac caggacagcg ggttgaattc ctcgtgcaag    8220
cgtggaagtc caagaagacc ccgatggggt tctcgtatga tacccgctgt tttgactcca    8280
cagtcactga gagcgacatc cgtacggagg aggcaattta ccaatgttgt gacctggacc    8340
cccaagcccg cgtggccatc aagtccctca ctgagaggct ttatgttggg ggccctctta    8400
ccaattcaag gggggaaaac tgcggctacc gcaggtgccg cgcgagcggc gtactgacaa    8460
ctagctgtgg taacaccctc acttgctaca tcaaggcccg ggcagcctgt cgagccgcag    8520
ggctccagga ctgcaccatg ctcgtgtgtg gcgacgactt agtcgttatc tgtgaaagtg    8580
cgggggtcca ggaggacgcg gcgagcctga gagccttcac ggaggctatg accaggtact    8640
ccgccccccc cggggacccc ccacaaccag aatacgactt ggagcttata acatcatgct    8700
cctccaacgt gtcagtcgcc cacgacgcg ctggaaagag ggtctactac cttacccgtg     8760
accctacaac ccccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggctctt aactgtgaga    8940
tctacggagc ctgctactcc atagaaccac tggatctacc tccaatcatt caaagactcc    9000
atggcctcag cgcattttca ctccacagtt actctccagg tgaaatcaat agggtggccg    9060
catgcctcag aaaacttggg gtcccgcct tgcgagcttg gagacaccgg gcccggagcg     9120
tccgcgctag gcttctgtcc agaggaggca gggctgccat atgtggcaag tacctcttca    9180
actgggcagt aagaacaaag ctcaaactca ctccaatagc ggccgctggc cggctggact    9240
tgtccggttg gttcacggct ggctacagcg ggggaggcat ttttcacagc gtgtctcatg    9300
cccggccccg ctggttctgg cgttgcctac tcctgctcgc tgcaggggta ggcatctacc    9360
tcctccccaa ccgatgaagg ttggggtaaa cactccggcc tcttaagcca tttcctgttt    9420
ttttttttt tttttttttt ttttttcttt ttttttttctt tcctttcctt ctttttttcc    9480
```

```
tttctttttc ccttctttaa tggtggctcc atcttagccc tagtcacggc tagctgtgaa      9540
aggtccgtga ccgcatgac tgcagagagt gctgatactg gcctctctgc agatcatgt       9599
```

<210> SEQ ID NO 4
<211> LENGTH: 3011
<212> TYPE: PRT
<213> ORGANISM: Hepatitis C virus
<400> SEQUENCE: 4

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
```

```
                355                 360                 365
Ala Lys Val Leu Val Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Phe Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Thr Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
    770                 775                 780
```

```
Gly Ala Val Tyr Thr Phe Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
        835                 840                 845

Phe Leu Thr Arg Val Glu Ala Gln Leu His Val Trp Ile Pro Pro Leu
850                 855                 860

Asn Val Arg Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
        915                 920                 925

Ala Gly Gly His Tyr Val Gln Met Val Ile Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Thr Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                 1000                1005

Glu Ile Leu Leu Gly Pro Ala Asp Gly Met Val Ser Lys Gly Trp Arg
1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
        1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
        1155                1160                1165

Leu Leu Cys Pro Ala Gly His Ala Val Gly Ile Phe Arg Ala Ala Val
    1170                1175                1180

Cys Thr Arg Gly Val Ala Lys Ala Val Asp Phe Ile Pro Val Glu Asn
1185                1190                1195                1200
```

```
Leu Glu Thr Thr Met Arg Ser Pro Val Phe Thr Asp Asn Ser Ser Pro
            1205                1210                1215

Pro Val Pro Gln Ser Phe Gln Val Gly His Leu His Ala Pro Thr
1220                1225                1230

Gly Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ser Pro Ile Thr Tyr Ser Thr Tyr
            1285                1290                1295

Gly Lys Phe Leu Ala Asp Gly Gly Cys Ser Gly Gly Ala Tyr Asp Val
        1300                1305                1310

Ile Ile Cys Asp Glu Cys His Ser Thr Asp Ala Thr Ser Val Leu Gly
    1315                1320                1325

Ile Gly Thr Val Leu Asp Gln Ala Glu Thr Ala Gly Ala Arg Leu Val
    1330                1335                1340

Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
            1365                1370                1375

Gly Lys Ala Ile Pro Leu Glu Val Ile Lys Gly Gly Arg His Leu Ile
        1380                1385                1390

Phe Cys His Ser Lys Lys Lys Cys Asp Glu Leu Ala Ala Lys Leu Val
    1395                1400                1405

Ala Leu Gly Ile Asn Ala Val Ala Tyr Tyr Arg Gly Leu Asp Val Ser
    1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Cys Asn Thr
            1445                1450                1455

Cys Val Thr Gln Thr Val Asp Leu Ser Leu Asp Pro Thr Phe Thr Ile
        1460                1465                1470

Glu Thr Ile Thr Leu Pro Gln Asp Ala Val Ser Arg Thr Gln Arg Arg
    1475                1480                1485

Gly Arg Thr Gly Arg Gly Lys Pro Gly Ile Tyr Arg Phe Val Ala Pro
    1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
        1540                1545                1550

Asp His Leu Glu Phe Trp Glu Gly Val Phe Thr Gly Leu Thr His Ile
    1555                1560                1565

Asp Ala His Phe Leu Ser Gln Thr Lys Gln Ser Gly Glu Asn Leu Pro
    1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
```

```
                    1620            1625            1630
Asn Glu Ile Thr Leu Thr His Pro Val Thr Lys Tyr Ile Met Thr Cys
            1635            1640            1645

Met Ser Ala Asp Leu Glu Val Val Thr Ser Thr Trp Val Leu Val Gly
        1650            1655            1660

Gly Val Leu Ala Ala Leu Ala Ser Tyr Cys Leu Ser Thr Gly Cys Val
1665            1670            1675            1680

Val Ile Val Gly Arg Val Val Leu Ser Gly Lys Pro Ala Ile Ile Pro
            1685            1690            1695

Asp Arg Glu Val Leu Tyr Gln Glu Phe Asp Glu Met Glu Glu Cys Ser
        1700            1705            1710

Gln His Leu Pro Tyr Ile Glu Gln Gly Met Met Leu Ala Glu Gln Phe
    1715            1720            1725

Lys Gln Lys Ala Leu Gly Leu Leu Gln Thr Ala Ser Arg Gln Ala Glu
        1730            1735            1740

Val Ile Ala Pro Ala Val Gln Thr Asn Trp Gln Lys Leu Glu Thr Phe
1745            1750            1755            1760

Trp Ala Lys His Met Trp Asn Phe Ile Ser Gly Ile His Tyr Leu Ala
            1765            1770            1775

Gly Leu Ser Thr Leu Pro Gly Asn Pro Ala Ile Ala Ser Leu Met Ala
        1780            1785            1790

Phe Thr Ala Ala Val Thr Ser Pro Leu Thr Thr Ser Gln Thr Leu Leu
        1795            1800            1805

Phe Asn Ile Leu Gly Gly Trp Val Ala Ala Gln Leu Ala Ala Pro Gly
        1810            1815            1820

Ala Ala Thr Ala Phe Val Gly Ala Gly Leu Ala Gly Ala Ala Ile Gly
1825            1830            1835            1840

Ser Val Gly Leu Gly Lys Val Leu Ile Asp Ile Leu Ala Gly Tyr Gly
            1845            1850            1855

Ala Gly Val Ala Gly Ala Leu Val Ala Phe Lys Ile Met Ser Gly Glu
        1860            1865            1870

Val Pro Ser Thr Glu Asp Leu Val Asn Leu Leu Pro Ala Ile Leu Ser
        1875            1880            1885

Pro Gly Ala Leu Val Val Gly Val Val Cys Ala Ala Ile Leu Arg Arg
    1890            1895            1900

His Val Gly Pro Gly Glu Gly Ala Val Gln Trp Met Asn Arg Leu Ile
1905            1910            1915            1920

Ala Phe Ala Ser Arg Gly Thr His Val Ser Pro Thr His Tyr Val Pro
            1925            1930            1935

Glu Ser Asp Ala Ala Ala Arg Val Thr Ala Ile Leu Ser Ser Leu Thr
        1940            1945            1950

Val Thr Gln Leu Leu Arg Arg Leu His Gln Trp Ile Ser Ser Glu Cys
        1955            1960            1965

Thr Thr Pro Cys Ser Gly Ser Trp Leu Arg Asp Ile Trp Asp Trp Ile
    1970            1975            1980

Cys Glu Val Leu Ser Asp Phe Lys Thr Trp Leu Lys Ala Lys Leu Met
1985            1990            1995            2000

Pro Gln Leu Pro Gly Ile Pro Phe Val Ser Cys Gln Arg Gly Tyr Lys
        2005            2010            2015

Gly Val Trp Arg Gly Asp Gly Ile Met His Thr Arg Cys His Cys Gly
            2020            2025            2030

Ala Glu Ile Thr Gly His Val Lys Asn Gly Thr Met Arg Ile Val Gly
        2035            2040            2045
```

```
Pro Arg Thr Cys Arg Asn Met Trp Ser Gly Thr Phe Pro Ile Asn Ala
        2050                2055                2060

Tyr Thr Thr Gly Pro Cys Thr Pro Leu Pro Ala Pro Asn Tyr Thr Phe
2065                2070                2075                2080

Ala Leu Trp Arg Val Ser Ala Glu Glu Tyr Val Glu Ile Arg Gln Val
                2085                2090                2095

Gly Asp Phe His Tyr Val Thr Gly Met Thr Thr Asp Asn Leu Lys Cys
            2100                2105                2110

Pro Cys Gln Val Pro Ser Pro Glu Phe Phe Thr Glu Leu Asp Gly Val
            2115                2120                2125

Arg Leu His Arg Phe Ala Pro Pro Cys Lys Pro Leu Leu Arg Glu Glu
        2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
            2180                2185                2190

Gly Ser Pro Pro Ser Ala Ala Ser Ser Ser Ala Ser Gln Leu Ser Ala
        2195                2200                2205

Pro Ser Leu Lys Ala Thr Cys Thr Ala Asn His Asp Ser Pro Asp Ala
        2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Asp Pro Leu Val Ala Glu Asp Glu Arg Glu Thr Ser Val Pro Ala
            2260                2265                2270

Glu Ile Leu Arg Lys Ser Arg Arg Phe Ala Gln Ala Leu Pro Val Trp
        2275                2280                2285

Ala Arg Pro Asp Tyr Asn Pro Pro Leu Val Glu Thr Trp Lys Lys Pro
        2290                2295                2300

Asp Tyr Glu Pro Pro Val Val His Gly Cys Pro Leu Pro Pro Lys
2305                2310                2315                2320

Ser Pro Pro Val Pro Pro Arg Lys Lys Arg Thr Val Val Leu Thr
            2325                2330                2335

Glu Ser Thr Leu Ser Thr Ala Leu Ala Glu Leu Ala Ile Lys Ser Phe
            2340                2345                2350

Gly Ser Ser Ser Thr Ser Gly Ile Thr Gly Asp Asn Thr Thr Thr Ser
        2355                2360                2365

Ser Glu Pro Ala Pro Ser Gly Cys Pro Arg Asp Ser Asp Ala Glu Ser
        2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Glu Ala Ser Ala Glu Asp
            2405                2410                2415

Val Val Arg Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
        2435                2440                2445

Ser Leu Leu Arg His His Asn Leu Val Tyr Ser Thr Thr Ser Arg Ser
        2450                2455                2460
```

```
Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ser
            2485                2490                2495

Lys Val Lys Ala Asn Leu Leu Ser Val Glu Glu Ala Cys Ser Leu Thr
                2500                2505                2510

Pro Pro His Ser Ala Lys Ser Lys Phe Gly Tyr Gly Ala Lys Asp Val
            2515                2520                2525

Arg Cys His Ala Arg Lys Ala Val Thr His Ile Asn Ser Val Trp Lys
            2530                2535                2540

Asp Leu Leu Glu Asp Asn Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
            2580                2585                2590

Met Ala Leu Tyr Asp Val Val Thr Lys Leu Pro Leu Ala Val Met Gly
        2595                2600                2605

Ser Ser Tyr Gly Phe Gln Tyr Ser Pro Gly Gln Arg Val Asp Phe Leu
2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
        2660                2665                2670

Ile Lys Ser Leu Thr Glu Arg Leu Tyr Val Gly Gly Pro Leu Thr Asn
            2675                2680                2685

Ser Arg Gly Glu Asn Cys Gly Tyr Arg Arg Cys Arg Ala Ser Gly Val
2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
            2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
            2835                2840                2845

Phe Phe Ser Val Leu Ile Ala Arg Asp Gln Leu Glu Gln Ala Leu Asp
        2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
```

```
                        2885                2890                2895
Tyr Ser Pro Gly Glu Ile Asn Arg Val Ala Ala Cys Leu Arg Lys Leu
            2900                2905                2910
Gly Val Pro Pro Leu Arg Thr Trp Arg His Arg Ala Arg Ser Val Arg
            2915                2920                2925
Ala Arg Leu Leu Ala Arg Gly Gly Arg Ala Ala Ile Cys Gly Lys Tyr
            2930                2935                2940
Leu Phe Asn Trp Ala Val Arg Thr Lys Leu Lys Leu Thr Pro Ile Ala
2945                2950                2955                2960
Ala Ala Gly Gln Leu Asp Leu Ser Gly Trp Phe Thr Ala Gly Tyr Ser
            2965                2970                2975
Gly Gly Gly Ile Phe His Ser Val Ser His Ala Arg Pro Arg Trp Phe
            2980                2985                2990
Trp Ser Cys Leu Leu Leu Leu Ala Ala Gly Val Gly Ile Tyr Leu Leu
            2995                3000                3005
Pro Asn Arg
      3010

<210> SEQ ID NO 5
<211> LENGTH: 3011
<212> TYPE: PRT
<213> ORGANISM: Hepatitis C virus

<400> SEQUENCE: 5

Met Ser Thr Asn Pro Lys Pro Gln Arg Lys Thr Lys Arg Asn Thr Asn
1               5                   10                  15
Arg Arg Pro Gln Asp Val Lys Phe Pro Gly Gly Gly Gln Ile Val Gly
            20                  25                  30
Gly Val Tyr Leu Leu Pro Arg Arg Gly Pro Arg Leu Gly Val Arg Ala
        35                  40                  45
Thr Arg Lys Thr Ser Glu Arg Ser Gln Pro Arg Gly Arg Arg Gln Pro
    50                  55                  60
Ile Pro Lys Ala Arg Arg Pro Glu Gly Arg Thr Trp Ala Gln Pro Gly
65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Thr Asp Pro
            100                 105                 110
Arg Arg Arg Ser Arg Asn Leu Gly Lys Val Ile Asp Thr Leu Thr Cys
        115                 120                 125
Gly Phe Ala Asp Leu Met Gly Tyr Ile Pro Leu Val Gly Ala Pro Leu
    130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Tyr
            180                 185                 190
Gln Val Arg Asn Ser Thr Gly Leu Tyr His Val Thr Asn Asp Cys Pro
        195                 200                 205
Asn Ser Ser Ile Val Tyr Glu Ala Ala Asp Ala Ile Leu His Thr Pro
    210                 215                 220
Gly Cys Val Pro Cys Val Arg Glu Gly Asn Ala Ser Arg Cys Trp Val
225                 230                 235                 240
```

```
Ala Met Thr Pro Thr Val Ala Thr Arg Asp Gly Lys Leu Pro Ala Thr
            245                 250                 255
Gln Leu Arg Arg His Ile Asp Leu Leu Val Gly Ser Ala Thr Leu Cys
        260                 265                 270
Ser Ala Leu Tyr Val Gly Asp Leu Cys Gly Ser Val Phe Leu Val Gly
            275                 280                 285
Gln Leu Phe Thr Phe Ser Pro Arg Arg His Trp Thr Thr Gln Gly Cys
    290                 295                 300
Asn Cys Ser Ile Tyr Pro Gly His Ile Thr Gly His Arg Met Ala Trp
305                 310                 315                 320
Asp Met Met Met Asn Trp Ser Pro Thr Thr Ala Leu Val Met Ala Gln
                325                 330                 335
Leu Leu Arg Ile Pro Gln Ala Ile Leu Asp Met Ile Ala Gly Ala His
            340                 345                 350
Trp Gly Val Leu Ala Gly Ile Ala Tyr Phe Ser Met Val Gly Asn Trp
        355                 360                 365
Ala Lys Val Leu Val Val Leu Leu Phe Ala Gly Val Asp Ala Glu
    370                 375                 380
Thr His Val Thr Gly Gly Ser Ala Gly His Thr Val Ser Gly Phe Val
385                 390                 395                 400
Ser Phe Leu Ala Pro Gly Ala Lys Gln Asn Val Gln Leu Ile Asn Thr
                405                 410                 415
Asn Gly Ser Trp His Leu Asn Ser Thr Ala Leu Asn Cys Asn Asp Ser
            420                 425                 430
Leu Asn Thr Gly Trp Leu Ala Gly Leu Phe Tyr His His Lys Phe Asn
        435                 440                 445
Ser Ser Gly Cys Pro Glu Arg Leu Ala Ser Cys Arg Pro Leu Thr Asp
    450                 455                 460
Phe Asp Gln Gly Trp Gly Pro Ile Ser Tyr Ala Asn Gly Ser Gly Pro
465                 470                 475                 480
Asp Gln Arg Pro Tyr Cys Trp His Tyr Pro Lys Pro Cys Gly Ile
                485                 490                 495
Val Pro Ala Lys Ser Val Cys Gly Pro Val Tyr Cys Phe Thr Pro Ser
            500                 505                 510
Pro Val Val Gly Thr Thr Asp Arg Ser Gly Ala Pro Thr Tyr Ser
        515                 520                 525
Trp Gly Glu Asn Asp Thr Asp Val Phe Val Leu Asn Asn Thr Arg Pro
    530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Gly Ala Gly Asn
                565                 570                 575
Asn Thr Leu His Cys Pro Thr Asp Cys Phe Arg Lys His Pro Asp Ala
            580                 585                 590
Thr Tyr Ser Arg Cys Gly Ser Gly Pro Trp Ile Thr Pro Arg Cys Leu
        595                 600                 605
Val Asp Tyr Pro Tyr Arg Leu Trp His Tyr Pro Cys Thr Ile Asn Tyr
    610                 615                 620
Thr Ile Phe Lys Ile Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
                645                 650                 655
Arg Asp Arg Ser Glu Leu Ser Pro Leu Leu Leu Thr Thr Thr Gln Trp
```

```
                    660                 665                 670
Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ser Ile Ala Ser Trp Ala Ile Lys Trp Glu Tyr Val Val
705                 710                 715                 720

Leu Leu Phe Leu Leu Ala Asp Ala Arg Val Cys Ser Cys Leu Trp
            725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Lys Trp Val Pro
            770                 775                 780

Gly Ala Val Tyr Thr Phe Tyr Gly Met Trp Pro Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
            835                 840                 845

Phe Leu Thr Arg Val Glu Ala Gln Leu His Val Trp Ile Pro Pro Leu
            850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
            885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
            915                 920                 925

Ala Gly Gly His Tyr Val Gln Met Val Ile Ile Lys Leu Gly Ala Leu
            930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Thr Val Glu Pro Val Val Phe
            965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
            995                 1000                1005

Glu Ile Leu Leu Gly Pro Ala Asp Gly Met Val Ser Lys Gly Trp Arg
            1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
            1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
            1075                1080                1085
```

-continued

```
Thr Ile Ala Ser Pro Lys Gly Pro Val Ile Gln Met Tyr Thr Asn Val
    1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
                1125                1130                1135
Ala Asp Val Ile Pro Val Arg Arg Arg Gly Asp Ser Arg Gly Ser Leu
            1140                1145                1150
Leu Ser Pro Arg Pro Ile Ser Tyr Leu Lys Gly Ser Ser Gly Gly Pro
        1155                1160                1165
Leu Leu Cys Pro Ala Gly His Ala Val Gly Ile Phe Arg Ala Ala Val
    1170                1175                1180
Cys Thr Arg Gly Val Ala Lys Ala Val Asp Phe Ile Pro Val Glu Asn
1185                1190                1195                1200
Leu Glu Thr Thr Met Arg Ser Pro Val Phe Thr Asp Asn Ser Ser Pro
                1205                1210                1215
Pro Val Val Pro Gln Ser Phe Gln Val Gly His Leu His Ala Pro Thr
            1220                1225                1230
Gly Ser Gly Lys Ser Thr Lys Val Pro Ala Ala Tyr Ala Ala Gln Gly
        1235                1240                1245
Tyr Lys Val Leu Val Leu Asn Pro Ser Val Ala Ala Thr Leu Gly Phe
    1250                1255                1260
Gly Ala Tyr Met Ser Lys Ala His Gly Ile Asp Pro Asn Ile Arg Thr
1265                1270                1275                1280
Gly Val Arg Thr Ile Thr Thr Gly Ser Pro Ile Thr Tyr Ser Thr Tyr
                1285                1290                1295
Gly Lys Phe Leu Ala Asp Gly Gly Cys Ser Gly Gly Ala Tyr Asp Val
            1300                1305                1310
Ile Ile Cys Asp Glu Cys His Ser Thr Asp Ala Thr Ser Ile Leu Gly
        1315                1320                1325
Ile Gly Thr Val Leu Asp Gln Ala Glu Thr Ala Gly Ala Arg Leu Val
    1330                1335                1340
Val Leu Ala Thr Ala Thr Pro Pro Gly Ser Val Thr Val Pro His Pro
1345                1350                1355                1360
Asn Ile Glu Glu Val Ala Leu Ser Thr Thr Gly Glu Ile Pro Phe Tyr
                1365                1370                1375
Gly Lys Ala Ile Pro Leu Glu Val Ile Lys Gly Gly Arg His Leu Ile
            1380                1385                1390
Phe Cys His Ser Lys Lys Lys Cys Asp Glu Leu Ala Ala Lys Leu Val
        1395                1400                1405
Ala Leu Gly Ile Asn Ala Val Ala Tyr Tyr Arg Gly Leu Asp Val Ser
    1410                1415                1420
Val Ile Pro Thr Ser Gly Asp Val Val Val Ala Thr Asp Ala Leu
1425                1430                1435                1440
Met Thr Gly Tyr Thr Gly Asp Phe Asp Ser Val Ile Asp Cys Asn Thr
                1445                1450                1455
Cys Val Thr Gln Thr Val Asp Leu Ser Leu Asp Pro Thr Phe Thr Ile
            1460                1465                1470
Glu Thr Ile Thr Leu Pro Gln Asp Ala Val Ser Arg Thr Gln Arg Arg
        1475                1480                1485
Gly Arg Thr Gly Arg Gly Lys Pro Gly Ile Tyr Arg Phe Val Ala Pro
    1490                1495                1500
```

-continued

```
Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
        1540                1545                1550

Asp His Leu Glu Phe Trp Glu Gly Val Phe Thr Gly Leu Thr His Ile
    1555                1560                1565

Asp Ala His Phe Leu Ser Gln Thr Lys Gln Ser Gly Glu Asn Leu Pro
1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
        1620                1625                1630

Asn Glu Ile Thr Leu Thr His Pro Val Thr Lys Tyr Ile Met Thr Cys
    1635                1640                1645

Met Ser Ala Asp Leu Glu Val Val Thr Ser Thr Trp Val Leu Val Gly
1650                1655                1660

Gly Val Leu Ala Ala Leu Ala Ser Tyr Cys Leu Ser Thr Gly Cys Val
1665                1670                1675                1680

Val Ile Val Gly Arg Val Val Leu Ser Gly Lys Pro Ala Ile Ile Pro
            1685                1690                1695

Asp Arg Glu Val Leu Tyr Gln Glu Phe Asp Glu Met Glu Glu Cys Ser
        1700                1705                1710

Gln His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg Gln Ala Glu
1730                1735                1740

Val Ile Ala Pro Ala Val Gln Thr Asn Trp Gln Lys Leu Glu Thr Phe
1745                1750                1755                1760

Trp Ala Lys His Met Trp Asn Phe Ile Ser Gly Ile His Tyr Leu Ala
            1765                1770                1775

Gly Leu Ser Thr Leu Pro Gly Asn Pro Ala Ile Ala Ser Leu Met Ala
        1780                1785                1790

Phe Thr Ala Ala Val Thr Ser Pro Leu Thr Thr Ser Gln Thr Leu Leu
    1795                1800                1805

Phe Asn Ile Leu Gly Gly Trp Val Ala Ala Gln Leu Ala Ala Pro Gly
1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
            1845                1850                1855

Ala Gly Val Ala Gly Ala Leu Val Ala Phe Lys Ile Met Ser Gly Glu
        1860                1865                1870

Val Pro Ser Thr Glu Asp Leu Val Asn Leu Leu Pro Ala Ile Leu Ser
    1875                1880                1885

Pro Gly Ala Leu Val Val Gly Val Val Cys Ala Ala Ile Leu Arg Arg
1890                1895                1900

His Val Gly Pro Gly Glu Gly Ala Val Gln Trp Met Asn Arg Leu Ile
1905                1910                1915                1920

Ala Phe Ala Ser Arg Gly Thr His Val Ser Pro Thr His Tyr Val Pro
```

-continued

```
                1925                1930                1935
Glu Ser Asp Ala Ala Arg Val Thr Ala Ile Leu Ser Ser Leu Thr
            1940                1945                1950

Val Thr Gln Leu Leu Arg Arg Leu His Gln Trp Ile Ser Ser Glu Cys
            1955                1960                1965

Thr Thr Pro Cys Ser Gly Ser Trp Leu Arg Asp Ile Trp Asp Trp Ile
            1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
            2005                2010                2015

Gly Val Trp Arg Gly Asp Gly Ile Met His Thr Arg Cys His Cys Gly
            2020                2025                2030

Ala Glu Ile Thr Gly His Val Lys Asn Gly Thr Met Arg Ile Val Gly
            2035                2040                2045

Pro Arg Thr Cys Arg Asn Met Trp Ser Gly Thr Phe Pro Ile Asn Ala
            2050                2055                2060

Tyr Thr Thr Gly Pro Cys Thr Pro Leu Pro Ala Pro Asn Tyr Thr Phe
2065                2070                2075                2080

Ala Leu Trp Arg Val Ser Ala Glu Glu Tyr Val Glu Ile Arg Gln Val
            2085                2090                2095

Gly Asp Phe His Tyr Val Thr Gly Met Thr Thr Asp Asn Leu Lys Cys
            2100                2105                2110

Pro Cys Gln Val Pro Ser Pro Glu Phe Phe Thr Glu Leu Asp Gly Val
            2115                2120                2125

Arg Leu His Arg Phe Ala Pro Pro Cys Lys Pro Leu Leu Arg Glu Glu
            2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
            2180                2185                2190

Gly Ser Pro Pro Ser Val Ala Ser Ser Ser Ala Ser Gln Leu Ser Ala
            2195                2200                2205

Pro Ser Leu Lys Ala Thr Cys Thr Ala Asn His Asp Ser Pro Asp Ala
            2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Asp Pro Leu Val Ala Glu Glu Asp Glu Arg Glu Ile Ser Val Pro Ala
            2260                2265                2270

Glu Ile Leu Arg Lys Ser Arg Arg Phe Ala Gln Ala Leu Pro Val Trp
            2275                2280                2285

Ala Arg Pro Asp Tyr Asn Pro Pro Leu Val Glu Thr Trp Lys Lys Pro
            2290                2295                2300

Asp Tyr Glu Pro Pro Val Val His Gly Cys Pro Leu Pro Pro Pro Lys
2305                2310                2315                2320

Ser Pro Pro Val Pro Pro Pro Arg Lys Lys Arg Thr Val Val Leu Thr
            2325                2330                2335

Glu Ser Thr Leu Ser Thr Ala Leu Ala Glu Leu Ala Ile Lys Ser Phe
            2340                2345                2350
```

-continued

Gly Ser Ser Ser Thr Ser Gly Ile Thr Gly Asp Asn Thr Thr Thr Ser
            2355                2360                2365

Ser Glu Pro Ala Pro Ser Gly Cys Pro Arg Asp Ser Asp Ala Glu Ser
    2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Glu Ala Ser Ala Glu Asp
            2405                2410                2415

Val Val Arg Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
            2435                2440                2445

Ser Leu Leu Arg His His Asn Leu Val Tyr Ser Thr Thr Ser Arg Ser
            2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
            2485                2490                2495

Lys Val Lys Ala Asn Leu Leu Ser Val Glu Glu Ala Cys Ser Leu Thr
            2500                2505                2510

Pro Pro His Ser Ala Lys Ser Lys Phe Gly Tyr Gly Ala Lys Asp Val
            2515                2520                2525

Arg Cys His Ala Arg Lys Ala Val Thr His Ile Asn Ser Val Trp Lys
            2530                2535                2540

Asp Leu Leu Glu Asp Asn Val Thr Pro Ile Asp Thr Thr Ile Met Ala
2545                2550                2555                2560

Lys Asn Glu Val Phe Cys Val Gln Pro Glu Lys Gly Gly Arg Lys Pro
            2565                2570                2575

Ala Arg Leu Ile Val Phe Pro Asp Leu Gly Val Arg Val Cys Glu Lys
            2580                2585                2590

Met Ala Leu Tyr Asp Val Val Thr Lys Leu Pro Leu Ala Val Met Gly
            2595                2600                2605

Ser Ser Tyr Gly Phe Gln Tyr Ser Pro Gly Gln Arg Val Glu Phe Leu
            2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
            2675                2680                2685

Ser Arg Gly Glu Asn Cys Gly Tyr Arg Arg Cys Arg Ala Ser Gly Val
            2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
            2755                2760                2765

```
Pro Pro Gly Asp Pro Pro Gln Pro Glu Tyr Asp Leu Glu Leu Ile Thr
        2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asp
2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Thr Trp Arg His Arg Ala Arg Ser Val Arg
        2915                2920                2925

Ala Arg Leu Leu Ala Arg Gly Gly Arg Ala Ala Ile Cys Gly Lys Tyr
2930                2935                2940

Leu Phe Asn Trp Ala Val Arg Thr Lys Leu Lys Leu Thr Pro Ile Ala
2945                2950                2955                2960

Ala Ala Gly Gln Leu Asp Leu Ser Gly Trp Phe Thr Ala Gly Tyr Ser
                2965                2970                2975

Gly Gly Gly Ile Phe His Ser Val Ser His Ala Arg Pro Arg Trp Phe
            2980                2985                2990

Trp Ser Cys Leu Leu Leu Leu Ala Ala Gly Val Gly Ile Tyr Leu Leu
        2995                3000                3005

Pro Asn Arg
    3010

<210> SEQ ID NO 6
<211> LENGTH: 3011
<212> TYPE: PRT
<213> ORGANISM: Hepatitis C virus

<400> SEQUENCE: 6

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125
```

```
Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
                195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
                275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Thr Asp Met Ile Ala Gly Ala His
                340                 345                 350

Trp Gly Val Leu Ala Gly Ile Ala Tyr Phe Ser Met Val Gly Asn Trp
                355                 360                 365

Ala Lys Val Leu Val Val Leu Leu Leu Phe Ala Gly Val Asp Ala Glu
370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
                435                 440                 445

Ser Ser Gly Cys Pro Glu Arg Leu Ala Ser Cys Arg Arg Leu Thr Asp
450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
                515                 520                 525

Trp Gly Ala Asn Asp Thr Asp Val Phe Val Leu Asn Asn Thr Arg Pro
530                 535                 540
```

-continued

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
            565                 570                 575

Asn Thr Leu Leu Cys Pro Thr Asp Cys Phe Arg Lys His Pro Glu Ala
        580                 585                 590

Thr Tyr Ser Arg Cys Gly Ser Gly Pro Trp Ile Thr Pro Arg Cys Met
    595                 600                 605

Val Asp Tyr Pro Tyr Arg Leu Trp His Tyr Pro Cys Thr Ile Asn Tyr
610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Gln Trp
        660                 665                 670

Gln Val Leu Pro Cys Ser Phe Thr Thr Leu Pro Ala Leu Ser Thr Gly
    675                 680                 685

Leu Ile His Leu His Gln Asn Ile Val Asp Val Gln Tyr Leu Tyr Gly
690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
            725                 730                 735

Met Met Leu Leu Ile Ser Gln Ala Glu Ala Ala Leu Glu Asn Leu Val
        740                 745                 750

Ile Leu Asn Ala Ala Ser Leu Ala Gly Thr His Gly Leu Val Ser Phe
    755                 760                 765

Leu Val Phe Phe Cys Phe Ala Trp Tyr Leu Lys Gly Arg Trp Val Pro
770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Val Leu Thr Leu Ser
        820                 825                 830

Pro Tyr Tyr Lys Arg Tyr Ile Ser Trp Cys Met Trp Trp Leu Gln Tyr
    835                 840                 845

Phe Leu Thr Arg Val Glu Ala Gln Leu His Val Trp Val Pro Pro Arg
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
            885                 890                 895

Gly Pro Leu Trp Ile Leu Gln Ala Ser Leu Leu Lys Val Pro Tyr Phe
        900                 905                 910

Val Arg Val Gln Gly Leu Leu Arg Ile Cys Ala Leu Ala Arg Lys Ile
    915                 920                 925

Ala Gly Gly His Tyr Val Gln Met Ala Ile Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe

```
                965                 970                 975
Ser Arg Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Gln
                995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Arg Asn Gln Val Glu
                1045                1050                1055

Gly Glu Val Gln Ile Val Ser Thr Ala Thr Gln Thr Phe Leu Ala Thr
                1060                1065                1070

Cys Ile Asn Gly Val Cys Trp Thr Val Tyr His Gly Ala Gly Thr Arg
                1075                1080                1085

Thr Ile Ala Ser Pro Lys Gly Pro Val Ile Gln Met Tyr Thr Asn Val
                1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
                1140                1145                1150

Leu Ser Pro Arg Pro Ile Ser Tyr Leu Lys Gly Ser Ser Gly Gly Pro
                1155                1160                1165

Leu Leu Cys Pro Ala Gly His Ala Val Gly Leu Phe Arg Ala Ala Val
                1170                1175                1180

Cys Thr Arg Gly Val Ala Lys Ala Val Asp Phe Ile Pro Val Glu Asn
1185                1190                1195                1200

Leu Gly Thr Thr Met Arg Ser Pro Val Phe Thr Asp Asn Ser Ser Pro
                1205                1210                1215

Pro Ala Val Pro Gln Ser Phe Gln Val Gly His Leu His Ala Pro Thr
                1220                1225                1230

Gly Ser Gly Lys Ser Thr Lys Val Pro Ala Ala Tyr Ala Ala Gln Gly
                1235                1240                1245

Tyr Lys Val Leu Val Leu Asn Pro Ser Val Ala Ala Thr Leu Gly Phe
                1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
                1300                1305                1310

Ile Ile Cys Asp Glu Cys His Ser Thr Asp Ala Thr Ser Ile Leu Gly
                1315                1320                1325

Ile Gly Thr Val Leu Asp Gln Ala Glu Thr Ala Gly Ala Arg Leu Val
                1330                1335                1340

Val Leu Ala Thr Ala Thr Pro Pro Gly Ser Val Thr Val Ser His Pro
1345                1350                1355                1360

Asn Ile Glu Glu Val Ala Leu Pro Thr Thr Gly Glu Ile Pro Phe Tyr
                1365                1370                1375

Gly Lys Ala Ile Pro Leu Glu Val Ile Lys Gly Gly Arg His Leu Ile
                1380                1385                1390
```

-continued

Phe Cys His Ser Lys Lys Cys Asp Glu Leu Ala Ala Lys Leu Val
        1395                1400                1405

Ala Leu Gly Ile Asn Ala Val Ala Tyr Tyr Arg Gly Leu Asp Val Ser
    1410                1415                1420

Val Ile Pro Thr Ser Gly Asp Val Val Val Ser Thr Asp Ala Leu
1425            1430                1435                1440

Met Thr Gly Phe Thr Gly Asp Phe Asp Ser Val Ile Asp Cys Asn Thr
            1445                1450                1455

Cys Val Thr Gln Thr Val Asp Leu Ser Leu Asp Pro Thr Phe Thr Ile
        1460                1465                1470

Glu Thr Thr Thr Leu Pro Gln Asp Ala Val Ser Arg Thr Gln Arg Arg
    1475                1480                1485

Gly Arg Thr Gly Arg Gly Lys Pro Gly Ile Tyr Arg Phe Val Ala Pro
    1490                1495                1500

Gly Glu Arg Pro Ser Gly Met Phe Asp Ser Ser Val Leu Cys Glu Cys
1505            1510                1515                1520

Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
    1540                1545                1550

Asp His Leu Glu Phe Trp Glu Gly Val Phe Thr Gly Leu Thr His Ile
    1555                1560                1565

Asp Ala His Phe Leu Ser Gln Thr Lys Gln Ser Gly Glu Asn Phe Pro
    1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
            1620                1625                1630

Asn Glu Val Thr Leu Thr His Pro Ile Thr Lys Tyr Ile Met Thr Cys
        1635                1640                1645

Met Ser Ala Asp Leu Glu Val Val Thr Ser Thr Trp Val Leu Ala Gly
            1650                1655                1660

Gly Val Leu Ala Ala Leu Ala Ser Tyr Cys Leu Ser Thr Gly Cys Val
1665                1670                1675                1680

Val Ile Val Gly Arg Ile Val Leu Ser Gly Lys Pro Ala Ile Ile Pro
            1685                1690                1695

Asp Arg Glu Val Leu Tyr Gln Glu Phe Asp Glu Met Glu Glu Cys Ser
            1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg His Ala Glu
        1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile His Tyr Leu Ala
            1765                1770                1775

Gly Leu Ser Thr Leu Pro Gly Asn Pro Ala Ile Ala Ser Leu Met Ala
        1780                1785                1790

Phe Thr Ala Ala Val Thr Ser Pro Leu Thr Thr Gly Gln Thr Leu Leu
        1795                1800                1805

Phe Asn Ile Leu Gly Gly Trp Val Ala Ala Gln Leu Ala Pro Gly
    1810                1815                1820

Ala Ala Thr Ala Phe Val Gly Ala Gly Leu Ala Gly Ala Ile Gly
1825                1830                1835                1840

Ser Val Gly Leu Gly Lys Val Leu Val Asp Ile Leu Ala Gly Tyr Gly
                1845                1850                1855

Ala Gly Val Ala Gly Ala Leu Val Ala Phe Lys Ile Met Ser Gly Glu
                1860                1865                1870

Val Pro Ser Thr Glu Asp Leu Val Asn Leu Leu Pro Ala Ile Leu Ser
                1875                1880                1885

Pro Gly Ala Leu Val Val Gly Val Val Cys Ala Ala Ile Leu Arg Arg
    1890                1895                1900

His Val Gly Pro Ser Glu Gly Ala Val Gln Trp Met Asn Arg Leu Ile
1905                1910                1915                1920

Ala Phe Ala Ser Arg Gly Thr His Val Ser Pro Thr His Tyr Val Pro
                1925                1930                1935

Glu Ser Asp Ala Ala Ala Arg Val Thr Ala Ile Leu Ser Ser Leu Thr
                1940                1945                1950

Val Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp Ile
    1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
                2020                2025                2030

Ala Glu Ile Thr Gly His Val Lys Asn Gly Thr Met Arg Ile Val Gly
                2035                2040                2045

Pro Arg Thr Cys Arg Asn Met Trp Ser Gly Thr Phe Pro Ile Asn Ala
    2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Val Thr Thr Asp Asn Leu Lys Cys
                2100                2105                2110

Pro Cys Gln Ile Pro Ser Pro Glu Phe Phe Thr Glu Leu Asp Gly Val
                2115                2120                2125

Arg Leu His Arg Phe Ala Pro Pro Cys Lys Pro Leu Leu Arg Glu Glu
    2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
                2180                2185                2190

Gly Ser Pro Pro Ser Met Ala Ser Ser Ser Ala Ser Gln Leu Ser Ala
                2195                2200                2205

Pro Ser Leu Lys Ala Thr Cys Thr Ala Asn His Asp Ser Pro Asp Ala
    2210                2215                2220

Glu Leu Ile Glu Ala Asn Leu Leu Trp Arg Gln Glu Met Gly Gly Asn

```
                2225                2230                2235                2240
        Ile Thr Arg Val Glu Ser Glu Asn Lys Val Val Ile Leu Asp Ser Phe
                    2245                2250                2255
        Asp Pro Leu Val Ala Glu Glu Asp Glu Arg Glu Val Ser Val Pro Ala
                    2260                2265                2270
        Glu Ile Leu Arg Lys Ser Arg Arg Phe Ala Arg Ala Leu Pro Val Trp
                    2275                2280                2285
        Ala Arg Pro Asp Tyr Asn Pro Pro Leu Val Glu Thr Trp Lys Lys Pro
                    2290                2295                2300
        Asp Tyr Glu Pro Pro Val Val His Gly Cys Pro Leu Pro Pro Pro Arg
        2305                2310                2315                2320
        Ser Pro Pro Val Pro Pro Pro Arg Lys Lys Arg Thr Val Val Leu Thr
                    2325                2330                2335
        Glu Ser Thr Leu Ser Thr Ala Leu Ala Glu Leu Ala Thr Lys Ser Phe
                    2340                2345                2350
        Gly Gly Ser Ser Thr Ser Gly Ile Thr Gly Asp Asn Thr Thr Thr Ser
                    2355                2360                2365
        Ser Glu Pro Ala Pro Ser Gly Cys Pro Pro Asp Ser Asp Val Glu Ser
                    2370                2375                2380
        Tyr Ser Ser Met Pro Pro Leu Glu Gly Glu Pro Gly Asp Pro Asp Leu
        2385                2390                2395                2400
        Ser Asp Gly Ser Trp Ser Thr Val Ser Ser Gly Ala Asp Thr Glu Asp
                    2405                2410                2415
        Ala Val Cys Cys Ser Met Ser Tyr Ser Trp Thr Gly Ala Leu Ile Thr
                    2420                2425                2430
        Pro Cys Ala Ala Glu Glu Gln Lys Leu Pro Ile Asn Ala Leu Ser Asn
                    2435                2440                2445
        Ser Leu Leu Arg His His Asn Leu Val Tyr Ser Thr Thr Ser Arg Ser
                    2450                2455                2460
        Ala Cys Gln Arg Gln Lys Lys Val Thr Phe Asp Arg Leu Gln Val Leu
        2465                2470                2475                2480
        Asp Ser His Tyr Gln Asp Val Leu Lys Glu Val Lys Ala Ala Ala Ser
                    2485                2490                2495
        Lys Val Lys Ala Asn Leu Leu Ser Val Glu Glu Ala Cys Ser Leu Thr
                    2500                2505                2510
        Pro Pro His Ser Ala Lys Ser Lys Phe Gly Tyr Gly Ala Lys Asp Val
                    2515                2520                2525
        Arg Cys His Ala Arg Lys Ala Val Ala His Ile Asn Ser Val Trp Lys
                    2530                2535                2540
        Asp Leu Leu Glu Asp Ser Val Thr Pro Ile Asp Thr Thr Ile Met Ala
        2545                2550                2555                2560
        Lys Asn Glu Val Phe Cys Val Gln Pro Glu Lys Gly Gly Arg Lys Pro
                    2565                2570                2575
        Ala Arg Leu Ile Val Phe Pro Asp Leu Gly Val Arg Val Cys Glu Lys
                    2580                2585                2590
        Met Ala Leu Tyr Asp Val Val Ser Lys Leu Pro Leu Ala Val Met Gly
                    2595                2600                2605
        Ser Ser Tyr Gly Phe Gln Tyr Ser Pro Gly Gln Arg Val Glu Phe Leu
                    2610                2615                2620
        Val Gln Ala Trp Lys Ser Lys Lys Thr Pro Met Gly Phe Ser Tyr Asp
        2625                2630                2635                2640
        Thr Arg Cys Phe Asp Ser Thr Val Thr Glu Ser Asp Ile Arg Thr Glu
                    2645                2650                2655
```

```
Glu Ala Ile Tyr Gln Cys Cys Asp Leu Asp Pro Gln Ala Arg Val Ala
        2660                2665                2670

Ile Lys Ser Leu Thr Glu Arg Leu Tyr Val Gly Pro Leu Thr Asn
    2675                2680                2685

Ser Arg Gly Glu Asn Cys Gly Tyr Arg Cys Arg Ala Ser Gly Val
    2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
        2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
            2835                2840                2845

Phe Phe Ser Val Leu Ile Ala Arg Asp Gln Leu Glu Gln Ala Leu Asn
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
            2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
            2915                2920                2925

Ala Arg Leu Leu Ser Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
            2965                2970                2975

Gly Gly Gly Ile Phe His Ser Val Ser His Ala Arg Pro Arg Trp Phe
            2980                2985                2990

Trp Arg Cys Leu Leu Leu Leu Ala Ala Gly Val Gly Ile Tyr Leu Leu
            2995                3000                3005

Pro Asn Arg
    3010

<210> SEQ ID NO 7
<211> LENGTH: 3011
<212> TYPE: PRT
<213> ORGANISM: Hepatitis C virus

<400> SEQUENCE: 7

Met Ser Thr Asn Pro Lys Pro Gln Arg Lys Thr Lys Arg Asn Thr Asn
```

-continued

```
1               5                   10                  15
Arg Arg Pro Gln Asp Val Lys Phe Pro Gly Gly Gln Ile Val Gly
                20                  25                  30
Gly Val Tyr Leu Leu Pro Arg Arg Gly Pro Arg Leu Gly Val Arg Ala
                35                  40                  45
Thr Arg Lys Thr Ser Glu Arg Ser Gln Pro Arg Gly Arg Arg Gln Pro
 50                  55                  60
Ile Pro Lys Ala Arg Arg Pro Glu Gly Arg Thr Trp Ala Gln Pro Gly
 65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Leu
                130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Tyr
                180                 185                 190
Gln Val Arg Asn Ser Ser Gly Leu Tyr His Val Thr Asn Asp Cys Pro
                195                 200                 205
Asn Ser Ser Ile Val Tyr Glu Ala Ala Asp Ala Ile Leu His Thr Pro
 210                 215                 220
Gly Cys Val Pro Cys Val Arg Glu Gly Asn Ala Ser Arg Cys Trp Val
225                 230                 235                 240
Ala Val Thr Pro Thr Val Ala Thr Arg Asp Gly Lys Leu Pro Thr Thr
                245                 250                 255
Gln Leu Arg Arg His Ile Asp Leu Leu Val Gly Ser Ala Thr Leu Cys
                260                 265                 270
Ser Ala Leu Tyr Val Gly Asp Leu Cys Gly Ser Val Phe Leu Val Gly
                275                 280                 285
Gln Leu Phe Thr Phe Ser Pro Arg Arg His Trp Thr Thr Gln Asp Cys
                290                 295                 300
Asn Cys Ser Ile Tyr Pro Gly His Ile Thr Gly His Arg Met Ala Trp
305                 310                 315                 320
Asp Met Met Met Asn Trp Ser Pro Thr Ala Ala Leu Val Val Ala Gln
                325                 330                 335
Leu Leu Arg Ile Pro Gln Ala Ile Met Asp Met Ile Ala Gly Ala His
                340                 345                 350
Trp Gly Val Leu Ala Gly Ile Ala Tyr Phe Ser Met Val Gly Asn Trp
                355                 360                 365
Ala Lys Val Leu Val Val Leu Leu Leu Phe Ala Gly Val Asp Ala Glu
                370                 375                 380
Thr His Val Thr Gly Gly Ser Ala Gly Arg Thr Thr Ala Gly Leu Val
385                 390                 395                 400
Gly Leu Leu Thr Pro Gly Ala Lys Gln Asn Ile Gln Leu Ile Asn Thr
                405                 410                 415
Asn Gly Ser Trp His Ile Asn Ser Thr Ala Leu Asn Cys Asn Glu Ser
                420                 425                 430
```

```
Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
        450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
                515                 520                 525

Trp Gly Ala Asn Asp Thr Asp Val Phe Val Leu Asn Asn Thr Arg Pro
        530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
                565                 570                 575

Asn Thr Leu Leu Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
        610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
        740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
770                 775                 780

Gly Ala Val Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Met Trp Trp Leu Gln Tyr
                835                 840                 845
```

-continued

```
Phe Leu Thr Arg Val Glu Ala Gln Leu His Val Trp Val Pro Pro Leu
850                 855                 860
Asn Val Arg Gly Gly Arg Asp Ala Val Ile Leu Leu Met Cys Val Val
865                 870                 875                 880
His Pro Thr Leu Val Phe Asp Ile Thr Lys Leu Leu Leu Ala Ile Phe
                    885                 890                 895
Gly Pro Leu Trp Ile Leu Gln Ala Ser Leu Leu Lys Val Pro Tyr Phe
                900                 905                 910
Val Arg Val Gln Gly Leu Leu Arg Ile Cys Ala Leu Ala Arg Lys Ile
                915                 920                 925
Ala Gly Gly His Tyr Val Gln Met Ala Ile Ile Lys Leu Gly Ala Leu
        930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Val Phe
                965                 970                 975
Ser Arg Met Glu Thr Lys Leu Ile Thr Trp Gly Ala Asp Thr Ala Ala
                980                 985                 990
Cys Gly Asp Ile Ile Asn Gly Leu Pro Val Ser Ala Arg Arg Gly Gln
            995                 1000                1005
Glu Ile Leu Leu Gly Pro Ala Asp Gly Met Val Ser Lys Gly Trp Arg
        1010                1015                1020
Leu Leu Ala Pro Ile Thr Ala Tyr Ala Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Ile Val Ser Thr Ala Thr Gln Thr Phe Leu Ala Thr
            1060                1065                1070
Cys Ile Asn Gly Val Cys Trp Thr Val Tyr His Gly Ala Gly Thr Arg
        1075                1080                1085
Thr Ile Ala Ser Pro Lys Gly Pro Val Ile Gln Met Tyr Thr Asn Val
    1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
                1125                1130                1135
Ala Asp Val Ile Pro Val Arg Arg Arg Gly Asp Ser Arg Gly Ser Leu
            1140                1145                1150
Leu Ser Pro Arg Pro Ile Ser Tyr Leu Lys Gly Ser Ser Gly Gly Pro
        1155                1160                1165
Leu Leu Cys Pro Ala Gly His Ala Val Gly Leu Phe Arg Ala Ala Val
    1170                1175                1180
Cys Thr Arg Gly Val Ala Lys Ala Val Asp Phe Ile Pro Val Glu Asn
1185                1190                1195                1200
Leu Glu Thr Thr Met Arg Ser Pro Val Phe Thr Asp Asn Ser Ser Pro
                1205                1210                1215
Pro Ala Val Pro Gln Ser Phe Gln Val Ala His Leu His Ala Pro Thr
            1220                1225                1230
Gly Ser Gly Lys Ser Thr Lys Val Pro Ala Ala Tyr Ala Ala Gln Gly
        1235                1240                1245
Tyr Lys Val Leu Val Leu Asn Pro Ser Val Ala Ala Thr Leu Gly Phe
    1250                1255                1260
Gly Ala Tyr Met Ser Lys Ala His Gly Val Asp Pro Asn Ile Arg Thr
```

-continued

```
            1265                1270                1275                1280
Gly Val Arg Thr Ile Thr Thr Gly Ser Pro Ile Thr Tyr Ser Thr Tyr
                1285                1290                1295
Gly Lys Phe Leu Ala Asp Gly Gly Cys Ser Gly Gly Ala Tyr Asp Ile
            1300                1305                1310
Ile Ile Cys Asp Glu Cys His Ser Thr Asp Ala Thr Ser Ile Leu Gly
            1315                1320                1325
Ile Gly Thr Val Leu Asp Gln Ala Glu Thr Ala Gly Ala Arg Leu Val
            1330                1335                1340
Val Leu Ala Thr Ala Thr Pro Pro Gly Ser Val Thr Val Ser His Pro
1345                1350                1355                1360
Asn Ile Glu Glu Val Ala Leu Ser Thr Thr Gly Glu Ile Pro Phe Tyr
                1365                1370                1375
Gly Lys Ala Ile Pro Leu Glu Val Ile Lys Gly Gly Arg His Leu Ile
            1380                1385                1390
Phe Cys His Ser Lys Lys Lys Cys Asp Glu Leu Ala Ala Lys Leu Val
            1395                1400                1405
Ala Leu Gly Ile Asn Ala Val Ala Tyr Tyr Arg Gly Leu Asp Val Ser
            1410                1415                1420
Val Ile Pro Thr Ser Gly Asp Val Val Val Val Ser Thr Asp Ala Leu
1425                1430                1435                1440
Met Thr Gly Phe Thr Gly Asp Phe Asp Ser Val Ile Asp Cys Asn Thr
                1445                1450                1455
Cys Val Thr Gln Thr Val Asp Phe Ser Leu Asp Pro Thr Phe Thr Ile
            1460                1465                1470
Glu Thr Thr Thr Leu Pro Gln Asp Ala Val Ser Arg Thr Gln Arg Arg
            1475                1480                1485
Gly Arg Thr Gly Arg Gly Lys Pro Gly Ile Tyr Arg Phe Val Ala Pro
            1490                1495                1500
Gly Glu Arg Pro Ser Gly Met Phe Asp Ser Ser Val Leu Cys Glu Cys
1505                1510                1515                1520
Tyr Asp Ala Gly Cys Ala Trp Tyr Glu Leu Thr Pro Ala Glu Thr Thr
                1525                1530                1535
Val Arg Leu Arg Ala Tyr Met Asn Thr Pro Gly Leu Pro Val Cys Gln
                1540                1545                1550
Asp His Leu Glu Phe Trp Glu Gly Val Phe Thr Gly Leu Thr His Ile
            1555                1560                1565
Asp Ala His Phe Leu Ser Gln Thr Lys Gln Ser Gly Glu Asn Phe Pro
            1570                1575                1580
Tyr Leu Val Ala Tyr Gln Ala Thr Val Cys Ala Arg Ala Gln Ala Pro
1585                1590                1595                1600
Pro Pro Ser Trp Asp Gln Met Trp Lys Cys Leu Ile Arg Leu Lys Pro
                1605                1610                1615
Thr Leu His Gly Pro Thr Pro Leu Leu Tyr Arg Leu Gly Ala Val Gln
                1620                1625                1630
Asn Glu Val Thr Leu Thr His Pro Ile Thr Lys Tyr Ile Met Thr Cys
            1635                1640                1645
Met Ser Ala Asp Leu Glu Val Val Thr Ser Thr Trp Val Leu Val Gly
            1650                1655                1660
Gly Val Leu Ala Ala Leu Ala Ala Tyr Cys Leu Ser Thr Gly Cys Val
1665                1670                1675                1680
Val Ile Val Gly Arg Ile Val Leu Ser Gly Lys Pro Ala Ile Ile Pro
                1685                1690                1695
```

-continued

Asp Arg Glu Val Leu Tyr Gln Glu Phe Asp Glu Met Glu Glu Cys Ser
          1700                1705                1710

Gln His Leu Pro Tyr Ile Gln Gly Met Met Leu Ala Glu Gln Phe
          1715                1720                1725

Lys Gln Lys Ala Leu Gly Leu Leu Gln Thr Ala Ser Arg Gln Ala Glu
          1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
          1765                1770                1775

Gly Leu Ser Thr Leu Pro Gly Asn Pro Ala Ile Ala Ser Leu Met Ala
          1780                1785                1790

Phe Thr Ala Ala Val Thr Ser Pro Leu Thr Thr Gly Gln Thr Leu Leu
          1795                1800                1805

Phe Asn Ile Leu Gly Gly Trp Val Ala Ala Gln Leu Ala Ala Pro Gly
          1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
          1845                1850                1855

Ala Gly Val Ala Gly Ala Leu Val Ala Phe Lys Ile Met Ser Gly Glu
          1860                1865                1870

Val Pro Ser Thr Glu Asp Leu Val Asn Leu Leu Pro Ala Ile Leu Ser
          1875                1880                1885

Pro Gly Ala Leu Val Val Gly Val Val Cys Ala Ala Ile Leu Arg Arg
          1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
          1925                1930                1935

Glu Ser Asp Ala Ala Ala Arg Val Thr Ala Ile Leu Ser Ser Leu Thr
          1940                1945                1950

Val Thr Gln Leu Leu Arg Arg Leu His Gln Trp Ile Ser Ser Glu Cys
          1955                1960                1965

Thr Thr Pro Cys Ser Gly Ser Trp Leu Arg Asp Ile Trp Asp Trp Ile
          1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
          2005                2010                2015

Gly Val Trp Arg Gly Asp Gly Ile Met His Thr Arg Cys His Cys Gly
          2020                2025                2030

Ala Glu Ile Thr Gly His Val Lys Asn Gly Thr Met Arg Ile Val Gly
          2035                2040                2045

Pro Arg Thr Cys Arg Asn Met Trp Ser Gly Thr Phe Pro Ile Asn Ala
          2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
          2085                2090                2095

Gly Asp Phe His Tyr Val Ser Gly Met Thr Thr Asp Asn Leu Lys Cys
          2100                2105                2110

```
Pro Cys Gln Ile Pro Ser Pro Glu Phe Phe Thr Glu Leu Asp Gly Val
            2115                2120                2125

Arg Leu His Arg Phe Ala Pro Pro Cys Lys Pro Leu Leu Arg Glu Glu
        2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
        2180                2185                2190

Gly Ser Pro Pro Ser Met Ala Ser Ser Ala Ser Gln Leu Ser Ala
        2195                2200                2205

Pro Ser Leu Lys Ala Thr Cys Thr Ala Asn His Asp Ser Pro Asp Ala
        2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Asp Pro Leu Val Ala Glu Glu Asp Glu Arg Glu Val Ser Val Pro Ala
        2260                2265                2270

Glu Ile Leu Arg Lys Ser Arg Arg Phe Ala Arg Ala Leu Pro Val Trp
        2275                2280                2285

Ala Arg Pro Asp Tyr Asn Pro Pro Leu Val Glu Thr Trp Lys Lys Pro
        2290                2295                2300

Asp Tyr Glu Pro Pro Val Val His Gly Cys Pro Leu Pro Pro Pro Arg
2305                2310                2315                2320

Ser Pro Pro Val Pro Pro Pro Arg Lys Lys Arg Thr Val Val Leu Thr
            2325                2330                2335

Glu Ser Thr Leu Ser Thr Ala Leu Ala Glu Leu Ala Thr Lys Ser Phe
            2340                2345                2350

Gly Ser Ser Ser Thr Ser Gly Ile Thr Gly Asp Asn Thr Thr Thr Ser
        2355                2360                2365

Ser Glu Pro Ala Pro Ser Gly Cys Pro Pro Asp Ser Asp Val Glu Ser
    2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Gly Ala Asp Thr Glu Asp
                2405                2410                2415

Val Val Cys Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
        2435                2440                2445

Ser Leu Leu Arg His His Asn Leu Val Tyr Ser Thr Thr Ser Arg Ser
    2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
        2485                2490                2495

Lys Val Lys Ala Asn Leu Leu Ser Val Glu Glu Ala Cys Ser Leu Thr
            2500                2505                2510

Pro Pro His Ser Ala Lys Ser Lys Phe Gly Tyr Gly Ala Lys Asp Val
        2515                2520                2525

Arg Cys His Ala Arg Lys Ala Val Ala His Ile Asn Ser Val Trp Lys
```

-continued

```
                2530                2535                2540
Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
                2580                2585                2590

Met Ala Leu Tyr Asp Val Val Ser Lys Leu Pro Leu Ala Val Met Gly
            2595                2600                2605

Ser Ser Tyr Gly Phe Gln Tyr Ser Pro Gly Gln Arg Val Glu Phe Leu
            2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
                2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
            2675                2680                2685

Ser Arg Gly Glu Asn Cys Gly Tyr Arg Arg Cys Arg Ala Ser Gly Val
            2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
                2725                2730                2735

Gly Asp Asp Leu Val Val Ile Cys Glu Ser Ala Gly Val Gln Glu Asp
                2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
            2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
            2835                2840                2845

Phe Phe Ser Val Leu Ile Ala Arg Asp Gln Leu Glu Gln Ala Leu Asn
2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
            2915                2920                2925

Ala Arg Leu Leu Ser Arg Gly Gly Arg Ala Ala Ile Cys Gly Lys Tyr
            2930                2935                2940

Leu Phe Asn Trp Ala Val Arg Thr Lys Leu Lys Leu Thr Pro Ile Ala
2945                2950                2955                2960
```

```
Ala Ala Gly Arg Leu Asp Leu Ser Gly Trp Phe Thr Ala Gly Tyr Ser
                2965                2970                2975

Gly Gly Asp Ile Tyr His Ser Val Ser His Ala Arg Pro Arg Trp Phe
                2980                2985                2990

Trp Phe Cys Leu Leu Leu Leu Ala Ala Gly Val Gly Ile Tyr Leu Leu
        2995                3000                3005

Pro Asn Arg
    3010
```

OPTIMIZED HCV FULL-LENGTH INFECTIOUS CELL CULTURE SYSTEMS AND APPLICATIONS THEREOF

PRIORITY CLAIM TO RELATED APPLICATIONS

This application is a U.S. national stage application filed under 35 U.S.C. § 371 from International Application Serial No. PCT/DK2015/050325, which was filed 23 Oct. 2015, and published as WO2016/066171 on 6 May 2016, and which claims priority to Denmark Application No. PA 2014 70659, filed 28 Oct. 2014, which applications and publication are incorporated by reference as if reproduced herein and made a part hereof in their entirety, and the benefit of priority of each of which is claimed herein.

TECHNICAL FIELD OF THE INVENTION

The present invention relates to nucleic acid sequences that encode hepatitis C viruses (HCV) that are useful in the fundamental research of HCV as well as in the search of drug candidates and a vaccine against HCV. In particular the present invention relates to nucleic acid sequences that comprises HCV, which are capable of expressing said virus when transfected into cells and/or are capable of infectivity in vivo.

BACKGROUND OF THE INVENTION

Hepatitis C is one of the most widespread infectious diseases in the world. About 180 million people are infected with hepatitis C virus (HCV) worldwide with a yearly incidence of 3-4 million.

While the acute phase of infection is mostly asymptomatic, the majority of acutely infected individuals develops chronic hepatitis and is at increased risk of developing liver cirrhosis and hepatocellular carcinoma.

Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTR) and one long open reading frame (ORF) encoding a polyprotein, which is co- and post-translationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 7 major HCV genotypes (genotypes 1-7) have been identified, which differ by 31-33% at the nucleotide level and deduced amino acid level.

In addition, there are numerous subtypes (a, b, c, etc.), which differ by 20-25% on the nucleotide and deduced amino acid level.

Since its discovery in 1989, research on HCV has been hampered by the lack of appropriate cell culture systems allowing for research on the complete viral life cycle as well as new therapeutics and vaccines.

In 2001, a genotype 2a isolate (JFH1) was described, which subsequently was found to yield high RNA titers in the replicon system without adaptive mutations.

A major breakthrough occurred in 2005, when formation of infectious viral particles was reported after transfection of RNA transcripts from the JFH1 full-length consensus cDNA clone into Huh7 cells.

At the same time, it was demonstrated that the intragenotypic 2a/2a recombinant genome (J6/JFH1), in which the structural genes (Core, E1, E2), p7 and NS2 of JFH1 were replaced by the respective genes of clone J6CF, produced infectious viral particles in Huh7.5 cells (a cell line derived from bulk Huh7 cells) with an accelerated kinetic.

Cell culture derived J6/JFH viruses were apparently fully viable in vivo.

Despite the importance of the described cell culture systems they represent only a single isolate (genotype 2a) of HCV.

It is important to develop cell culture systems for representative strains of other HCV isolates, subtypes and genotypes, since neutralizing antibodies are not expected to cross-neutralize all genotypes and new specific antiviral compounds have differential efficiencies against different isolates, subtypes and genotypes.

To date, only the JFH1 (genotype 2a) clone could autonomously replicate and release infectious virus in cultured human hepatoma cells, Huh7 and Huh7.5; its efficient growth depended on mutations.

A JFH1 chimera with the 5'UTR-NS2 region from another genotype 2a strain cDNA clone, J6CF, had enhanced infectivity.

Besides, an H77 (genotype 1a) clone containing replicon-derived mutations was shown to produce infectious virus particles.

To facilitate HCV research and obtain basic knowledge for better and individualized treatment, the present inventors have aimed at developing culture systems for other HCV patient isolates.

Hence, improved and alternative HCV genomes of all genotypes, which are capable of expressing said virus when transfected into cells and are capable of infectivity in vivo, would be advantageous.

SUMMARY OF THE INVENTION

Thus, an object of the present invention relates to nucleotide sequences that encode HCV that are useful in the fundamental research of HCV as well as in the search of drug candidates and a vaccine against HCV.

In particular, it is an object of the present invention to provide nucleotide sequences of HCV which are capable of expressing said virus when transfected into cells and are capable of infectivity in vivo.

Thus, one aspect of the invention relates to an isolated nucleic acid molecule which encodes a human hepatitis C virus wherein the hepatitis C virus is derived from genotype 1a, isolate HCV-1_LSGF/S399F/TNm/4m (TNm, A1226G/Q1773H/N1927T/F2994S; 4m, A970T/I1312V/C2419R/A2919T) (SEQ ID NO:2) and has a nucleic acid sequence with 90% sequence identity to HCV-1_LSGF/S399F/TNm/4m (SEQ ID NO:2).

The nucleotide and amino acid numbering throughout is according to the H77 (1a) reference sequence (GenBank accession number AF009606). GenBank Accession No. AF009606 provides the following sequence:

MSTNPKPQRKTKRNTNRRPQDVKFPGGGQIVG-
GVYLLPRRGPRL GVRATRKTSERSQPRGRRQPIP-
KARRPEGRTWAQPGYPWPLYGNEGCGWAGWLL-
SPRG
SRPSWGPTDPRRRSRNLGKVIDTLTCGFADLMGYI-
PLVGAPLGGAARALAHGVRVLED GVNYATGN-
LPGCSFSIFLLALLSCLTVPASAYQVRNSSGLY-
HVTNDCPNSSIVYEAAD
AILHTPGCVPCVREGNASRCWVAVTPTVATRDG-

KLPTTQLRRHIDLLVGSATLCSALY VGDLCGSV-
FLVGQLFTFSPRRHWTTQDCNCSIYPGHIT-
GHRMAWDMMMNWSPTAALVV
AQLLRIPQAIMDMIAGAHWGVLAGIAYFSMVGN-
WAKVLVVLLLFAGVDAETHVTGGSA GRTTA-
GLVGLLTPGAKQNIQLINTNGSWHINSTALNC-
NESLNTGWLAGLFYQHKFNSS
GCPERLASCRRLTDFAQGWGPISYANGSGLDERPY-
CWHYPPRPCGIVPAKSVCGPVYC FTPSPV-
VVGTTDRSGAPTYSWGANDTDVFVLNNTRPPLGN-
WFGCTWMNSTGFTKVCGA
PPCVIGGVGNNTLLCPTDCFRKHPEATYSRCGSGP-
WITPRCMVDYPYRLWHYPCTINY TIFKVRMYVG-
GVEHRLEAACNWTRGERCDLEDRDRSELSPLLLST-
TQWQVLPCSFTTL
PALSTGLIHLHQNIVDVQYLYGVGSSIASWAIK-
WEYVVLLFLLLADARVCSCLWMMLL ISQAEAALEN-
LVILNAASLAGTHGLVSFLVFFCFAWYLKGRWVP-
GAVYAFYGMWPLLL
LLLALPQRAYALDTEVAASCGGVVLVGLMALTL-
SPYYKRYISWCMWWLQYFLTRVEAQ LHVWVPPLN-
VRGGRDAVILLMCVVHPTLVFDITKLLLAIFGPL-
WILQASLLKVPYFVR
VQGLLRICALARKIAGGHYVQMAIIKLGALTG-
TYVYNHLTPLRDWAHNGLRDLAVAVE PVVFSRMET-
KLITWGADTAACGDI INGLPVSARRGQEILLG-
PADGMVSKGWRLLAPIT
AYAQQTRGLLGCIITSLTGRDKNQVEGEVQI-
VSTATQTFLATCINGVCWTVYHGAGTR TIASPKG-
PVIQMYTNVDQDLVGWPAPQGSRSLTPCTCGSSD-
LYLVTRHADVIPVRRRG
DSRGSLLSPRPISYLKGSSGGPLLCPAGHAVGL-
FRAAVCTRGVAKAVDFIPVENLETT MRSPVFTDNS-
SPPAVPQSFQVAHLHAPTGSGKSTKVPAAYAAQGYK-
VLVLNPSVAATL
GFGAYMSKAHGVDPNIRTGVRTITTGSPITYSTYGK-
FLADGGCSGGAYDIIICDECHS TDATSILGIGTV-
LDQAETAGARLVVLATATPPGSVTVSHPNIEEVALST-
TGEIPFYGK
AIPLEVIKGGRHLIFCHSKKKCDELAAKLVALGI-
NAVAYYRGLDVSVIPTSGDVVVVS TDALMTGFTGD-
FDSVIDCNTCVTQTVDFSLDPTFTIETTTLPQDAVS-
RTQRRGRTGRG
KPGIYRFVAPGERPSGMFDSSVLCECYDAGCAW-
YELTPAETTVRLRAYMNTPGLPVCQ DHLEF-
WEGVFTGLTHIDAHFLSQTKQSGENFPYLVAYQATV-
CARAQAPPPSWDQMWKC
LIRLKPTLHGPTPLLYRLGAVQNEVTLTHPITKY-
IMTCMSADLEVVTSTWVLVGGVLA ALAAYCLST-
GCVVIVGRIVLSGKPAIIPDREVLYQEFDEMEEC-
SQHLPYIEQGMMLAE
QFKQKALGLLQTASRQAEVITPAVQTNWQKLEVF-
WAKHMWNFISGIQYLAGLSTLPGN PAIASLMA-
FTAAVTSPLTTGQTLLFNILGGWVAAQLAAP-
GAATAFVGAGLAGAAIGSV
GLGKVLVDILAGYGAGVAGALVAFKIMSGEVPST-
EDLVNLLPAILSPGALVVGVVCAA ILRRHVGPGE-
GAVQWMNRLIAFASRGNHVSPTHYVPESDAAARV-
TAILSSLTVTQLLR
RLHQWISSECTTPCSGSWLRDIWDWICEVLSDFK-
TWLKAKLMPQLPGIPFVSCQRGYR GVWRGDGIM-
HTRCHCGAEITGHVKNGTMRIVGPRTCRNMWSGTF-
PINAYTTGPCTPLP
APNYKFALWRVSAEEYVEIRRVGDFHYVSGMTTDN-
LKCPCQIPSPEFFTELDGVRLHR FAPPCKPLLREEVS-
FRVGLHEYPVGSQLPCEPEPDVAVLTSMLTDPSHI-
TAEAAGRRL
ARGSPPSMASSSASQLSAPSLKATCTANHDSPDAEL-
IEANLLWRQEMGGNITRVESEN KVVILDSFDPL-
VAEEDEREVSVPAEILRKSRRFARALPVWARPDYN-
PPLVETWKKPDY
EPPVVHGCPLPPPRSPPVPPPRKKRTVVLTESTLSTA-
LAELATKSFGSSSTSGITGDN TTTSSEPAPSGCPPDSD-
VESYSSMPPLEGEPGDPDLSDGSWSTVSSGADTEDV-
VCCSM
SYSWTGALVTPCAAEEQKLPINALSNSLLRHHN-
LVYSTTSRSACQRQKKVTFDRLQVL DSHYQDV-
LKEVKAAASKVKANLLSVEEACSLTPPHSAKSKFGY-
GAKDVRCHARKAVAH
INSVWKDLLEDSVTPIDTTIMAKNEVFCVQPEKG-
GRKPARLIVFPDLGVRVCEKMALY DVVSKL-
PLAVMGSSYGFQYSPGQRVEFLVQAWKSKKTPMGF-
SYDTRCFDSTVTESDIR
TEEAIYQCCDLDPQARVAIKSLTERLYVGGPLTNSR-
GENCGYRRCRASGVLTTSCGNT LTCYIKARA-
ACRAAGLQDCTMLVCGDDLVVICESAGVQEDAASL-
RAFTEAMTRYSAPP
GDPPQPEYDLELITSCSSNVSVAHDGAGKRVYYL-
TRDPTTPLARAAWETARHTPVNSW LGNIIMFAPTL-
WARMILMTHFFSVLIARDQLEQALNCEIYGA-
CYSIEPLDLPPIIQRL
HGLSAFSLHSYSPGEINRVAACLRKLGVPPLRAW-
RHRARSVRARLLSRGGRAAICGKY LFNWAVRT-
KLKLTPIAAAGRLDLSGWFTAGYSGGDIYHS-
VSHARPRWFWFCLLLLAAG VGIYLLPNR (SEQ ID
NO: 7).

Another aspect of the invention relates to an isolated nucleic acid molecule which encodes a human hepatitis C virus wherein the hepatitis C virus is derived from genotype 1a and is isolate HCV1cc (SEQ ID NO: 1) and has a nucleic acid sequence with 90% sequence identity to isolate HCV1cc (SEQ ID NO: 1).

Another aspect of the invention relates to an isolated nucleic acid molecule which encodes a human hepatitis C virus wherein the hepatitis C virus is derived from genotype 1a and is isolate H77Ccc (SEQ ID NO:3) and has a nucleic acid sequence with 90% sequence identity to isolate H77Ccc (SEQ ID NO:3).

Another aspect of the present invention relates to an isolated nucleic acid molecule which encodes a human hepatitis C virus, wherein said molecule is capable of expressing said virus when transfected into cells, is capable of infectivity in vivo, comprises at least one adaptive mutation in the amino acid sequence of NS3, which is F1464L, comprises at least one adaptive mutation in the amino acid sequence of NS4A which is A1672S, comprises at least one adaptive mutation in the amino acid sequence of NS5B which is D2979G, and at least one additional adaptive mutation in the amino acid sequence selected from the group consisting of S399F, A970T, A1226G, I1312V, I1326V, Q1773H, N1927T, V2198A, I2268T, C2419R, E2622D, A2919T, Y2981F, F2994S, M345T, A828V, L864R, K1052R, S1368P, V1663A, G1909S, M2105V, S2354G, V2417A, V2431I, and F2994R.

Yet another aspect of the present invention is to provide vectors, cells, compositions and viral particles that comprise the nucleic acids sequences of the present invention.

Still other aspects of the present invention are to provide methods for producing a hepatitis C virus particle, for in vitro producing a hepatitis C virus-infected cell, for screening an anti-hepatitis C virus substance and for producing a hepatitis C virus vaccine.

BRIEF DESCRIPTION OF THE FIGURES

FIG. 2 shows effect of individual adaptive mutations on the viability of HCV1cc. RNA transcripts of HCV1cc and HCV1cc with each of eight putative adaptive mutations (named "8m") mutated back to the wild-type sequence were transfected into Huh7.5 cells. J6$^{5'UTR\text{-}NS2}$/JFH1 was used as a positive control. Culture supernatants were collected at the days indicated. (A) HCV infectivity titers (FFU/ml) in supernatants from cultures with ≥80% of the cells found HCV antigen positive by immunostaining, and shown as the mean of triplicate infections±SEM. *, not determined. #, the FFU titers were below the detection limit of $10^{2.4}$ FFU/ml. (B) The HCV supernatant core antigen level as determined by the Architect HCV Ag detection system (Abbott).

HCV1cc, HCV1_LSGF/S399F/TNm/8m. LSGF, F1464L/A1672S/D2979G/Y2981F. TNm, A1226G/Q1773H/N1927T/F2994S.

8m, A970T/I1312V/I11326V/V2198A/I2268T/V2419R/E2622D/A2919T.

FIG. 3 shows identification of adaptive mutations sufficient for the viability of HCV-1 full-length genomes. RNA transcripts from HCV1_LSGF/S399F/TNm recombinant with A970T/A2919T, I1312V/A2919T, C2419R/A2919T, A970T/I1312V/A2919T (designated "3m"), A970T/C2419R/A2919T, I1312V/C2419R/A2919T, and A970T/I1312V/C2419R/A2919T ("4m") were transfected into Huh7.5 cells. The recombinants with A970T/A2919T, I1312V/A2919T, C2419R/A2919T, A970T/C2419R/A2919T, and I1312V/C2419R/A2919T did not spread in the transfection cultures. In contrast, recombinants with "3m" or "4m" spread to ≥80% of the cells during the first week. J6$^{5'UTR\text{-}NS2}$/JFH1 and HCV1cc were used as controls. Culture supernatants were collected at the indicated days. (A) Supernatant HCV infectivity titers (FFU/ml), shown as mean of triplicate infections±SEM. *, not determined. #, the FFU titers were below the detection limit of $10^{2.4}$ FFU/ml. (B) The HCV supernatant core antigen level as determined by the Architect HCV Ag detection system (Abbott). LSGF, F1464L/A1672S/D2979G/Y2981F.

TNm, A1226G/Q1773H/N1927T/F2994S. 3m, A970T/I1312V/A2919T.

4m, A970T/I1312V/C2419R/A2919T.

Figure 4:
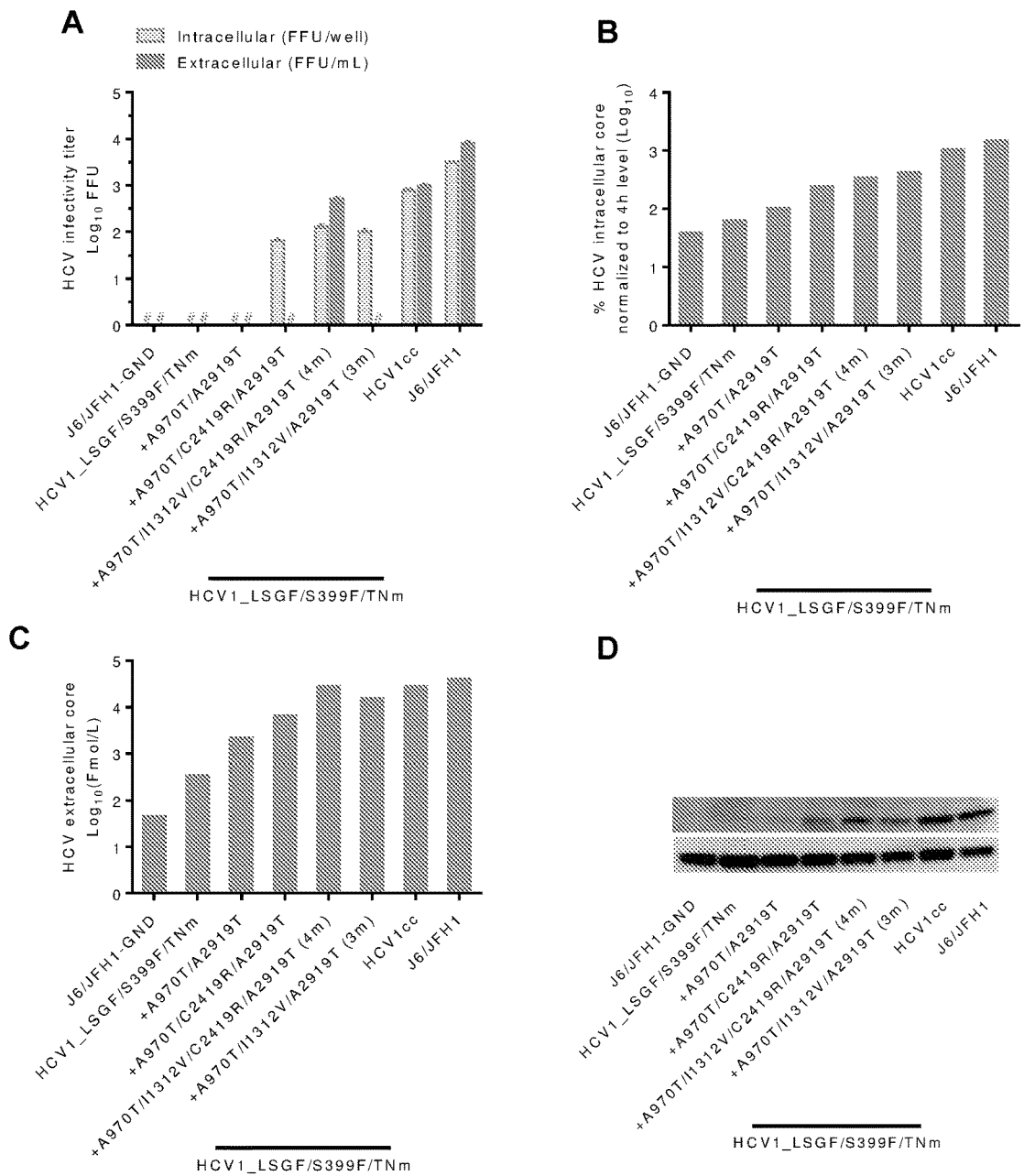

FIG. 4 shows functional analysis of the role of HCV1cc adaptive mutations in the HCV life cycle. RNA transcripts from the indicated recombinants were transfected into HCV entry-deficient S29 cells. All clones contained LSGF/S399F/ TNm plus specific mutations as indicated under each bar graph. Cell lysates were collected at 4 and 48 hours, and culture supernatants were collected at 48 hours. Both intra- and extra-cellular HCV infectivity titers and core levels were determined at 48 hours after transfection. Intracellular core at 4 hours was also determined as a measure of replication independent genome translation following transfection, and used to normalize the 48 hour values. HCV1_LSGF and HCV1_LSGF/TNm were analyzed in a separate experiment (not shown); no intra- and extracellular infectivity titers were detected, and intra- and extracellular core levels were lower than for HCV1_LSGF/S399F/TNm. A replication incompetent form of J6/JFH1 was included in each experiment (J6/JFH1-GND). A) Intracellular and extra-cellular infectivity titers. #, no FFU detected by manual count. Values are expressed as $\log_{10}$ (FFU/mL) for extracellular titers and as $\log_{10}$ (FFU/well) for intracellular infectivity titers. B) Intracellular core levels; the HCV core level at 48 hours was normalized in percentage to the level at 4 hours. C) Extracellular core levels, expressed as $\log_{10}$ (Fmol/mL). D) Western blots. Cell lysates harvested 48 hours post-transfection were separated through acrylamide gels and proteins were transferred to PVDF membranes (see Materials and Methods). Immunoblot was performed with anti-HCV core C7-50 for detection of HCV core and anti-actin for detection of host-cell actin.

FIG. 5 shows viability of adapted H77C in Huh7.5 cells. RNA transcripts of H77C full-length recombinants with the indicated mutations were transfected into Huh7.5 cells, and cultures were monitored for HCV core/NS5A antigens by immunostaining. Cell-free transfection supernatants collected from peak infection were passaged to naïve Huh7.5 cells (first-passage) and after viral spread, the culture supernatant of first-passage was subsequently used to infect naïve Huh7.5 cells (second-passage). HCV infectivity titers in culture supernatant are shown as mean FFU/ml of triplicate infections±SEM. (A) Transfection and passage of H77 full-length virus H77C_LSGF/TNmr/S1368P. (B) Transfection and passage of H77Ccc. J6/JFH1 was used as a positive control.

H77Ccc, H77C_LSGF/TNmr/S1368P/10m.
LSGF, F1464L/A1672S/D2979G/Y2981F.
TNmr, A1226G/Q1773H/N1927T/F2994R.
10m, M345T/A828V/L864R/K1052R/V1663A/G1909S/M2105V/S2354G/V2417A/V2431I.

FIG. 6 [table 1 (FIG. 6)] shows characteristics of the HCV-1 5'UTR-NS5A (5-5A) recombinant and full-length viruses in Huh7.5 cell cultures. One milliliter of transfection- or first passage-recovered supernatant was used for subsequent infection of cells grown in 6-well-plates.

a, the first- and second-passage viruses were sequenced (FIG. 7).

b, the viruses collected at day 8, 10, and 12 were pooled and used for analysis.

c, the third-passage virus reached 4.2 log 10 FFU/ml at day 6.

d, in two other independent transfections, HCV1cc produced 3.8-4.0 log 10 FFU/ml at day 5.

TN$_{GH}$, A1226G/Q1773H.
LSG, F1464L/A1672S/D2979G.
LSGF, F1464L/A1672S/D2979G/Y2981F.
TNm, A1226G/Q1773H/N1927T/F2994S.
8m, A970T/I1312V/I11326V/V2198A/I2268T/C2419R/E2622D/A2919T.
4m, A970T/I1312V/C2419R/A2919T.
nd, not done.
-, not applicable FIG. 7 [table 2 (FIG. 7)] shows ORF sequence analysis of HCV-1 5'UTR-NS5A (5-5A) viruses. Shadings indicate the engineered mutations; LSG mutations (F1464L/A1672S/D2979G) are indicated in white letters with black background, TN-derived mutations are in dark shading, and S399F identified in this study is in light shading. Coding changes are shown; the capital/capital letters indicate a 50/50 nucleotide quasispecies, while the capital/lowercase letters indicates a dominant/minor ratio. Dots indicate identity with the original plasmid sequence.

a, the virus had a non-coding nucleotide change T5750C.

b, the viruses collected at day 8, 10, and 12 were pooled and used for analysis; the recovered sequence contained non-coding nucleotide changes T4868C/t, T5750C, and T6251T/C.

c, the virus acquired a non-coding nucleotide change C6131C/T.

$TN_{GH}$, A1226G/Q1773H.

Figure 1:
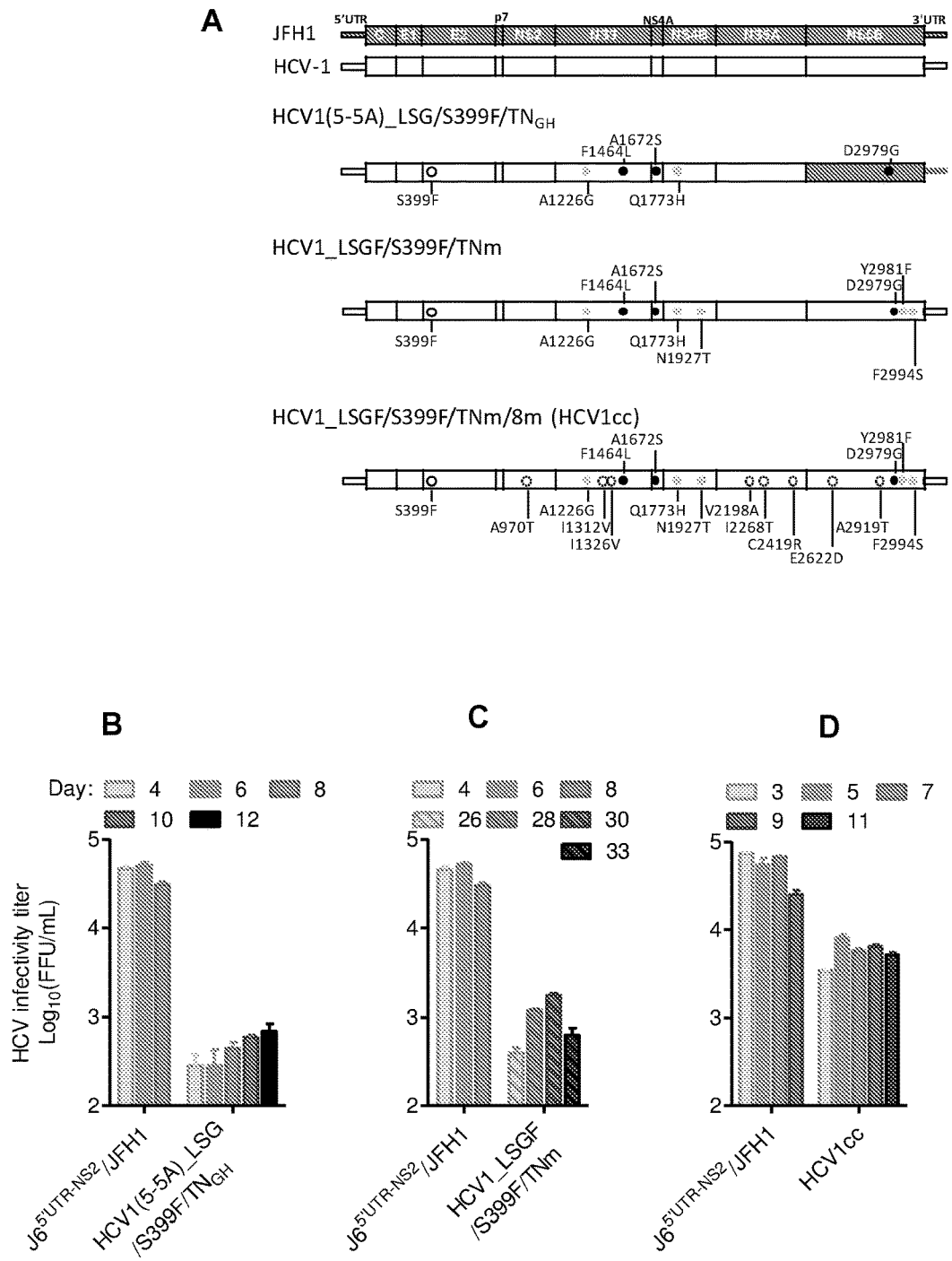
FIG. 1 shows viability of HCV-1 5'UTR-NS5A (5-5A) and full-length recombinants in Huh7.5 cells. (A) Schematic diagrams of HCV genomes. LSG mutations (F1464L/A1672S/D2979G) previously identified from J6 and JFH1 recombinants are highlighted by black dots, additional TNcc-adaptive mutations (TNm) are indicated by gray dots, S399F from HCV-1 5-5A recombinant is indicated by a circle, and eight mutations identified from passaged full-length HCV-1 viruses ("8m") are indicated by broken circles. (B-D) RNA transcripts of HCV-1 5-5A and full-length recombinants with the indicated mutations were transfected into Huh7.5 cells, and cultures were monitored for HCV core/NS5A antigens by immunostaining. HCV infectivity titers in culture supernatant collected at the days indicated, after ≥80% of the cells were found HCV antigen positive, were determined by FFU assays, and shown as mean of triplicate infections±SEM. J6$^{5'UTR\text{-}NS2}$/JFH1 was used as a positive control. LSGF, F1464L/A1672S/D2979G/Y2981F. TN$_{GH}$, combination of two TNcc-adaptive mutations A1226G/Q1773H. TNm, combination of four TNcc-adaptive mutations A1226G/Q1773H/N1927T/F2994S. HCV1cc, HCV1_LSGF/S399F/TNm/8m, in which "8m" indicates the mutations A970T/I1312V/I1326V/V2198A/I2268T/V2419R/E2622D/A2919T.

FIG. 8 [table 3 (FIG. 8)] shows ORF sequence analysis of HCV-1 full-length viruses. The in vivo viable HCV-1/SF9_A (GenBank accession number AF271632) engineered with LSGF (F1464L/A1672S/D2979G/Y2981F), S399F identified from HCV-1 5-5A recombinant (FIG. 7), and TNm (A1226G/Q1773H/N1927T/F2994S) was adapted for growth in transfected Huh7.5 cells. Eight mutations (A970T/I1312V/I1326V/V2198A/I2268T/V2419R/E2622D/A2919T, designated "8m") were identified from passaged HCV1_LSGF/S399F/TNm viruses and were engineered back to the genome to make HCV1_LSGF/S399F/TNm/8m, designated "HCV1cc". The HCV1cc genome, containing seventeen mutations, showed efficient virus spread in tranfection cultures and released infectious virus particles with HCV infectivity titers of $10^{3.8}$ FFU/ml (FIG. 1). A HCV-1 full-length virus, HCV1_LSGF/S399F/TNm/4m ("4m", A970T/I1312V/C2419R/A2919T) replicated efficiently in the culture, with infectivity close to those of HCV1cc. The HCV-1 full-length viruses were passaged to naïve Huh7.5 cells, the viruses spread efficiently, and the culture supernatant were collected at indicated time-points for sequence analysis.

Shadings indicate the engineered mutations; LSGF mutations are indicated in white letters with black background, TNcc-derived mutations (TNm) are in dark shading, and mutations identified in this study are in light shading.

a, the constructed plasmid contained a non-coding nucleotide change C3210A, which was maintained in the passage-recovered viruses. The second- and third-passage viruses acquired non-coding nucleotide changes T2408C and C2765T.

b, no non-coding change was found in ORF sequence analysis.

FIG. 9 [table 4 (FIG. 9)] shows ORF sequence analysis of H77C full-length viruses. The in vivo viable H77C genome engineered with ten nucleotides changes (resulting in nine amino acid changes, as nucleotides 9321 and 9322 are in the same codon, see "b" below), named H77C_LSGF/TNmr/S1368P (see below), had low level replication after transfection of Huh7.5 cells and spread to most culture cells at day 96. Ten mutations ("10m") was identified from H77C_LSGF/TNmr/S1368P, and engineered into the genome to make H77Ccc. The H77Ccc genome, which had a total of nineteen amino acid changes, showed efficient virus spread in tranfection- and infection-cultures, and released infectious virus particles with HCV infectivity titers of $10^{3.5}$-$10^{4.4}$ FFU/ml (FIG. 5). The H77C full-length viruses were passaged to naïve Huh7.5 cells, the viruses spread to ≥80% of culture cells, within three days for H77Ccc and within 8 days for H77C_LSGF/TNmr/S1368P, and then the culture supernatants were collected for sequence analysis. Shadings indicate the engineered mutations; LSGF mutations (LSG, F1464L/A1672S/D2979G; F, Y2981F) are indicated in white letters with a black background, TNcc-adaptive mutations (TNm) are in dark shading, and mutations identified in this study are in light shading.

a, mutation S1368P was previously identified from H77C and HCV-1 (FIG. 7) 5-5A recombinant viruses; the first- and second-passage H77C_LSGF/TNmr/S1368P viruses both acquired non-coding nucleotide changes A2558G, A3089G, G3860A, C4403T, T4904C, A6437G, A6713G, A7727G, A8804G, and T9227C.

b, nucleotides 9321 and 9322 are in the same codon for F2994R change.

H77Ccc, H77C_LSGF/TNmr/S1368P/10m.

LSGF, F1464L/A1672S/D2979G/Y2981F.

TNmr, A1226G/Q1773H/N1927T/F2994R (the F2994R was identified from a LSGF-adapted TN full-length virus, see Results for details).

"10m", M345T/A828V/L864R/K1052R/V1663A/G1909S/M2105V/S2354G/V2417A/V2431I.

The present invention will now be described in more detail in the following.

DETAILED DESCRIPTION OF THE INVENTION

The present invention advantageously provides hepatitis C virus (HCV) nucleotide sequences capable of replication, expression of functional HCV proteins, and infection in vivo and in vitro for development of antiviral therapeutics and diagnostics.

Nucleic acid molecules (cDNA clones and RNA transcripts)

The genomes of the different HCV genotypes have been standardized in a numbering system for HCV nucleotides, proteins and epitopes.

This work was done in an expert meeting and published in Kuiken et al., Hepatology, November 2006, page 1355-61.

This numbering system allows comparison of genes across genotypes with consistency and with an unambiguous method for referring to amino acid substitutions for specific positions in genes encoded by the HCV genome.

The numbering used in the present application uses this numbering system and with reference to the H77 reference sequence with GenBank accession number AF009606 used in Kuiken et al.

Thus, when no other statement is made will a specific number of a specific genotype refer to the H77 reference sequence with GenBank accession number AF009606.

In a broad aspect, the present invention is directed to an isolated nucleic acid molecule which encodes a human hepatitis C virus, wherein said molecule is capable of expressing said virus when transfected into cells, is capable of infectivity in vivo, comprises at least one adaptive mutation in the amino acid sequence of NS3, which is F1464L, comprises at least adaptive mutation in the amino acid sequence of NS4A which is A1672S, and comprises at least one adaptive mutation in the amino acid sequence of NS5B which is D2979G, and at least one additional adaptive mutation in the amino acid sequence selected from the group consisting of S399F, A970T, A1226G, I1312V, I1326V, Q1773H, N1927T, V2198A, I2268T, C2419R, E2622D, A2919T, Y2981F, F2994S, M345T, A828V, L864R, K1052R, S1368P, V1663A, G1909S, M2105V, S2354G, V2417A, V2431I, and F2994R according to the H77 reference sequence with GenBank accession number AF009606.

The adaptive mutations as shown above means that in the case of F1464L is phenylalanine at amino acid position 1464 changed to Leucine.

The original amino acids F1464, A1672, and D2979 (H77 reference numbers) at LSG positions are highly conserved across all HCV genotypes.

In one embodiment the present invention comprises the nucleic acid molecule with a shortened 3' UTR region.

A shortened 3' UTR region refers to any 3' UTR region wherein one or more nucleotides have been deleted. The present inventors have previously exemplified such shortened 3'UTR region by a 33 U deletion in the 3'UTR (Δ33U).

In another embodiment of the present invention the human hepatitis C virus is of a genotype selected from the group consisting of 1a, 1b, 2a, 2b, 2c, 3a, 4a, 4d, 5a, 6a and 7a.

The terms "isolate" and "strain" are used herein interchangeably.

In a preferred embodiment of the present invention the human hepatitis C virus is a strain of genotype 1a.

In a preferred embodiment of the present invention the human hepatitis C virus is a strain of genotype 2a or 2b.

In another preferred embodiment of the present invention the human hepatitis C virus is a strain of genotype 2a.

In another preferred embodiment of the present invention the human hepatitis C virus is a strain of genotype 2b.

In another preferred embodiment of the present invention the hepatitis C virus is of genotype 1a and is isolate HCV1cc (SEQ ID NO: 1).

In another preferred embodiment of the present invention the hepatitis C virus is of genotype 1a and is isolate HCV-1_LSGF/S399F/TNm/4m (SEQ ID NO:2).

In another preferred embodiment of the present invention the hepatitis C virus is of genotype 1a and is H77Ccc (SEQ ID NO:3).

The hepatitis C virus can in some embodiments of the present invention comprise further adaptive mutations.

In one embodiment the present invention comprises the hepatitis C virus and at least six further adaptive mutations, such as five, such as four, such as three, such as two, such as one.

The adaptive LSG mutations F1464L/A1672S/D2979G are according to the H77 reference sequence with GenBank accession number AF009606. The work has been published as Li et al., Proc Natl Acad Sci USA. 2012 May 1; 109(18): E1101-10. Also see Author Summary in Proc Natl Acad Sci USA on page 6806 (volume 109, number 18).

The present inventors have identified a wide variety of recombinants that generated different virus viability.

In an embodiment of the present invention are these sequences isolated nucleic acid sequences and amino acid sequence, respectively.

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100).

In one embodiment the two sequences are the same length.

In another embodiment the two sequences are of different length and gaps are seen as different positions.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

An embodiment of the present invention thus relates to sequences of the present invention that has some degree of sequence variation.

One embodiment relates to HCV1cc (SEQ ID NO: 1) in which the nucleic acid molecule comprises the nucleic acid sequence with a sequence identity of at least 80% to that of HCV1cc (SEQ ID NO: 1).

In another embodiment, the nucleic acid comprises a sequence sharing at least 85% identity with that set forth in HCV1cc (SEQ ID NO: 1), such as 90% identity, 91% identity, 92% identity, 93% identity, 94% identity, 95% identity, 96% identity, 97% identity, 98% identity, or 99% identity.

Another embodiment relates to HCV-1_LSGF/S399F/TNm/4m (SEQ ID NO:2) in which the nucleic acid molecule comprises the nucleic acid sequence with a sequence identity of at least 80% to that of HCV-1_LSGF/S399F/TNm/4m (SEQ ID NO:2).

In another embodiment, the nucleic acid comprises a sequence sharing at least 85% identity with that set forth in HCV-1_LSGF/S399F/TNm/4m (SEQ ID NO:2), such as 90% identity, 91% identity, 92% identity, 93% identity, 94% identity, 95% identity, 96% identity, 97% identity, 98% identity, or 99% identity.

Yet another embodiment relates to H77Ccc (SEQ ID NO:3) in which the nucleic acid molecule comprises the nucleic acid sequence with a sequence identity of at least 80% to that of H77Ccc (SEQ ID NO:3).

In another embodiment, the nucleic acid comprises a sequence sharing at least 85% identity with that set forth in H77Ccc (SEQ ID NO:3), such as 90% identity, 91% identity, 92% identity, 93% identity, 94% identity, 95% identity, 96% identity, 97% identity, 98% identity, or 99% identity.

It should be noted that while several of the sequences in the present application (SEQ ID NOs: 1-3) are DNA sequences (SEQ ID NOs: 4-6 are amino acid sequences), the present invention contemplates the corresponding RNA sequence, and DNA and RNA complementary sequences as well.

In another preferred embodiment of the present invention the hepatitis C virus is of genotype 1a and is isolate HCV1cc (SEQ ID NO:4).

In another preferred embodiment of the present invention the hepatitis C virus is of genotype 1a and is isolate HCV-1_LSGF/S399F/TNm/4m (SEQ ID NO:5).

In another preferred embodiment of the present invention the hepatitis C virus is of genotype 1a and is H77Ccc (SEQ ID NO:6).

One embodiment relates to HCV1cc (SEQ ID NO:4) in which the amino acid molecule comprises the amino acid sequence with a sequence identity of at least 80% to that of HCV1cc (SEQ ID NO:4).

In another embodiment, the amino acid comprises a sequence sharing at least 85% identity with that set forth in HCV1cc (SEQ ID NO:4), such as 90% identity, 91% identity, 92% identity, 93% identity, 94% identity, 95% identity, 96% identity, 97% identity, 98% identity, or 99% identity.

Another embodiment relates to HCV-1_LSGF/S399F/TNm/4m (SEQ ID NO:5) in which the amino acid molecule comprises the amino acid sequence with a sequence identity of at least 80% to that of HCV-1_LSGF/S399F/TNm/4m (SEQ ID NO:5).

In another embodiment, the amino acid comprises a sequence sharing at least 85% identity with that set forth in HCV-1_LSGF/S399F/TNm/4m (SEQ ID NO:5), such as 90% identity, 91% identity, 92% identity, 93% identity, 94% identity, 95% identity, 96% identity, 97% identity, 98% identity, or 99% identity.

Yet another embodiment relates to H77Ccc (SEQ ID NO:6) in which the amino acid molecule comprises the amino acid sequence with a sequence identity of at least 80% to that of H77Ccc (SEQ ID NO:6).

In another embodiment, the amino acid comprises a sequence sharing at least 85% identity with that set forth in H77Ccc (SEQ ID NO:6), such as 90% identity, 91% identity, 92% identity, 93% identity, 94% identity, 95% identity, 96% identity, 97% identity, 98% identity, or 99% identity.

Thus, in cases where a DNA sequence is mentioned refers such DNA sequence also to the RNA equivalent i.e. with Ts exchanged with Us as well as their complimentary sequences.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to the sequences of the present invention.

Various modifications for example of the 5' and 3' UTR are also contemplated by the invention.

In another embodiment, the nucleic acid further comprises a reporter gene, which, in one embodiment, is a gene encoding neomycin phosphotransferase, *Renilla* luciferase, secreted alkaline phosphatase (SEAP), *Gaussia* luciferase or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA.

Thus, where particular sequences of nucleic acids of the invention are set forth, both DNA and corresponding RNA are intended, including positive and negative strands thereof.

In a further embodiment, the nucleic acid sequences or the nucleic acid sequences with any mutation described in this document is obtained by any other means than what is described above.

Nucleic acid molecules according to the present invention may be inserted in a plasmid vector for translation of the corresponding HCV RNA. Thus, the HCV DNA may comprise a promoter 5' of the 5'UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

Thus, in one embodiment the present invention provides a cassette vector for cloning viral genomes, comprising, inserted therein, the nucleic acid sequence according to the invention and having an active promoter upstream thereof.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The present inventors here report adaptive mutations, which allow efficient formation and release of viral particles in cell culture, and thus the present invention relates to these adaptive mutations in the present use as well as use in other strains by changing equivalent positions of such genomes to the adapted nucleotide or amino acid described.

A group of preferred HCV-cDNA constructs, HCV-RNA full-length genomes with the ability to release viral particles in cell culture, which are consequently highly suitable for practical use, is characterized in that it contains one, several or all of the nucleic acid exchanges listed below and/or one or several or all of the following amino acid exchanges.

One embodiment of the present invention relates to adaptive mutations, wherein the adaptive mutation is a mutation that can be observed by clonal or direct sequencing of recovered replicating genomes of the sequences of the present invention.

Thus in a further embodiment, the present invention relates to nucleic acid molecules according to the present invention, wherein said molecule comprises one or more adaptive mutations in p7, NS2, NS3, NS4A, NS4B, NS5A or NS5B singly or in combination.

In the context of the present invention the term "adaptive mutation" is meant to cover mutations identified in passaged viruses that provide the original and any other HCV sequence the ability to grow efficiently in culture. Furthermore all introductions of mutations into the sequences described, whether or not yielding better growth abilities, and the introduction of these mutations into any HCV sequence should be considered.

Thus the described mutations enable the HCV-RNA genome (e.g. derived from a HCV-cDNA clone) to form viral particles in and release these from suitable cell lines. In addition some of the described mutations might change the function of the concerned proteins in favourable ways, which might be exploited in other experimental systems employing these proteins.

This also includes other HCV genomes with adaptive mutations, all of them, combinations of them or individual mutations that grow in culture.

It should be understood that any feature and/or aspect discussed above in connection with the mutations according to the invention apply by analogy to both single mutations and any combination of the mutations.

In another embodiment all the amino acid changes observed herein are provided by the present application. The skilled addressee can easily obtain the same amino acid change by mutating another base of the codon and hence all means of obtaining the given amino acid sequence is intended.

Titer

To determine the efficiency of the developed system, HCV RNA titers are determined in IU/ml (international units/ml) with Taq-Man Real-Time-PCR and infectious titers are determined with a 50% tissue culture infectious dose method. This titer shows the dilution of the examined viral stock, at which 50% of the replicate cell cultures used in the essay become infected and is given in TCID50/ml.

Alternatively the infectious titers are determined as FFU/ml (focus forming unites/ml); in such method, infectivity titers are determined by infection of cell culture replicates with serial dilutions of virus containing supernatants and, following immuno-stainings for HCV antigens, counting of HCV-antigen positive cell foci.

HCV RNA titers and infectivity titers can be determined extracellularly, in cell culture supernatant (given as IU and TCID50 or FFU per ml, respectively) or intracellularly, in lysates of pelleted cells (given as IU and TCID50 or FFU related to a the given cell number or culture plate wells, which was lysed).

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ TCID50/ml or above following transfection and/or subsequent viral passage, such as a titer of at least $10^3$ TCID50/ml, such as a titer of at least $10^4$ TCID50/ml, such as a titer of at least $10^5$ TCID50/ml, such as a titer of at least $10^6$ TCID50/ml, such as a titer of at least $10^7$ TCID50/ml, such as a titer of at least $10^8$ TCID50/ml, such as a titer of at least $10^9$ TCID50/ml or such as a titer of at least $10^{10}$ TCID50/ml.

It is of course evident to the skilled addressee that the titers described here are obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term “composition” refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

“Pharmaceutically acceptable” refers to molecular entities and compositions that are physiologically tolerable and do not typically produce an allergic or similar untoward reaction, such as gastric upset, dizziness and the like, when administered to a human. Preferably, as used herein, the term “pharmaceutically acceptable” means approved by a regulatory agency of the Federal or a state government or listed in the U.S. Pharmacopoeia or other generally recognized pharmacopoeia for use in animals, and more particularly in humans.

The term “excipient” refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response.

Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvmm*.

Preferably, the adjuvant is pharmaceutically acceptable.

Thus relates one embodiment of the present invention to a composition comprising a nucleic acid molecule according to the present invention suspended in a suitable amount of a pharmaceutical acceptable diluent or excipient.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus relates one embodiment of the present invention to a cell comprising the nucleic acid according to the present invention, the composition of present invention or the cassette vector of the present invention.

Another embodiment of the present invention relates to a method for producing a cell, which replicates human hepatitis C virus and produces a virus particle comprising introducing a nucleic acid molecule of the present invention into a cell.

In a preferred embodiment is the cell is a Huh7.5 cell.

Another embodiment of the present invention relates to a cell obtainable by the methods of the present invention.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, -4, -6 or -9 and the low-density lipid receptor.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) may be used for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV, which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

In one embodiment the introduced mutations attenuates the virus in vivo.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

In one embodiment, the method further comprises isolating infectious HCV. In another embodiment, the method further comprises freezing aliquots of said infectious HCV.

According to this aspect of the invention, and in one embodiment, the HCV is infectious following thawing of said aliquots, and in another embodiment, the HCV is infectious following repeated freeze-thaw cycles of said aliquots.

A further embodiment of the present invention relates to a method for in vitro producing a hepatitis C virus-infected cell comprising culturing a cell according to the present invention and infecting other cells with the produced virus particle in the culture.

Screening for Anti-Viral Drugs and the Determination of Drug Resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Alternatively, the number of antigen-expressing cells is determined. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present invention may prove useful for different research topics.

The systems developed in this invention are ideal candidates for specific testing of therapeutics in general and therapeutics targeting viral entry, assembly and release.

Genomes with the sequences of the present invention are valuable for testing of neutralizing antibodies and other drugs acting on entry level, such as fusion inhibitors.

In one embodiment the present invention relates to a method for identifying neutralizing antibodies.

In another one embodiment the present invention relates to a method for identifying cross-genotype neutralizing antibodies.

In one embodiment the present invention relates to a method of raising neutralizing antibodies.

In another embodiment the present invention relates to a method of raising cross neutralizing antibodies.

In one embodiment the present invention related to a method for screening new HCV genotype 1a, 1b, 2a, 2b, 2c, 3a, 4a, 4d, 5a, 6a and/or 7a inhibitors or neutralizing antibodies, comprising a) culturing at least one selected from the group consisting of a cell according to the present invention, a hepatitis C virus infected cell according to the present invention and a hepatitis C virus particle obtainable by the present invention together with a hepatitis C virus permissive cell, and b) subjecting said virus or virus infected cell culture to a blood sample or derivatives thereof from a HCV genotype 1a, 1b, 2a, 2b, 2c, 3a, 4a, 4d, 5a, 6a and/or 7a infected patient c) detecting the amount of replicating RNA and/or the virus particles.

Inhibitors targeting the HCV non-structural proteins NS3/4A, NS5A and NS5B are currently being developed. The first directly-acting antiviral compounds targeting the NS3/

4A protease were licensed in 2011 (Telaprevir and Boceprevir). Clinical phase studies show promising results for inhibitors of NS5A and the NS5B polymerase. The present invention offers novel culture systems where additional HCV isolates can be tested to generate efficient cross-reactive inhibitors.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. Hence, new compounds targeting the putative p7 ion-channel and autoprotease inhibitors interfering with NS2, and drugs targeting cellular proteins involved in the described processes can be tested.

Thus, one embodiment of the present invention relates to a method for screening an anti-hepatitis C virus substance, comprising
  a) culturing at least one selected from the group consisting of a cell according to the present invention, a hepatitis C virus infected cell according to the present invention and a hepatitis C virus particle obtainable by the present invention together with a hepatitis C virus permissive cell,
  b) subjecting said virus or virus infected cell culture to the anti-hepatitis C virus substance, and
  c) detecting the replicating RNA and/or the virus particles in the resulting culture.

Another embodiment of the present invention relates to a method for screening an anti-hepatitis C virus substance, comprising
  a) culturing at least one selected from the group consisting of a cell according to the present invention and the hepatitis C virus particle according to the present invention together with a hepatitis C virus permissive cell, and
  b) detecting the replicating RNA or the virus particles in the resulting culture.

Yet another embodiment of the present invention relates to a hepatitis C vaccine comprising a hepatitis C virus particle of the present invention or a part thereof.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labelled for easier detection, including radio-labelled, antibody labelled for fluorescently labelled molecules, which may be detected by any means well known to one skilled in the art.

In one embodiment, the candidate molecule is an antibody.

Another embodiment of the present invention relates to an antibody against the hepatitis C virus particle of the present invention.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modelling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 µM in an in vitro assay for at least one step in infection, replication, or pathogenesis of HCV, more preferably from about 0.0001 nM to 75 µM, more preferably from about 0.0001 nM to 50 µM, more preferably from about 0.0001 nM to 25 µM, more preferably from about 0.0001 nM to 10 µM, and even more preferably from about 0.0001 nM to 1 µM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology shows a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew *Tupaia belangeri chinensis*. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The cell culture system developed of the present invention will be a valuable tool to address different research topics.

It will allow the isolate, subtype and genotype specific study of functions of all HCV genome regions and proteins using reverse genetics.

Accordingly the developed cell culture systems allow individual patient targeting. This means that when a new potential therapeutic candidate is discovered it is possible to test this particular candidate or combination of candidates on novel HCV isolates grown in culture.

Knowing which specific genotype the candidate is functioning towards, it allows an individual treatment of each patient dependent on which specific genotype the patient is infected with. Furthermore these cell culture systems allow the development of antibodies and vaccines targeting individual patients.

The replication level of a virus can be determined, in other embodiments, using techniques known in the art, and in other embodiments, as exemplified herein. For example, the genome level can be determined using RT-PCR, and northern blot. To determine the level of a viral protein, one can use techniques including ELISA, immunoprecipitation, immunofluorescence, EIA, RIA, and Western blotting analysis.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus shows the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus shows that the HCV variant has improved growth in cell culture.

In some embodiments, HCV variants are selected for enhanced replication, over a long course of time, in vitro culture systems. According to this aspect of the invention, and in some embodiments, cells contacted with the variants are characterized by reduced infection, as compared to cells contacted with the chimeric HCV.

Kits

In a related aspect, the invention also provides a test kit for HCV comprising HCV virus components, and a diagnostic test kit for HCV comprising components derived from an HCV virus as described herein.

Furthermore the invention also provides test kits, for screening for new HCV inhibitors, neutralizing and cross neutralizing antibodies, comprising HCV virus components.

A further aspect of the present invention relates to a method for obtaining an isolated nucleic acid molecule encoding a human hepatitis C virus with adaptive mutations, comprising identification of one or more adaptive mutations as described in the above method, incorporation of said one or more adaptive mutations into a nucleic acid molecule encoding a full length human hepatitis C virus, and isolating the nucleic acid molecule encoding a human hepatitis C virus with adaptive mutations.

One embodiment of the present invention relates to an isolated nucleic acid molecule obtained from the above method.

Another embodiment of the present invention relates to an isolated nucleic acid molecule according to the present invention, wherein the human hepatitis C virus is of a genotype selected from the group consisting of 1a, 1b, 2a, 2b, 2c, 3a, 4a, 4d, 5a, 6a and 7a.

EXAMPLES

Abstract

The first discovered and sequenced hepatitis C virus (HCV) genome and the first in vivo infectious HCV clones originated from the HCV prototype strains HCV-1 and H77, respectively, both widely used in research of this important human pathogen. In the present study, we developed efficient infectious cell-culture systems for these genotype 1a strains by using the HCV-1/SF9_A and H77C in vivo infectious clones. We initially adapted a genome with the HCV-1 5'UTR-NS5A and the JFH1 NS5B-3'UTR (5-5A recombinant), including the genotype 2a-derived mutations F1464L/A1672S/D2979G (LSG), to grow efficiently in Huh7.5 cells, thus identifying the E2 mutation S399F. Combination of LSG/S399F and reported TNcc(1a)-adaptive mutations A1226G/Q1773H/N1927T/Y2981F/F2994S promoted adaptation of the full-length HCV-1 clone. An HCV-1 recombinant with seventeen mutations (HCV1cc) replicated efficiently in Huh7.5 cells, and produced supernatant infectivity titers of $10^{4.0}$ focus-forming-units (FFU)/ml. Eight of these mutations were identified from passaged HCV-1 viruses, and the A970T/I1312V/C2419R/A2919T mutations were essential for infectious particle production. Using CD81-deficient Huh7 cells, we further demonstrated the importance of A970T/I1312V/A2919T or A970T/C2419R/A2919T for virus assembly and that the I1312V/C2419R combination played a major role in virus release. Using a similar approach, we found that NS5B mutation F2994R identified here from culture-adapted full-length TN-viruses and a common NS3-helicase mutation (S1368P) derived from viable H77C and HCV-1 5-5A recombinants initiated replication and culture-adaptation of H77C containing LSG and TNcc(1a)-adaptive mutations. An H77C recombinant harbouring nineteen mutations (H77Ccc) replicated and spread efficiently after transfection and subsequent infection of naïve Huh7.5 cells, reaching titers of $10^{3.5}$ and $10^{4.4}$ FFU/ml, respectively.

Importance

Hepatitis C virus (HCV) was discovered in 1989 with the cloning of the HCV-1 genome. In 1997, two molecular clones of H77, the other HCV prototype strain, were shown to be infectious in chimpanzees, but not in vitro. HCV research was hampered by a lack of infectious cell-culture systems, which became available only in 2005 with the discovery of JFH1 (genotype 2a), a genome that could establish infection in Huh7.5 cells. Recently, we developed in vitro infectious clones for genotype 1a (TN), 2a (J6), and 2b (J8, DH8, and DH10) strains by identifying key adaptive mutations. Globally, genotype 1 is the most prevalent. Studies using HCV-1 and H77 prototype sequences have generated important knowledge on HCV. Thus, the in vitro infectious clones developed here for these 1a strains will be of particular value in advancing HCV research. Moreover, our findings open new avenues for the culture adaptation of HCV isolates of different genotypes.

INTRODUCTION

Hepatitis C virus (HCV) has chronically infected over 130 million people worldwide and is a leading cause of liver fibrosis, cirrhosis, and hepatocellular carcinoma. More than 350,000 deaths annually are due to HCV-related liver diseases (World Health Organization website, 2014). HCV belongs to the Hepacivirus genus within the Flaviviridae family, and its genome is a positive-sense single-strand RNA of ~9.6-kb consisting of a single open reading frame (ORF) and 5' and 3' untranslated regions (UTRs). The ORF encodes viral structural proteins (Core and envelope glycoproteins E1 and E2), a small membrane protein (p7), and six non-structural proteins (NS2, NS3, NS4A, NS4B, NS5A, and NS5B). HCV has been classified in 7 major genotypes differing in nucleotide and amino acid sequences by ~30% and numerous subtypes with sequence heterogeneity of 15-20%. Genotype 1 accounts for the majority of HCV infections worldwide, and subtypes 1a and 1b are predominant. Furthermore, genotype 1 strains were found to be relatively resistant to interferon-α/ribavirin therapy. Although incorporation of directly acting antivirals (DAA) improves the sustained virological response rate, emergence of drug resistance is a concern and may influence the outcome of these new therapies.

Robust infectious HCV cell culture systems from isolates of different genotypes represent valuable tools for the in vitro study of HCV genetic heterogeneity, which plays a major role in disease progression, response to antiviral therapy, and poses a significant challenge for vaccine development. Since the discovery of HCV-1 in 1989, many attempts have been directed to adapt prototype strains of HCV to grow in cell culture. However, success did not come until 2005 when the cloned JFH1 (genotype 2a) full-length sequence was found to be able to spontaneously establish infection in hepatoma Huh7 cells and derivatives.

To date, JFH1 remains the only cloned HCV sequence reported with spontaneous growth in vitro. Recently, we identified three mutations in NS3, NS4A, and NS5B (F1464L, A1672S, and D2979G, respectively—the LSG mutations) [nucleotide and amino acid numbering throughout is according to the H77 (1a) reference sequence, GenBank accession number AF009606] that enabled adaptation of HCV full-length genomes in cell culture. These mutations lead to the development of robust and highly infectious full-length cell culture systems for HCV genotype 1a (TNcc), 2a (J6cc), and 2b (J8cc, DH8cc, and DH10cc) strains; the TNcc represented the first effective cell culture system for genotype 1. Infectious culture systems were only reported for a few other genotype 1 and 2 strains.

The HCV-1 strain was the first HCV genome to be cloned and has been a key tool commonly used by investigators in the HCV field. Studies using HCV-1 have led to important discoveries, such as elucidation of the genetic organization of the HCV genome, identification of CD81 as an important viral receptor, and discovery of the frame-shifted F protein.

An HCV-1 E1/E2-based vaccine was found to induce a neutralizing antibody responses with cross-reactivity against various HCV genotypes in rodents, chimpanzees, and humans, thus making it a promising vaccine candidate for further development. H77 is another genotype 1a strain that has significantly contributed to HCV research. H77 is the reference sequence for HCV genome numbering. The RNA transcripts of two H77 full-length cDNA clones, named H77C and H77, were the first HCV genomes found to be infectious, as demonstrated by intrahepatic transfections in chimpanzees. Patient serum-derived H77 virus was reported to be able to replicate in lymphoblastoid cell lines at low levels, and could be passaged to chimpanzees. Subsequently, studies using the sequences of H77 contributed greatly to HCV research, for example, to the study of viral entry using HCV-like particles and to the development of HCV pseudo-particles, the selection of highly permissive Huh7.5 cells, and the discovery of the importance of microRNA miR-122 in HCV replication. Efforts to propagate H77 in cell culture have been reported, using different cell lines, and H77C harboring mutations derived from its replicon (designated H77-S) could release infectious virus particles. Given the historical importance of HCV-1 and H77 isolates in HCV research, efficient infectious cell culture systems for these isolates would be very valuable tools for studies on HCV.

In this study, we developed robust and efficient infectious cell culture systems for HCV-1 and H77C by using the LSG mutations and approaches recently discovered for the TNcc and J6cc culture systems. An HCV-1 full-length genome with seventeen amino acid changes, named "HCV1cc", produced infectious virus particles with titers of ~$10^{4.0}$ focus-forming-units per milliliter (FFU/ml). By using novel mutations identified in TN full-length viruses and in HCV-1 and H77C recombinants expressing the NS5B-3'UTR from JFH1 (5-5A recombinants), we finally succeeded in developing an infectious culture system for H77, designated "H77Ccc".

The H77Ccc, with nineteen amino acid changes, replicated efficiently and spread to most culture cells within 3-5 days after transfection and subsequent infection of Huh7.5 cells, and produced infectivity titers of ~$10^{4.0}$ FFU/ml.

The HCV1cc and H77Ccc represent robust infectious cell culture systems for these key prototype strains that will contribute to HCV basic research and the development of better antiviral therapies and vaccines.

Materials and Methods

Plasmids

The HCV-1 clone HCV-1/SF9_A (GenBank accession number AF271632), which has 12 amino acid (aa) differences from the first reported HCV-1 sequence (M62321), was shown to be infectious in chimpanzees, and thus selected for this study. The HCV-1/SF9_A genome with the LSG (F1464L, A1672S, and D2979G) and TNcc-derived mutations was synthesized (GenScript), and assembled into a pGEM-9zf(-) vector containing T7 promoter for initiation of in vitro-transcription immediately upstream of the 5'UTR and an XbaI cleavage site at the end of the HCV genome (Promega), which was previously used in pCV-H77C. Other mutations were introduced by fusion PCR or by site-directed mutagenesis using QuikChange II XL kit (Agilent Technologies). The junction of the HCV-1 NS5A and JFH1 NS5B-3'UTR was synthesized (GenScript). For strain H77, we used the in vivo infectious clone pCV-H77C (GenBank accession number AF011751). The LSG and other mutations were introduced into H77C by fusion PCR or site-directed mutagenesis using the QuikChange II XL kit. All final plasmid preparations were confirmed by sequence analysis spanning the T7 promoter and the entire HCV genome (Macrogen).

Transfection and infection of Huh7.5 cells. The human hepatoma cell line Huh7.5 was maintained as described. Cells were plated in 6-well plates (~$3.5 \times 10^5$ cells/well) ~24 hours before RNA transfection or viral infection, reaching 80-90% confluence at the time of inoculation. RNA transfection and viral infection were performed as previously described. The transfected or infected cultures were incubated for ~16 hours, and sub-cultured every 2-3 days; culture supernatant was collected, filtered (0.45 µm), and stored at ~80° C. until analysis.

Analysis of HCV in cultured cells. To monitor HCV infection in the transfected and infected cultures, combination of monoclonal anti-core antibody C7-50 (Enzo Life Sciences or Abcam) and the anti-NS5A antibody 9E10 were used for immunostaining, as previously described. Percentage of HCV antigen positive cells in the culture was determined with fluorescence microscopy. Culture supernatants were collected when 80% of cells were HCV antigen positive (peak infection) and HCV infectivity titers were determined by an FFU assay using a combination of C7-50 and 9E10, as previously described. Full-length adapted HCV-1 and H77C viruses showed slightly lower intensity in staining than the positive control virus, J6$^{5'UTR-NS2}$/JFH1. The number of FFU was automatically counted with an ImmunoSpot Series 5 UV Analyzer with customized software (CTL Europe GmbH). HCV RNA titers in the culture supernatant were determined using real time RT-PCR TaqMan method. Core antigen levels were determined by the Architect HCV Ag detection system (Abbott) following manufacturer's instructions. Whole ORF sequences of passaged viruses were determined using procedures previously described for the sequencing of H77C and JFH1 genomes.

Determination of intra- and extra-cellular HCV core levels and infectivity titers. For single-cycle production assays, an Huh7-derived CD-81 deficient cell line S29 was transfected with HCV RNA and intracellular HCV core levels were measured 4 and 48 hours post transfection. Additionally, intra- and extra-cellular HCV infectivity titers, as well as extracellular HCV core concentration, were determined 48 hours post transfection, as described previously. Briefly, for this assay, S29 cells were seeded in 6 well plates (~$3.5 \times 10^5$ cells/well) 24 hours prior to transfection. Plasmids of the different full-length clones were digested with XbaI (New England Biolabs, NEB) for linearization and treated with Mung Bean nuclease (NEB). HCV RNA was generated by in vitro transcription using T7 RNA polymerase (Promega). In vitro transcripts were then digested with RNase-Free DNase Set (Qiagen) and purified with RNeasy MinElute Cleanup Kit (Qiagen). RNA was quantified using spectrophotometry (NanoDrop) and 10 µg of RNA was used for transfection with Lipofectamine 2000 (Invitrogen). Transfection was performed in duplicate, the transfection media was replaced by complete DMEM after 4 hours in one of the replicate wells, while cells from the other replicate well were harvested for determination of intracellular HCV core levels. Briefly, cells were rinsed with PBS and re-suspended in RIPA buffer (Pierce) supplemented with protease inhibitors (Calbiochem). Samples were stored at −80° C. until analysis. Prior to analysis, cell lysates were cleared by centrifugation at 14,000 rpm for 15 min and supernatants were transferred to a new tube. The same procedure was used to harvest cells at 48 hours post transfection. At this time point, supernatants were collected and filtered, for determination of extracellular core levels and infectivity titrations, as described above. Both, intra- and extra-cellular core antigen levels were determined by the Architect HCV Ag detection system (Abbott) following the manufacturer's instructions. For intracellular infectivity titers, cells were harvested and washed with PBS, then re-suspended in complete DMEM and subjected to three cycles of freeze-thaw to release intracellular virus particles. Specific dilutions were analyzed in triplicate for HCV infectivity titers, and the FFU was counted using an ImmunoSpot Series 5 UV Analyzer with customized software (CTL Europe GmbH), and confirmed by manual count.

Western Blot

Intracellular HCV core in transfected S29 cells was also visualized with western blot. Briefly, S29 transfected cell lysates (the same sample as used for determination of core with the Architect detection system) were subjected to protein denaturation at 70° C. for 10 min in the presence of NuPAGE sample reducing agent (Invitrogen) and NuPAGE LDS sample loading buffer (Invitrogen). Samples were run through 10% bis-tris SDS-polyacrylamide pre casted gels (Invitrogen) for 1 hour and 30 minutes at 150 Volts. Afterwards, separated proteins were transferred to Hybond-P polyvinylidene difluoride (PVDF) membrane (GE Healthcare Amersham) by wet electroblotting (XCell SureLock minicell, Invitrogen), at constant current during 1 hour. Membranes were then washed with PBS plus 1% Tween-20 (PBS-T) and blocked with PBS plus 1% Tween-20 and 3% bovine serum albumin for 1 hour. Blocked membranes were incubated overnight at 4° C. with anti-HCV core C7-50 or anti-β-actin (Santa Cruz Biotechnology) with gentle rocking. Immunoblotting was followed by washes with PBS-T and 1 hour incubation with ECL sheep anti-mouse IgG horseradish peroxidase-linked whole antibody (GE Healthcare Amersham). After washing, membranes were developed by chemiluminiscence using Signal West Femto maximum-sensitivity substrate (Pierce) and visualized with AutoChemi System (UVP Bio-Imaging Systems).

Results

Adaptation of an HCV-1 5'UTR-NS5A (5-5A) Recombinant Leads to Identification of the S399F Mutation.

We previously identified the LSG mutations (F1464L, A1672S, and D2979G), which permitted development of full-length HCV infectious culture systems for genotype 1a (TNcc), 2a (J6cc), and 2b (J8cc, DH8cc, and DH10cc), as well as 5-5A recombinants with JFH1 NS5B-3'UTR for genotypes 3a (S52), 4a (ED43), 5a (SA13), and 6a (HK6a).

In this study, we initially attempted to use the LSG mutations and a similar approach previously applied to J6cc and TNcc cultures, to generate an HCV-1 infectious culture system. We selected the in vivo infectious clone HCV-1/SF9_A, a genome with 12 aa differences in comparison to the first reported HCV-1 sequence (M62321). The HCV-1/SF9_A shares nucleotide sequence identity of 96% and 95% to genotype 1a infectious clones H77C and TN, respectively. Additionally, in our previously reported infectious J6cc and TNcc cell culture systems, we demonstrated that culture adaptation of 5-5A recombinants can lead to the identification of mutations critical for replication of full-length HCV genomes. Based on these prior findings, we constructed an HCV-1 5-5A recombinant containing LSG substitutions, HCV1(5-5A)_LSG (FIG. 1A), and tested its viability by RNA transfection of Huh7.5 cells. In two independent transfections, HCV core and NS5A antigens were detected in <1% of cells at day 1, but spread of infection was not observed after 45 and 56 days of follow-up. Therefore we concluded that the genome was viable but highly attenuated. We previously showed that combination of A1226G (NS3 helicase, NS3 aa position 200) and Q1773H (NS4B aa 62) could efficiently enhance the viability of TN and H77C 5-5A recombinants, and they were both included in the TNcc recombinant.

Thus, we added A1226G/Q1773H, designated as $TN_{GH}$, into HCV1(5-5A)_LSG (FIG. 1A). HCV1(5-5A)_LSG/$TN_{GH}$ showed 25% HCV positive cells at day 1 in two transfection replicates and the infection spread to ≥80% of the cultured cells (peak infection) at day 5 post transfection [Table 1 (FIG. 6)].

However, titers of transfected cultures were below the detection limit (<$10^{2.4}$ FFU/ml). Transfection supernatants could be passaged to naïve Huh7.5 cells and in first-passage the infectivity titers reached $10^{4.0}$ FFU/ml [Table 1 (FIG. 6)]. We continued passaging one of the viruses and the second-passage recovered virus reached $10^{4.5}$ FFU/ml [Table 1 (FIG. 6), exp. 2).

Sequence analysis of the ORF of first- and second-passage viruses revealed that the engineered mutations were maintained and that two additional complete changes had emerged, S399F in the hypervariable region 1 (HVR1) of E2 and D2416G in the NS5A domain III [Table 2 (FIG. 7)].

Interestingly, F399 was also found in the originally published HCV-1 sequences [M62321 and AF387806]. To determine the effects of the adaptive S399F mutation, we engineered it into the HCV1(5-5A)_LSG/$TN_{GH}$ recombinant (FIG. 1A). HCV1(5-5A)_LSG/S399F/$TN_{GH}$ showed efficient viral replication with 60% of HCV positive cells at day 1, viral spread to most cultured cells at day 4, and peak infectivity titers of $10^{2.7}$ and $10^{3.0}$ FFU/ml at days 8 and 12 in two transfections (FIG. 1B and Table 1 (FIG. 6)], indicating that S399F could enhance virus spread and infectivity. Collected culture supernatant from the two transfections was passaged to naïve Huh7.5 cells. In first-passage the peak infectivity titers increased to $10^{3.8}$ and $10^{3.9}$ FFU/ml and in second-passage to $10^{4.4}$ and $10^{4.2}$ FFU/ml [Table 1 (FIG. 6)].

Sequence analysis of one of the second-passage viruses revealed that the engineered mutations were maintained, and that two additional partial changes had emerged [Table 2 (FIG. 7)]. Taken together, these results indicate that combination of LSG, S399F, and TN-derived A1226G/Q1773H mutations permitted the HCV-1 5-5A recombinant to efficiently grow in Huh7.5 cells.

Development of an Efficient Full-Length Infectious Culture System for HCV-1.

We previously demonstrated that LSG plus Y2981F [designated "F" mutation, NS5B aa 561] were important for in vitro viability of the TNcc and full-length J6 viruses. LSG plus S399F/$TN_{GH}$ could efficiently adapt the HCV-1 5-5A recombinant, in which S399F enhanced virus spread and infectivity (FIG. 1B and Table 1 (FIG. 6)].

Thus, here we attempted to combine these mutations and to test their adaptation potential in the full-length HCV-1 genome. For that purpose, we generated HCV-1 with LSGF/S399F/$TN_{GH}$, LSGF/S399F/TNm ["TNm" for four TNcc adaptive mutations A1226G/Q1773H/N1927T/F2994S], or LSGF/TNm (FIG. 1A). Replication was not observed for HCV1_LSGF in transfected cultures for up to 20 days of follow-up.

Cultures transfected with HCV1_LSGF/S399F/$TN_{GH}$ showed HCV positive cells beginning from day 4 but continued to have <1% of HCV positive cells for up to 20 days of follow-up with no evidence of viral spread. The HCV1_LSGF/TNm culture showed 1% HCV positive cells at day 1, but no evidence of viral spread for up to 41 days. In contrast, the HCV1_LSGF/S399F/TNm culture showed 10% HCV infected cells at day 1, reached peak of infection after 26 days, and released HCV infectivity titers of $10^{3.3}$ FFU/ml (FIG. 1C), indicating that S399F mediated viral spread of full-length HCV1_LSGF/TNm and that N1927T and F2994S also contributed to a more efficient viral propagation.

After passages to naïve Huh7.5 cells, the first-, second-, and third-passage HCV1_LSGF/S399F/TNm showed peak infectivity titers of $10^{3.4}$, $10^{4.3}$, and $10^{4.2}$ FFU/ml, respectively [Table 1 (FIG. 6)]. ORF sequence analysis of the second- and third-passage viruses revealed that the introduced mutations were all maintained and that eight additional amino acid changes [A970T, I1312V, I1326V, V2198A, I2268T, C2419R, E2622D, and A2919T (designated "8m")] had emerged [Table 3 (FIG. 8)].

In order to generate an efficient HCV-1 full-length virus, we tested the importance of the mutations identified from passaged HCV1_LSGF/S399F/TNm viruses (see above). We introduced individual mutations or a combination of "8m" into the HCV1_LSGF/S399F/TNm recombinant. At day 1 after transfection, the recombinants with single mutations A970T, I1312V, I1326V, V2198A, I2268T, C2419R, or E2622D showed low number of HCV positive cells, and in addition no evidence of viral spread was observed after one week of follow-up. In contrast, the recombinant with A2919T showed 40% HCV positive cells at day 1 and reached 80% at day 4, remaining at this percentage for two weeks, albeit with low HCV infectivity titers ($<10^{2.4}$ FFU/ml). These results indicated that A2919T may play a greater role than the remaining seven mutations in adaptation of HCV1_LSGF/S399F/TNm. The genome with all mutations combined, designated HCV1_LSGF/S399F/TNm/8m, showed 55% HCV positive cells at day 1 in two transfection replicates and released peak HCV infectivity titers of $10^{3.8}$-$10^{4.0}$ FFU/ml (FIG. 1D and Table 1 (FIG. 6)].

The transfection-derived virus showed efficient spread in first- and second-passage, and both passage-recovered viruses had peak infectivity titers of $10^{3.8}$ FFU/ml [Table 1 (FIG. 6)]. ORF sequence analysis of the second-passage virus demonstrated that all the engineered mutations were maintained, and that no additional mutations were present. Taken together, these results indicate that the combination of "8m" efficiently enhances the replication and viral production of HCV-1, resulting in an efficient full-length HCV-1 infectious culture system. We therefore designated HCV1_LSGF/S399F/TNm/8m as "HCV1cc" (for "HCV-1 cell culture-derived").

Mutations Important for the Viability of HCV1cc

As addition of the "8m" mutations led to a robust HCV1_LSGF/S399F/TNm virus (FIGS. 1C and D), we next examined which of the mutations primarily contributed to efficient viral viability. For this purpose, we mutated each of the "8m" mutations individually back to the wild-type sequence, and tested the effect on the viability of the virus after transfection of Huh7.5 cells (FIGS. 2A and B).

Compared to HCV1cc, viruses with –A970T (adaptive mutation A970T reverted to wild-type), –I1312V, and –C2419R were attenuated and did not produce HCV infectivity titers detectable until day 8 after transfection, at which time point their titers were approximately 7.9, 1.7, and 2.0-fold lower than HCV1cc, respectively. Moreover, the virus with –A2919T was highly attenuated as HCV titers were first detected on day 13. Additionally, peak infectivity titers for both –A970T and –A2919T viruses were slightly lower than for the remaining viruses (FIG. 2A), specifically 2.8 and 3.2-fold lower than HCV1cc.

When analyzing secreted core antigen levels in the supernatants of transfected cells, we observed that the mutant –A2919T, the most attenuated, had core levels that were 4.7-21 fold lower than those for HCV1cc at the same time points (FIG. 2B), whereas other viruses showed core levels 0.5-3 fold within those of HCV1cc. Together, these results indicate that the absence of A970T, I1312V, C2419R, or A2919T all affect the viability of HCV1cc, with the absence of A2919T having the greatest effect.

Next, we explored whether the four mutations A970T, I1312V, C2419R, and A2919T (designated "4m"), singly or combined, were sufficient to adapt HCV1_LSGF/S399F/TNm to comparable growth as HCV1cc. Since A2919T played a major role for the viability of HCV1cc (FIG. 2A), in addition to the "4m" we tested HCV1_LSGF/S399F/TNm with A2919T plus any combinations of the other three mutations, namely A970T/A2919T, I1312V/A2919T, C2419R/A2919T, A970T/I1312V/A2919T (designated "3m"), A970T/C2419R/A2919T, and I1312V/C2419R/A2919T. After transfection of Huh7.5 cells, only the viruses containing "3m" and "4m" spread to ≥80% of culture cells within 6 days (FIG. 3A); the viruses with other combinations did not spread. HCV1_LSGF/S399F/TNm/4m produced detectable infectivity titers from day 4, though the HCV peak titers were slightly lower than those of HCV1cc (FIG. 3A), whereas HCV1_LSGF/S399F/TNm/3m did not produce detectable HCV infectivity titers until day 13. However, supernatant core levels of both "3m" and "4m" viruses were similar to those of HCV1cc at each time point (FIG. 3B). From these results, we conclude that "4m" mutations are the minimum required for efficient production of infectious viruses of the HCV1_LSGF/S399F/TNm genome, in vitro.

Effect of HCV-1 Adaptive Mutations on Viral Replication, Assembly, and Release.

To address the role of the identified adaptive mutations in replication, assembly and release of HCV1cc, we performed a single-cycle-production assay using Huh7 derived S29 cells, a cell line that is deficient for the HCV entry receptor CD81. Since the A970T/I1312V/C2419R/A2919T (4m) mutations played a major role in the viability of HCV1cc, in which A970T and A2919T seemed to have a greater effect (FIG. 2A), we tested the effect of A970T/A2919T with I1312V, C2419R, or with I1312V/C2419R in the HCV1_LSGF/S399F/TNm backbone. After transfection of S29 cells, the intracellular and extracellular infectivity titers (FIG. 4A) and corresponding HCV core antigen levels (FIGS. 4B and C) were determined. In addition, the intracellular HCV core levels were visualized by western blot (FIG. 4D), and the results agreed with the measurements obtained by using the Architect HCV Ag detection system (FIGS. 4B and D).

As expected, in the absence of "4m" mutations, HCV1_LSGF/S399F/TNm failed to produce detectable intracellular and extracellular infectivity titers (FIG. 4A), and intracellular core levels were barely over those of the replication-deficient control, J6/JFH1-GND (FIG. 4B). In a separate experiment, we also tested HCV1_LSGF and HCV1_LSGF/TNm in parallel with HCV1cc. Likewise, HCV1_LSGF/S399F/TNm, HCV1_LSGF and HCV1_LSGF/TNm failed to produce detectable levels of both intracellular and extracellular infectivity titers and showed a low level of intracellular and extracellular core antigen 48 hours after transfection (data not shown). Addition of A970T/A2919T into the HCV1_LSGF/S399F/TNm genome had only a minor effect on core levels and no effect on infectivity titers.

However, addition of I1312V or C2419R to A970T/A2919T mutations led to detectable intracellular infectious titers and increase in extracellular core level, however, no extracellular infectious virus were detected (FIG. 4A-C). These results suggest that both I1312V and C2419R played an important role in assembly of infectious virus particles, but had no or insufficient effect in virus release. Interestingly, when both I1312V and C2419R were combined with A970T/A2919T, thus making the genome with the "4m" mutations, virus release of infectious viral particles was enhanced and the virus produced extracellular infectivity titers comparable to those of HCV1cc (FIG. 4A), with an increase in extracellular core levels (FIG. 4C). Based on the results of the single-cycle production assay, we concluded that the "4m" mutations (A970T/I1312V/C2419R/A2919T) when added into the HCV1_LSGF/S399F/TNm genome permit an efficient completion of the viral life cycle, and that the combination of I1312V/C2419R apparently is required for efficient virus release of infectious viral particles. It should also be noted that although "4m" mutations were essential for the viability of HCV1_LSGF/S399F/TNm, the combination of "8m" further increased intracellular core levels (FIG. 4B) and intracellular infectivity titers (FIG. 4A), thus suggesting that all "8m" mutations further increased replication and virus assembly of HCV-1.

Development of an Efficient Full-Length Infectious Culture System for H77.

After our success in adapting genotype 1a strains TN and HCV-1 for efficient growth in vitro, we wanted to determine whether the key adaptive mutations we uncovered could be used to adapt H77C, another important HCV prototype strain. We recently demonstrated that the LSGF and LSGF/TNm mutations were not sufficient to adapt the H77C genome after transfection in Huh7.5 cells. However, the LSG and TN(5-5A)-adaptive mutations A1226G/Q1773H could efficiently adapt an H77C 5-5A recombinant [previously named "1a(H77)_LSG/A1226G/Q1773H" in Li et al. Gastroenterology. 2014 March; 146(3):812-821]. After passage, the virus acquired a partial change in the NS3 helicase, S1368P, which became dominant after second-passage. Interestingly, this mutation was also identified here in the two cell culture adapted HCV-1 5-5A viruses [Table 2 (FIG. 7)].

We previously found that a TN genome containing only LSGF, designated TN_LSGF, was non-viable in a single transfection. However, when we repeated transfections of the TN_LGSF for this study, we were able to obtain viral replication in one out of three transfections. In that unique transfection, TN-LSGF showed a low number of HCV positive cells at day 4 with infection spreading to ≥80% of cultured cells after 28 days of follow-up. The transfection-derived TN_LSGF culture supernatant had infectivity titers of $10^{4.0}$ FFU/ml, and the titers reached $10^{4.7}$ and $10^{4.9}$ FFU/ml after first- and second-passage, respectively. Amongst other mutations, both passage-recovered viruses acquired the change F2994R, which may be of importance since F2994 was changed to serine (F2994S) in our previously reported TNcc system.

Based on this new information, we hypothesized that combining mutations S1368P and F2994R might permit replication of an H77C genome with LSGF/TNm, and therefore we generated H77C_LSGF/TNmr/S1368P (TNmr indicates that F2994S of TNm was replaced with F2994R). After transfection of Huh7.5 cells, the H77C_LSGF/TNmr/S1368P showed a few HCV positive cells for up to three months, but finally the infection spread to ≥80% of cells at day 96, producing HCV peak infectivity titers of $10^{3.5}$ FFU/ml (FIG. 5A). First- and second-passage viruses spread to ≥80% of cells within 8-10 days and reached peak HCV infectivity titers of $10^{3.5}$ and $10^{4.2}$ FFU/ml (FIG. 5A). ORF sequence analysis revealed that viruses had acquired 10 complete amino acid changes M345T, A828V, L864R, K1052R, V1663A, G1909S, M2105V, S2354G, V2417A, and V2431I, which we designated "10m" [Table 4 (FIG. 9)]. We therefore engineered the "10m" into the H77C_LSGF/TNmr/S1368P clone. After transfection of Huh7.5 cells, H77C_LSGF/TNmr/S1368P/10m spread to ≥80% of culture cells within 3 days. The culture supernatant had a peak infectivity titer of $10^{3.5}$ FFU/ml. The first- and second-passage viruses reached infectivity titers of $10^{4.4}$ and $10^{3.8}$ FFU/ml, respectively (FIG. 5B).

In ORF sequencing analysis of the second-passage virus, all the engineered mutations were maintained, and no additional changes were found [Table 4 (FIG. 9)]. Hence, we had developed a robust infectious culture system for full-length H77C clone, with efficient virus spread after transfection and subsequent infection, and we named the adapted recombinant "H77Ccc".

DISCUSSION

In this study, we developed highly efficient cell culture systems for full-length HCV prototype strains HCV-1 and H77 (both genotype 1a strains), named HCV1cc and H77Ccc, by using mutations and approaches previously developed for the J6cc (2a) and TNcc (1a) infectious clones. HCV1cc and H77Ccc replicated efficiently following RNA transfection of human hepatoma Huh7.5 cells and produced HCV infectivity titers of ~$10^4$ FFU/ml, showing no additional amino acid changes after second-round viral passage. Given the clinical significance of genotype 1 and the uniquely important role of these prototype strains in HCV research, the HCV1cc and H77Ccc systems will be of particular value and will provide useful tools for future studies of HCV.

After development of the first HCV infectious culture system based on the genotype 2a JFH1 strain, tremendous efforts have been made to propagate HCV isolates of other genotypes in culture. Genotype 1 account for ~60% of HCV infections worldwide, thus culture systems for genotype 1 have great interest for HCV research. Recently, we identified three mutations, designated "LSG" (F1464L/A1672S/D2979G), initially through studies of genotype 2a J6-JFH1 recombinants. The LSG mutations were essential for the development of full-length in vitro infectious clones of HCV genotypes 1a (TNcc), 2a (J6cc), and 2b (J8cc, DH8cc, and DH10cc).

Replication of 2a and 2b recombinants could be initiated by LSG alone, thus permitting further adaptation that led to robust infectious culture systems. We also showed that the LSG mutations played an important role in the adaptation of JFH1-based 5-5A recombinants of genotypes 1-6. In this study, we further demonstrated that LSG combined with an NS5B mutation Y2981F (interestingly most genotype 2b isolates naturally have F2981) have the potential to initiate adaption of additional genotypes, such as the genotype 1a strain TN. It would be worth exploring in future studies, whether LSG or LSGF per se can promote cell culture viability for other HCV isolates, as a first step in the process of cell culture adaptation. Our experience with the TN_LSGF genome also suggests that multiple transfections may be required to start cell culture adaptation of isolates with low level of viral replication, and that negative results from a single experiment can be misleading.

Adaptation of HCV-1 and H77C required additional mutations other than LSGF, therefore strengthening the notion that cell culture adaptation is highly influenced by the nature of the genome sequence. In order to start replication of HCV-1 and H77C, we combined LSG or LSGF with other mutations, TNm or TNmr mutations from the efficient in vitro infectious full-length TN clones, S399F from HCV1 (5-5A) recombinants, and S1368P from H77C(5-5A) or HCV1(5-5A) recombinants [Table 2 (FIG. 7)]). This broad set of adaptive mutations may represent a valid evolutionary path leading to the culture adaptation of several additional genotype 1a strains, including strains showing high genetic diversity to TN, H77 and HCV-1, and thus permitting the generation of a wide panel of infectious clones, which could be relevant for studies of strain-related genetic variability in HCV genotype 1a.

Some positions in the HCV genome are under different selective pressure in vivo and in vitro. In this study, the HVR1 amino acid S399 was changed to F399, which matched the originally reported HCV-1 sequence. This change may indicate that although an HCV-1 clone with S399 was found viable in vivo, F399 may be a more optimal residue for in vitro viability. A recent study showed that cell culture adaptive mutations in H77-S with replicon adaptive mutations reverted to wild-type residues over time in persistently infected chimpanzees. In addition, culture replication-enhancing mutations were found to prevent productive in vivo replication of the Con1 genome. This discrepancy in requirements for in vitro and in vivo viability may explain the difficulties of propagating HCV recombinants in cell culture, even for those found viable in vivo, as was the case for the original genomes of HCV-1, H77, and TN. In a recent study the natural resistance to lipid induced peroxidase stress of JFH1 was found to be correlated with its robust replication capacity in cell culture. Moreover, the authors demonstrated that our highly efficient cell culture adapted TNcc similarly had resistance to lipid peroxidation. It would be of interest for future studies to explore if this interesting finding is also applicable to other cell culture adapted genomes, including genomes not depending on the specific TN-derived adaptive mutations.

In addition to the mutations used for promoting initial viral replication and adaptation of HCV-1 and H77C, most of which we had already described, the final HCV1cc and H77Ccc clones contained a number of additional mutations, for instance, HCV1cc contained a total of seventeen amino acid changes compared to the original HCV1/SF_A clone. We demonstrated that 4 of the additional HCV1cc amino acid changes were critical for efficient adaptation (A970T, I1312V, C2419R and A2919T). From those, A970T (aa 161 in NS2), is a highly conserved position (Los Alamos HCV Sequence Databases) and only 1 out of 4306 sequences has a different residue. C2419R is another highly conserved residue located carboxy-terminally in NS5A. On the other hand, amino acid 1312, in the NS3 helicase, is a polymorphic site. 11312 is present in genotypes 1a, 1b, 2a, and 6a, while V1312 is primarily found in genotypes 3 and 5. The fact that V1312 can be found in natural viral sequences shows that some cell culture adaptive changes can be found in circulating viruses, albeit from other genotypes. Likewise, amino acid 2919 in NS5B is a variable position, and A, V and T can be found in various genotypes. Among the remaining cell culture adaptive mutations present in HCV1cc, position 1326 (aa 300 in NS3, helicase domain) contain either I or V depending on the genotype. HCV isolates have different amino acids in NS5A position 2198 (aa 226 in NS5A), including L, V, E, M or Q, similarly to position 2268 (296 in NS5A, in the PKR binding domain) where V, I, P, L and M can be found. Finally, at NS5B position 2622 (aa 202 in NS5B), isolates from the HCV database contain only E or D.

In previous studies, it was assumed that certain cell culture adaptive mutations identified in JFH1-based intergenotypic recombinants compensated for incompatibilities due to the chimeric nature of those genomes. However, since many of those changes also emerged in cell culture adapted full-length genomes, they are most likely related to the cell-culture adaptation process. One of these changes is the HCV-1 adaptive mutation I1312V, that was also identified in a passaged full-length DH10 (2b) virus, which had been previously shown to adapt JFH1-based core-NS2 recombinants. Another HCV-1 change, C2419R, was identified in a DH8_LSG (2b) full-length genome and was observed for adaptation of a J6/JFH1-based recombinant expressing the NS5A from H77 and with p7 mutations.

To understand the role of adaptive mutations in various steps of the HCV1cc life cycle, we performed single-cycle production assays using S29 cells. The S29 cells were derived from Huh7 cells but are deficient in CD81, and thus only support HCV RNA replication, virus particle assembly and release, but not infection. HCV-1 genomes containing only LSGF or LSGF/S399F/TNm failed to efficiently replicate or to produce detectable infectious particles in the S29 cell assays (FIG. 4A). These results agreed with observations after transfection of Huh7.5 cells, in which both viruses started to spread only after 26 days, and this culture spread was related to the emergence of additional mutations [Table 3 (FIG. 8)]. In line with this finding, we had previously shown that LSG alone did not lead to high HCV infectivity titers of the J6 full-length genome.

In contrast, addition of the "8m" mutations in HCV-1 with LSGF/S399F/TNm resulted in efficient replication and virus production with augmented supernatant infectivity titers in S29 cells (FIG. 4). These results suggest that these mutations mediated efficient replication, virus assembly and release, which was also in agreement with the rapid virus spread of genomes containing "8m" mutations, after transfection of Huh7.5 cells (FIG. 1D).

The "4m" (A970T/I1312V/C2419R/A2919T) mutations were sufficient to achieve efficient virus spread and release, although with slightly lower levels compared to HCV1cc. Therefore, "4m" apparently were the minimal set of mutations required to complete an efficient viral life cycle of the HCV-1 with LSGF/S399F/TNm. Of the "4m" mutations, the A970T/A2919T combination was not sufficient to confer efficient viral replication and assembly in S29 cells (FIG. 4), however, when combined with either C2419R or I1312V, replication and assembly were significantly augmented, and therefore we concluded that they played a major role in these processes (FIG. 4A).

Additionally, for our experiments in Huh7.5 cells, changing T2919 back to wild-type A2919 significantly reduced viability of HCV1cc (FIG. 2A). Amino acid 2919 (NS5B 499) is in the thumb domain of the polymerase, and has been related to viral replication. This position shows a certain level of polymorphism, and amino acid changes at this site have different effects, depending on the strain. In genotype 2a replicon systems, the V2919A change had no effect on JFH1, but A2919V increased the replication of J6 by 10-fold. In addition, in the context of full-length genotype 2a systems, A2919V was recently described as a cell culture adaptive mutation in PR63cc, having an effect in replication of this strain.

Interestingly, when both I1312V and C2419R were combined with A970T/A2929T, extracellular infectivity titers were detectable (FIG. 4A), but increase in supernatant titers was not associated with an increase in replication, and therefore indicating that the combination of I1312V and C2419R may have an important specific role in release of infectious viral particles. It will be of interest to elucidate, in future studies, whether the rescue of release is mediated uniquely through the interaction of these two positions, located in NS3 and NS5A, or by the recruitment of other viral or host proteins.

Given the historical importance of H77 in HCV research, much effort has been invested in propagating this strain in cell culture, in particular since infectious clones were developed in 1997.

The H77Ccc developed in this study showed efficient replication after RNA transfection of Huh7.5 cells, with infectivity titers of $10^{3.6}$ FFU/ml (FIG. 5B). Importantly, H77Ccc spread rapidly after passage to naïve Huh7.5 cells, and the first- and second-passage viruses reached peak of infection within 5-8 days and produced infectivity titers of $10^{4.4}$ and $10^{3.8}$ FFU/ml, respectively (FIG. 5B and Table 4 (FIG. 9)]. Therefore, the H77Ccc represents a robust and efficient infectious cell culture system for HCV strain H77, with high replication levels after transfection and rapid spread in viral passage cultures.

It was initially found by Yi et al. that an H77C genome carrying mutations derived from its replicon system replicated at a low level in transfected Huh7.5 cells. Subsequently, this genome was improved to yield higher infectivity titers by introducing an additional mutation in E2 (H77S.3), and during the preparation of this manuscript a further adapted genome (H77D) that replicated and spread efficiently in cell culture was reported. Similarly to the adaptation process described in this study, H77D was generated by introducing our previously described adaptive TNcc mutations into the H77S.3 backbone. Replication of H77S.3/LSGF/TNm was inhibited, but removal of an adaptive mutation from the original H77S.3 (S2204I) permitted replication and further adaptation of this genome, that was passaged until high titer viruses emerged. The cell culture adapted emerging viruses, which showed significant replication enhancement, contained 3 additional amino acid changes, G1909S (NS4B), D2416G (NS5A) and G2963D (NS5B). Interestingly, our adapted H77Ccc also contains G1909S in NS4B, but with V2417A instead of D2416G in NS5A, and V2431I instead of G2963D in NS5B. Both independent approaches for efficient adaptation of H77C thus depended on adaptive mutations from TN cultures, which was the first efficient genotype 1 culture system. Thus, the TNcc adaptive mutations might be valuable for adaptations of additional HCV strains to efficient growth in culture as was also found for the HCV-1 strain in the present study.

In conclusion, we have developed two efficient high-titer culture systems for the globally prevalent HCV genotype 1. The HCV1cc and H77Ccc represent efficient in vitro infectious systems for two historically important strains that have been the foundation for the development of diagnostic tests and key research material in the field, including the discovery of HCV. Both cell culture systems, together with other infectious full-length HCV genomes, will permit genotype- and isolate-specific functional studies of the viral life cycle and of specific viral proteins and their interactions with cellular components. This knowledge will then contribute to basic research on different aspects of HCV and help improving antiviral therapy and future vaccine development.

The invention claimed is:

1. An isolated nucleic acid molecule which encodes a human hepatitis C of strain genotype 1a, virus, wherein said molecule:
   (i) is capable of expressing said virus when transfected into cells,
   (ii) is capable of infectivity in vivo,
   (iii) comprises at least one adaptive mutation in the amino acid sequence of NS3, which is F1464L,
   (iv) comprises at least one adaptive mutation in the amino acid sequence of NS4A which is A1672S, and
   (v) comprises at least one adaptive mutation in the amino acid sequence of NS5B which is D2979G, and
   (vi) the following additional adaptive mutations in the amino acid sequence: S399F, A970T, I1312V, I1326V, V2198A, I2268T, C2419R, E2622D and A2919T, wherein the positions are according to GenBank accession number AF009606 (SEQ ID NO: 7) or the following additional adaptive mutations in the amino acid sequence: M345T, A828V, L864R, K1052R, S1368P, V1663A, G1909S, M2105V, S2354G, V2417A and V2431I,
   wherein the positions are according to GenBank accession number AF009606 (SEQ ID NO:7).

2. The isolated nucleic acid molecule according to claim 1, wherein the hepatitis C virus is of genotype 1a and is isolate HCV1cc (SEQ ID NO:1).

3. The isolated nucleic acid molecule according to claim 1, wherein the hepatitis C virus is of genotype 1a and is isolate H77Ccc (SEQ ID NO:3).

4. A method for producing a cell, which replicates human hepatitis C virus and produces a virus particle comprising
   introducing a nucleic acid molecule according to claim 1 into a cell.

5. A method for screening an anti-hepatitis C virus substance, comprising
   a) culturing a cell comprising the nucleic acid of claim 1 together with a hepatitis C virus permissive cell, and
   b) detecting the replicating RNA or the virus particles in the resulting culture.

* * * * *